United States Patent
Fehr et al.

(10) Patent No.: US 12,071,664 B2
(45) Date of Patent: *Aug. 27, 2024

(54) OPTICS COLLECTION AND DETECTION SYSTEM AND METHOD

(71) Applicant: Pacific Biosciences of California, Inc., Menlo Park, CA (US)

(72) Inventors: Adrian Fehr, San Francisco, CA (US); Nathaniel Joseph McCaffrey, Mill Valley, CA (US); Stephen Turner, Seattle, WA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/939,760

(22) Filed: Sep. 7, 2022

(65) Prior Publication Data
US 2023/0175060 A1    Jun. 8, 2023

Related U.S. Application Data

(63) Continuation of application No. 15/195,493, filed on Jun. 28, 2016, now abandoned, which is a
(Continued)

(51) Int. Cl.
*C12Q 1/6874* (2018.01)
*B01L 3/00* (2006.01)
(Continued)

(52) U.S. Cl.
CPC ...... *C12Q 1/6874* (2013.01); *B01L 3/502707* (2013.01); *B01L 3/502715* (2013.01); *B82Y 20/00* (2013.01); *C12Q 1/6825* (2013.01);
*C12Q 1/6869* (2013.01); *G01N 21/03* (2013.01); *G01N 21/0303* (2013.01); *G01N 21/05* (2013.01); *G01N 21/64* (2013.01); *G01N 21/6428* (2013.01); *G01N 21/645* (2013.01); *G01N 21/6452* (2013.01); *G01N 21/6454* (2013.01);
(Continued)

(58) Field of Classification Search
None
See application file for complete search history.

(56) References Cited

U.S. PATENT DOCUMENTS 4,818,710 A    4/1989    Sutherland et al.
4,971,903 A    11/1990   Hyman
(Continued)

FOREIGN PATENT DOCUMENTS

EP    0911630 A1    4/1999
EP    2783919 A1    3/2000
(Continued)

OTHER PUBLICATIONS

Bernini et al., "Polymer-on-glass waveguide structure for efficient fluorescence-based optical biosensors" Proc. SPIE (2005) 5728:101-111.
(Continued)

*Primary Examiner* — Xiaoyun R Xu

(57) ABSTRACT

Optics collection and detection systems are provided for measuring optical signals from an array of optical sources over time. Methods of using the optics collection and detection systems are also described.

20 Claims, 41 Drawing Sheets

Related U.S. Application Data continuation of application No. 13/031,146, filed on Feb. 18, 2011, now Pat. No. 9,410,891.

(60) Provisional application No. 61/410,189, filed on Nov. 4, 2010, provisional application No. 61/387,916, filed on Sep. 29, 2010, provisional application No. 61/306,235, filed on Feb. 19, 2010.

(51) Int. Cl.
| | |
|---|---|
| B82Y 20/00 | (2011.01) |
| C12Q 1/6825 | (2018.01) |
| C12Q 1/6869 | (2018.01) |
| G01N 21/03 | (2006.01) |
| G01N 21/05 | (2006.01) |
| G01N 21/64 | (2006.01) |
| G01N 21/75 | (2006.01) |
| G01N 21/77 | (2006.01) |
| G01N 33/543 | (2006.01) |
| G02B 6/122 | (2006.01) |

(52) U.S. Cl.
CPC ....... *G01N 21/6456* (2013.01); *G01N 21/648* (2013.01); *G01N 21/75* (2013.01); *G01N 21/77* (2013.01); *G01N 33/54373* (2013.01); *G02B 6/1226* (2013.01); *B01L 2300/0654* (2013.01); *B01L 2300/0663* (2013.01); *B01L 2300/0816* (2013.01); *B01L 2300/168* (2013.01); *G01N 2021/0346* (2013.01); *G01N 2021/6434* (2013.01); *G01N 2021/6439* (2013.01); *G01N 2021/6441* (2013.01); *G01N 2021/6463* (2013.01); *G01N 2021/757* (2013.01); *G01N 2021/7786* (2013.01); *G01N 2201/067* (2013.01); *G01N 2201/068* (2013.01); *G01N 2201/08* (2013.01); *Y10T 436/143333* (2015.01)

(56) References Cited

U.S. PATENT DOCUMENTS

| | | |
|---|---|---|
| 5,082,629 A | 1/1992 | Burgess, Jr. et al. |
| 5,094,517 A | 3/1992 | Franke |
| 5,157,262 A | 10/1992 | Marsoner et al. |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,302,509 A | 4/1994 | Cheeseman |
| 5,439,647 A | 8/1995 | Saini |
| 5,446,534 A | 8/1995 | Goldman |
| 5,470,710 A | 11/1995 | Weiss et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,812,709 A | 9/1998 | Arai et al. |
| 5,821,058 A | 10/1998 | Smith et al. |
| 5,832,165 A | 11/1998 | Reichert et al. |
| 5,834,758 A | 11/1998 | Trulson et al. |
| 5,867,266 A | 2/1999 | Craighead et al. |
| 5,871,628 A | 2/1999 | Dabiri et al. |
| 5,872,623 A | 2/1999 | Stabile et al. |
| 5,874,219 A | 2/1999 | Rava et al. |
| 5,919,712 A | 7/1999 | Herron et al. |
| 5,925,525 A | 7/1999 | Fodor et al. |
| 6,051,380 A | 4/2000 | Sosnowski et al. |
| 6,071,748 A | 6/2000 | Modlin et al. |
| 6,072,196 A | 6/2000 | Sato |
| 6,140,048 A | 10/2000 | Muller et al. |
| 6,140,054 A | 10/2000 | Wittwer et al. |
| 6,147,198 A | 11/2000 | Schwartz et al. |
| 6,192,168 B1 | 2/2001 | Feldstein et al. |
| 6,198,869 B1 | 3/2001 | Kraus et al. |
| 6,210,891 B1 | 4/2001 | Nyren et al. |
| 6,210,896 B1 | 4/2001 | Chan |
| 6,236,945 B1 | 5/2001 | Simpson et al. |
| 6,258,568 B1 | 7/2001 | Nyren |
| 6,263,286 B1 | 7/2001 | Gilmanshin et al. |
| 6,325,977 B1 | 12/2001 | Theil |
| 6,331,441 B1 | 12/2001 | Balch et al. |
| 6,362,498 B2 | 3/2002 | Abramovich |
| 6,384,912 B2 | 5/2002 | Kraus et al. |
| 6,388,788 B1 | 5/2002 | Harris et al. |
| 6,437,345 B1 | 8/2002 | Bruno-Raimondi et al. |
| 6,438,279 B1 | 8/2002 | Craighead et al. |
| 6,448,064 B1 | 9/2002 | Vo-Dinh et al. |
| 6,483,096 B1 | 11/2002 | Kunz et al. |
| 6,542,528 B1 | 4/2003 | Sato et al. |
| 6,545,758 B1 | 4/2003 | Sandstrom |
| 6,573,089 B1 | 6/2003 | Vann |
| 6,580,496 B2 | 6/2003 | Bamji et al. |
| 6,603,537 B1 | 8/2003 | Dietz et al. |
| 6,611,634 B2 | 8/2003 | Herron et al. |
| 6,633,659 B1 | 10/2003 | Zhou |
| 6,646,709 B2 | 11/2003 | Matsumoto |
| 6,674,785 B2 | 1/2004 | Sato et al. |
| 6,690,002 B2 | 2/2004 | Kuroda et al. |
| 6,699,655 B2 | 3/2004 | Nikiforov et al. |
| 6,744,196 B1 | 6/2004 | Jeon |
| 6,784,982 B1 | 8/2004 | Blumenfeld et al. |
| 6,800,860 B2 | 10/2004 | Dietz et al. |
| 6,812,539 B1 | 11/2004 | Rhodes |
| 6,818,395 B1 | 11/2004 | Quake et al. |
| 6,867,851 B2 | 3/2005 | Blumenfeld et al. |
| 6,897,927 B2 | 5/2005 | Tanaka et al. |
| 6,906,302 B2 | 6/2005 | Drowley |
| 6,917,726 B2 | 7/2005 | Levene et al. |
| 6,919,211 B1 | 7/2005 | Fodor et al. |
| 6,933,168 B2 | 8/2005 | Bawolek et al. |
| 6,977,726 B2 | 12/2005 | Farr |
| 6,979,830 B2 | 12/2005 | Dietz et al. |
| 6,982,146 B1 | 1/2006 | Schneider et al. |
| 6,982,165 B2 | 1/2006 | Yamakawa et al. |
| 7,041,529 B2 | 5/2006 | Yamada et al. |
| 7,052,847 B2 | 5/2006 | Korlach et al. |
| 7,056,661 B2 | 6/2006 | Korlach et al. |
| 7,057,832 B2 | 6/2006 | Wu et al. |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,150,997 B2 | 12/2006 | Kovacs |
| 7,175,811 B2 | 2/2007 | Bach et al. |
| 7,181,122 B1 | 2/2007 | Levene et al. |
| 7,189,361 B2 | 3/2007 | Carson et al. |
| 7,197,196 B2 | 3/2007 | Lin et al. |
| 7,199,357 B1 | 4/2007 | Oldham et al. |
| 7,209,836 B1 | 4/2007 | Schermer et al. |
| 7,214,346 B2 | 5/2007 | Harper et al. |
| 7,216,671 B2 | 5/2007 | Unger et al. |
| 7,227,128 B2 | 6/2007 | Sagatelyan |
| 7,248,771 B2 | 7/2007 | Schmidt et al. |
| RE39,772 E | 8/2007 | Herron et al. |
| 7,271,896 B2 | 9/2007 | Chan et al. |
| 7,302,149 B2 | 11/2007 | Turner et al. |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,361,466 B2 | 4/2008 | Korlach |
| 7,385,460 B1 | 6/2008 | Wang et al. |
| 7,400,380 B2 | 7/2008 | Hahn |
| 7,443,489 B2 | 10/2008 | Natan |
| 7,476,504 B2 | 1/2009 | Turner |

(56) References Cited

U.S. PATENT DOCUMENTS

| | | |
|---|---|---|
| 7,486,865 B2 | 2/2009 | Foquet et al. |
| 7,501,241 B2 | 3/2009 | Matsushita et al. |
| 7,626,704 B2 | 12/2009 | Lundquist et al. |
| 7,630,073 B2 | 12/2009 | Lundquist et al. |
| 7,704,735 B2 | 4/2010 | Facer et al. |
| 7,709,808 B2 | 5/2010 | Reel et al. |
| 7,767,441 B2 | 8/2010 | Chiou et al. |
| 7,811,810 B2 | 10/2010 | Chiou et al. |
| 7,820,983 B2 | 10/2010 | Lundquist et al. |
| 8,053,742 B2 | 11/2011 | Lundquist et al. |
| 8,133,719 B2 | 3/2012 | Drmanac et al. |
| 8,247,216 B2 | 8/2012 | Zaccarin et al. |
| 9,096,898 B2 | 8/2015 | Williams et al. |
| 9,551,030 B2 | 1/2017 | Turner et al. |
| 10,138,515 B2 | 11/2018 | Fehr et al. |
| 2001/0041025 A1 | 11/2001 | Farahi |
| 2001/0041394 A1 | 11/2001 | Park et al. |
| 2002/0018199 A1 | 2/2002 | Blumenfeld et al. |
| 2002/0034457 A1 | 3/2002 | Reichert et al. |
| 2002/0094147 A1 | 7/2002 | Herron et al. |
| 2002/0110839 A1 | 8/2002 | Bach et al. |
| 2002/0113213 A1 | 8/2002 | Amirkhanian et al. |
| 2002/0146047 A1 | 10/2002 | Bendett et al. |
| 2002/0155592 A1 | 10/2002 | Kelleher et al. |
| 2002/0182716 A1 | 12/2002 | Weisbuch et al. |
| 2003/0044781 A1 | 3/2003 | Korlach et al. |
| 2003/0132406 A1 | 7/2003 | Waldhausl et al. |
| 2003/0133681 A1 | 7/2003 | Bozhevolnyi |
| 2003/0138180 A1 | 7/2003 | Kondo |
| 2003/0174324 A1 | 9/2003 | Sandstrom |
| 2003/0174992 A1 | 9/2003 | Levene et al. |
| 2003/0190632 A1 | 10/2003 | Sosnowski et al. |
| 2003/0201462 A1 | 10/2003 | Pommer et al. |
| 2003/0210399 A1 | 11/2003 | Bahatt et al. |
| 2004/0005582 A1 | 1/2004 | Shipwash |
| 2004/0040868 A1 | 3/2004 | Denuzzio et al. |
| 2004/0046128 A1 | 3/2004 | Abel et al. |
| 2004/0147059 A1 | 7/2004 | Jeong et al. |
| 2004/0165080 A1 | 8/2004 | Burks et al. |
| 2004/0197793 A1 | 10/2004 | Hassibi et al. |
| 2004/0206969 A1 | 10/2004 | Orita |
| 2004/0234417 A1 | 11/2004 | Schienle et al. |
| 2004/0249227 A1 | 12/2004 | Klapproth et al. |
| 2005/0014178 A1 | 1/2005 | Holm-Kennedy |
| 2005/0029643 A1 | 2/2005 | Koyanagi |
| 2005/0062864 A1 | 3/2005 | Mabuchi |
| 2005/0121688 A1 | 6/2005 | Nagal et al. |
| 2005/0135974 A1 | 6/2005 | Harvey et al. |
| 2005/0175273 A1 | 8/2005 | Iida et al. |
| 2005/0201899 A1 | 9/2005 | Weisbuch |
| 2005/0206895 A1 | 9/2005 | Salmelainen |
| 2006/0014151 A1 | 1/2006 | Ogura et al. |
| 2006/0051244 A1 | 3/2006 | Lehmann et al. |
| 2006/0060766 A1 | 3/2006 | Turner et al. |
| 2006/0084069 A1 | 4/2006 | Chan et al. |
| 2006/0088818 A1 | 4/2006 | Beynon et al. |
| 2006/0098927 A1 | 5/2006 | Schmidt et al. |
| 2006/0103850 A1 | 5/2006 | Alphonse et al. |
| 2006/0182716 A1 | 8/2006 | Hong et al. |
| 2006/0183145 A1 | 8/2006 | Turner |
| 2006/0199193 A1 | 9/2006 | Koo et al. |
| 2006/0249765 A1 | 11/2006 | Hsieh |
| 2006/0252070 A1 | 11/2006 | Boege et al. |
| 2006/0273245 A1 | 12/2006 | Kim et al. |
| 2006/0278948 A1 | 12/2006 | Yamaguchi et al. |
| 2007/0036511 A1 | 2/2007 | Lundquist et al. |
| 2007/0099212 A1 | 5/2007 | Harris |
| 2007/0116607 A1 | 5/2007 | Wang et al. |
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2007/0279631 A1 | 12/2007 | Yershov |
| 2008/0013877 A1 | 1/2008 | Schmidt et al. |
| 2008/0020938 A1 | 1/2008 | Kaplan |
| 2008/0037008 A1 | 2/2008 | Shepard et al. |
| 2008/0039339 A1 | 2/2008 | Hassibi |
| 2008/0062290 A1 | 3/2008 | Lahav et al. |
| 2008/0081769 A1 | 4/2008 | Hassibi |
| 2008/0117421 A1 | 5/2008 | Yamaguchi et al. |
| 2008/0121045 A1 | 5/2008 | Cole et al. |
| 2008/0145278 A1 | 6/2008 | Korlach |
| 2008/0152280 A1 | 6/2008 | Lundquist |
| 2008/0161195 A1 | 7/2008 | Turner et al. |
| 2008/0199932 A1 | 8/2008 | Hanzel et al. |
| 2008/0212960 A1 | 9/2008 | Lundquist |
| 2008/0220537 A1 | 9/2008 | Foquet |
| 2008/0241866 A1 | 10/2008 | Korlach et al. |
| 2008/0260577 A1 | 10/2008 | Shirai et al. |
| 2008/0304522 A1 | 12/2008 | Mills |
| 2008/0308888 A1 | 12/2008 | Lee |
| 2009/0111207 A1 | 4/2009 | Choumane et al. |
| 2009/0139576 A1 | 6/2009 | Crenshaw |
| 2009/0146076 A1 | 6/2009 | Chiou et al. |
| 2009/0181396 A1 | 7/2009 | Luong et al. |
| 2009/0195784 A1 | 8/2009 | Ogura et al. |
| 2009/0247414 A1 | 10/2009 | Obradovic et al. |
| 2009/0253130 A1 | 10/2009 | Yoo et al. |
| 2009/0263912 A1 | 10/2009 | Yang et al. |
| 2009/0296188 A1 | 12/2009 | Jain et al. |
| 2009/0311774 A1 | 12/2009 | Chiou et al. |
| 2009/0323014 A1 | 12/2009 | Cunningham et al. |
| 2010/0009872 A1 | 1/2010 | Eid et al. |
| 2010/0065726 A1 | 3/2010 | Zhong et al. |
| 2010/0111475 A1 | 5/2010 | Lu et al. |
| 2010/0121582 A1 | 5/2010 | Pan et al. |
| 2010/0243880 A1 | 9/2010 | Makarov |
| 2010/0256918 A1 | 10/2010 | Chen et al. |
| 2011/0024616 A1 | 2/2011 | Pringle |
| 2011/0117637 A1 | 5/2011 | Gray et al. |
| 2011/0183320 A1 | 7/2011 | Flusberg et al. |
| 2011/0201099 A1 | 8/2011 | Anderson et al. |
| 2011/0210094 A1 | 9/2011 | Gray et al. |
| 2012/0014837 A1 | 1/2012 | Fehr et al. |
| 2012/0156577 A1 | 6/2012 | Bulovic et al. |

FOREIGN PATENT DOCUMENTS

| | | |
|---|---|---|
| EP | 1105529 B1 | 11/2005 |
| EP | 1871902 B1 | 10/2006 |
| EP | 2362209 A2 | 8/2011 |
| KR | 10-2005-0088782 A | 9/2005 |
| WO | WO 1990/00632 A1 | 1/1990 |
| WO | WO 1991/006678 A1 | 5/1991 |
| WO | WO 2001/003833 A1 | 1/2001 |
| WO | WO 2001/016375 A2 | 3/2001 |
| WO | WO 2001/063260 A1 | 8/2001 |
| WO | WO 2002/016912 A1 | 2/2002 |
| WO | WO 2004/100068 A2 | 11/2004 |
| WO | WO 2006/116726 A2 | 2/2006 |
| WO | WO 2006/135782 A2 | 12/2006 |
| WO | WO 2007/002367 A2 | 1/2007 |
| WO | WO 2007/011549 A1 | 1/2007 |
| WO | WO 2007/045755 A1 | 4/2007 |
| WO | WO 2008/002765 A2 | 1/2008 |
| WO | WO 2009/001988 A1 | 12/2008 |
| WO | WO 2009/056065 A1 | 5/2009 |
| WO | WO 2009/103339 A1 | 8/2009 |
| WO | WO 2009/131535 A1 | 10/2009 |
| WO | WO 2009/149125 A2 | 12/2009 |
| WO | WO 2010/009543 A1 | 1/2010 |
| WO | WO 2010/051773 A1 | 5/2010 |
| WO | WO 2010/102567 A1 | 9/2010 |
| WO | WO 2010/115147 A2 | 10/2010 |
| WO | WO 2011/076132 A2 | 6/2011 |

OTHER PUBLICATIONS

Boiarski et al., "Integrated-optic sensor with macro-flow cell" Proc. SPIE (1992) 1793:199-211.

Braslavsky, I., et al., "Sequence Information can be Obtained from Single DNA Molecules", PNAS, v. 100, No. 7, p. 3960-3964, Apr. 1, 2003.

(56) References Cited

OTHER PUBLICATIONS

Budach et al., "Planar waveguides as high-performance sensing platforms for fluorescence-based multiplexed oligonucleotide hybridization assays" Anal. Chem. (1999) 71(16):3347-3355.

Cottier et al., "Thickness-modulated waveguides for integrated optical sensing" Proc. SPIE (2002) 4616:53-63.

Deopura, M. et al., "Dielectric omnidirectional visible reflector" Optics Lett (2001) 26(15):1197-1199.

Duveneck et al., "Planar waveguides for ultra-high sensitivity of the analysis of nucleic acids" Anal Chem Acta (2002) 469:49-61.

Eid, J., et al., "Real-Time DNA Sequencing from Single Polymerase Molecules," Science, vol. 323, p. 133-138 (Jan. 2, 2009).

Feldstein et al., "Array Biosensor: optical and fluidics systems" J. Biomed Microdev. (1999) 1:139-153.

Fink, Y. et al., "A dielectric omnidirectional reflector" Science (1998) 282:1679-1682.

Gupta, P. "Single-Molecule DNA Sequencing Technologies for Future Genomics Research," Trends in Biotechnology, vol. 26, No. 11, p. 602-611.

Herron et al., "Orientation and Activity of Immobilized Antibodies" Biopolymers at Interfaces 2nd Ed (2003) Surfactant Science Series vol. 110, Marcel Dekker, NY pp. 115-163.

Kumbhakar, M. "Single-Molecule Detection in Exploring Nanoenvironments: an Overview," J. of Photochemistry and Photobiology, n. 5, p. 113-137 (2004).

Levene, M.J. et al., "Zero-mode waveguides for single-molecule analysis at high concentrations" Science (2003) 299:682-686.

Ottesen et al., "Microfluidic Digital PCR Enables Multigene Analysis of Individual Environmental Bacteria," Science, 2006, v. 314, p. 1464.

Psaltis, Demetri, et al., "Developing Optofluidic Technology through the Fusion of Microfluidics and Optics," Nature, v. 442, p. 381-386, Jul. 27, 2006.

Salama et al., "Modeling and simulations of luminescence detection platforms" Biosensors & Bioelectronics (2004) 19:1377-1386.

Sauer, et al., Single Molecule DNA Sequencing in Submicrometer Channels: State of the Art and Future Prospects.

Wang, et al., "Generation of Radially and Azimuthally Polarized Light by Optical Transmission Through Concentric Circular Nanoslits in AG Films," Optics Express, 2010, vol. 18, issue 1, 63-71.

Weissman et al., "Mach-Zhnder type, evanescent-wave bio-sensor, in ion-exchanged glass, using periodically segmented waveguide" Proc. Spie (1999) 3596:210-216.

Wu et al., "DNA and protein microarray printing on silicon nitride waveguide surfaces" Biosensors and Bioelectronics (2006) 21:1252-1263.

Yariv, A. et al., "Periodic structures for integrated optics" IEEE J Quantum Elec (1977) QE-13(4):233-253.

Yang, R., et al., "An Integrated Micro Optical and Micro Fluidic System for Micro-Total Analysis System", Proc. of SPIE, v. 4177, Aug. 18, 2000.

side view top view planar oxide conformal

CMP

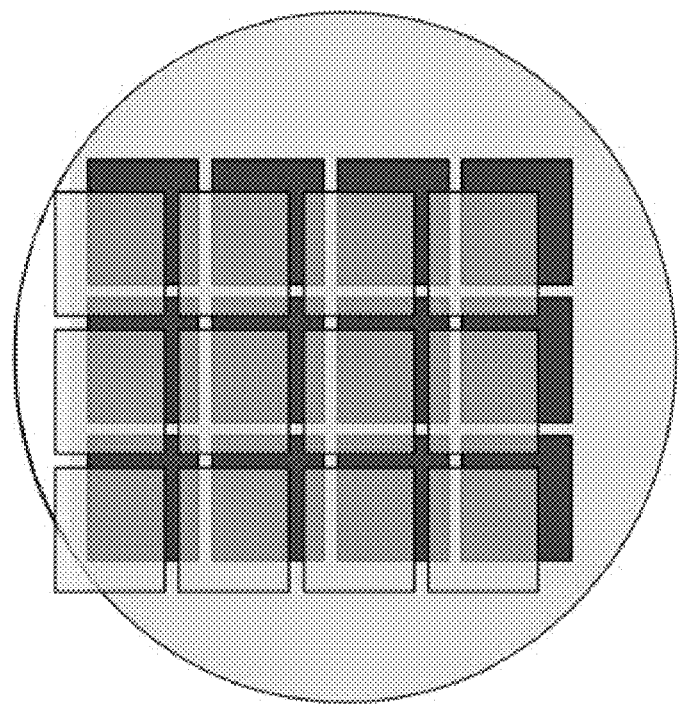
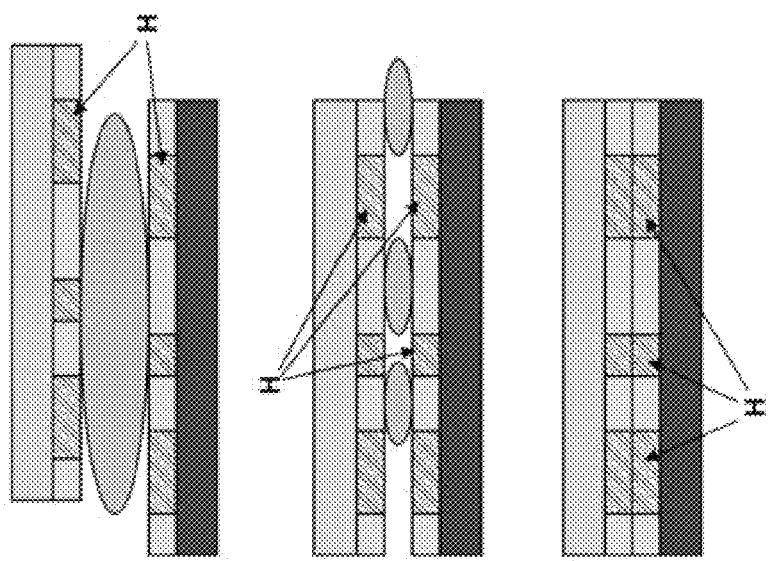
FIG. 18D
FIG. 18A
FIG. 18B
FIG. 18C

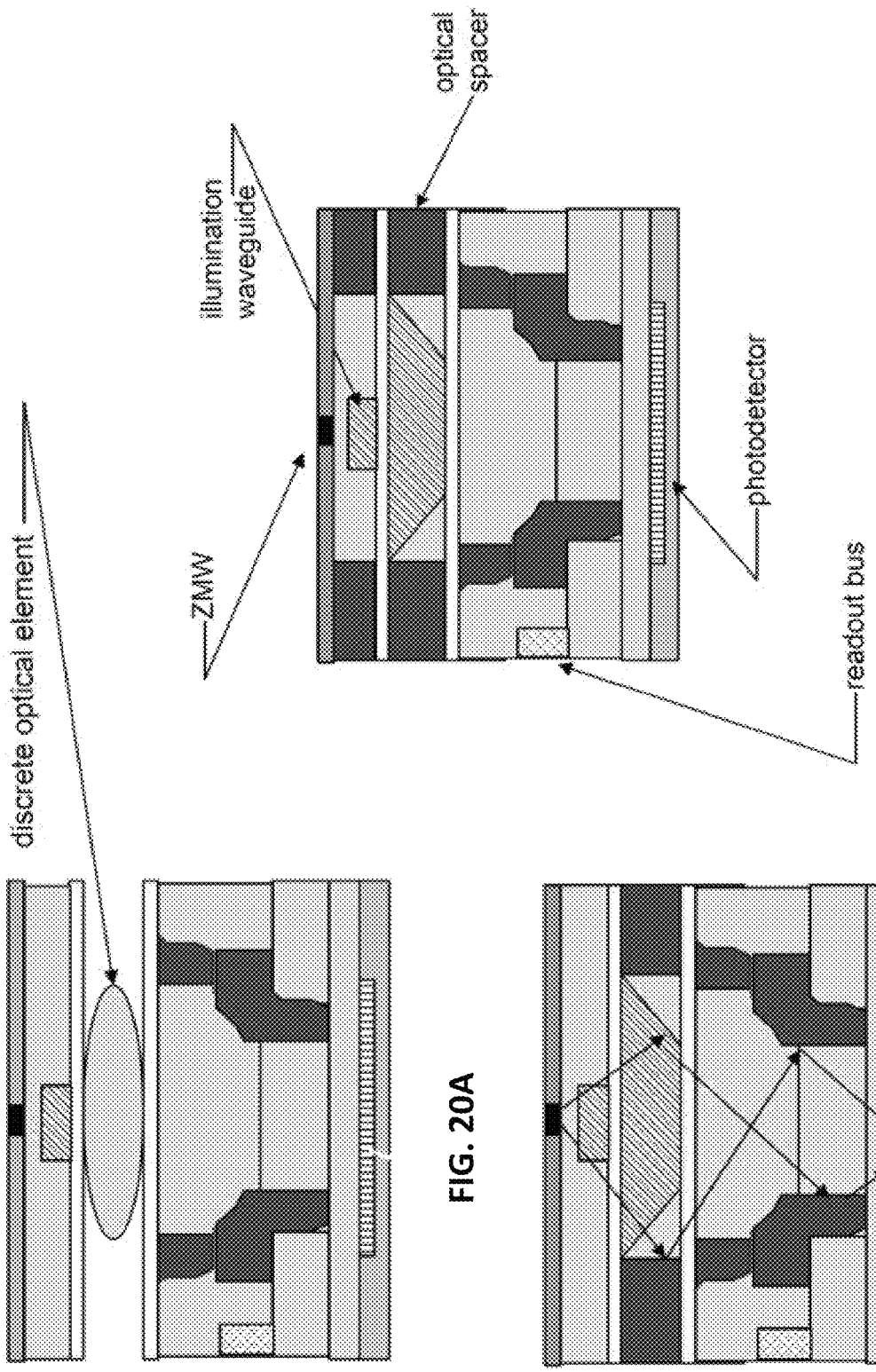

Example of a compact CMOS mixer circuit suitable for pixel implementation (5)
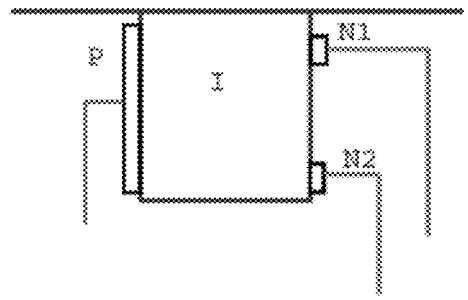
(5.1)
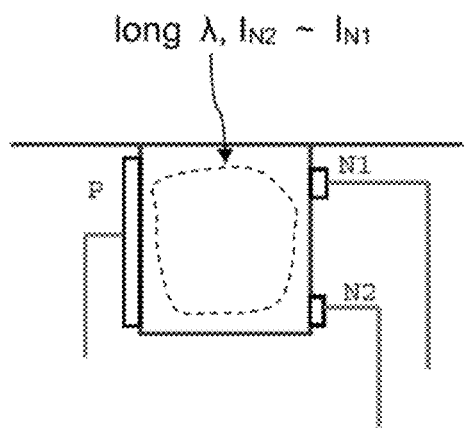
long λ, $I_{N2} \sim I_{N1}$
(5.2)
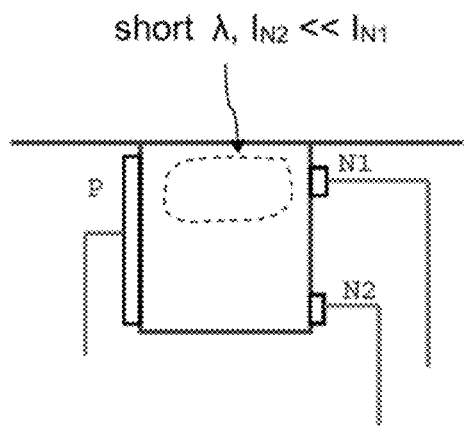
short λ, $I_{N2} \ll I_{N1}$
FIG. 29

OPTICS COLLECTION AND DETECTION SYSTEM AND METHOD

CROSS-REFERENCE TO RELATED APPLICATIONS

This application is a continuation of U.S. application Ser. No. 15/195,493 filed Jun. 28, 2016, which is a continuation of U.S. application Ser. No. 13/031,146 filed Feb. 18, 2011, which claims priority to U.S. Provisional Application No. 61/306,235 filed Feb. 19, 2010, U.S. Provisional Application No. 61/387,916 filed Sep. 29, 2010, and U.S. Provisional Application No. 61/410,189 filed Nov. 4, 2010, the entire contents of which are incorporated herein for all purposes by this reference.

BACKGROUND OF THE INVENTION

Field of the Invention

This invention relates to optics collection and detection systems and methods for their use.

Description of Related Art

A large number of systems for optical analysis of samples or materials employ complex optical trains that direct, focus, filter, split, separate and detect light to and/or from the sample materials. Such systems typically employ an assortment of different optical elements to direct, modify, and otherwise manipulate light directed to and/or received from a reaction site.

Conventional optical systems typically are complex and costly. The systems also tend to have significant space requirements. For example, typical systems employ mirrors and prisms in directing light (e.g. laser light) from its source to a desired destination for detection. Additionally, such systems may include light splitting optics such as beam splitting prisms to generate two beams from a single original beam. In the case of modern analysis systems, there is a continuing need for systems with very high throughput and portability.

There is a continuing need for optical systems for collecting and detecting excitation signals. For example, analytical systems for monitoring processes at the single molecule level show great promise but require the collection and detection of small levels of illumination. There is a need for collecting and detecting optical signals, and specifically for collection and detection systems with reduced noise and improved performance.

There is a continuing need to improve upon the functionality, footprint and cost of systems for optical analysis. The present invention provides devices, systems, and methods for overcoming the above problems in addition to other benefits.

BRIEF SUMMARY

One aspect of the present invention is directed to an integrated device for measuring optical signals from an array of optical sources over time. The device may include an array of elements, each having a top layer comprising an optical source that emits two or more optical signals, each optical signal comprising different wavelengths, a middle layer comprising a spectral diversion element, and a bottom layer comprising a detector sensitive to spatial distributions of light. Each spectral diversion element may divert each of the two or more optical signals onto different regions of the bottom layer, whereby the identity of the optical signal can be identified by the relative spatial light intensity across the detector.

The optical source may include a zero mode waveguide and the optical signals may be emitted from fluorescent labels corresponding to a chemical or biochemical reaction occurring within the zero mode waveguide. The chemical or biochemical reaction may include nucleic acid synthesis. The spectral diversion element may include an optical grating or holographic element. The spectral diversion element may include a Bragg grating disposed at an angle to the normal to the central ray of the emitted light. The pixels may be in a linear array. The pixels may be in a two dimensional array. The four different optical signals may be emitted from each optical source. The detector has four pixels, each corresponding to one of the four optical signals whereby the spectral diversion element diverts each of the colors to a different element. The spectral diversion element may include a lens. The lens may be cylindrically symmetrical and diverts different wavelengths of light at different angles from the center of the lens resulting in a circularly symmetric pattern on the detector for each set of wavelengths. The detector may include one central pixel and one or more pixels comprising a circular ring around the central pixel.

Another aspect of the present invention is directed to a pixel including a photodiode having at least a first and a second transfer gate, wherein the pixel may be configured such that the photodiode sends charge to one transfer gate for a first period of time, then send charge to a second transfer gate for a second period of time before the remaining charge from the pixel is unloaded.

The pixel further may include a third transfer gate and a fourth transfer gate wherein after the second period of time, charge may be sent to the third transfer gate for a third period of time, then charge may be sent to the fourth transfer gate for a fourth period of time before the charge from the pixel is unloaded.

Another aspect of the present invention is directed to a system including an excitation light source that emits a first wavelength range for a first excitation time, then emits a second wavelength range for a second excitation time, the excitation light source providing excitation light to a sample, the sample having a first fluorophore that is excited by the first wavelength range, and a second fluorophore that is excited by the second wavelength range, and a pixel comprising a photodiode having at least a first transfer gate and a second transfer gate, wherein the pixel is configured such that the photodiode sends charge to the first transfer gate for a first collection time, then send charge to the second transfer gate for a collection time before the charge from the pixel is unloaded. The system may be configured such that the first excitation time corresponds to the first collection time and the second excitation time correlates to the second collection time, whereby the emission from the first fluorophore can be distinguished from the emission from the second fluorophore.

The light source may further emit a third wavelength range for a third excitation time, then emit a fourth wavelength range for a fourth excitation time, wherein the sample further may include a third fluorophore that is excited by the third wavelength range, and a fourth fluorophore that is excited by the fourth wavelength range, and the photodiode further may include a third transfer gate and a fourth transfer gate. The pixel may be configured such that the photodiode sends charge to the third transfer gate for a third collection time, then send charge to the fourth transfer gate for a collection time before the charge from the pixel is unloaded. The system may further be configured such that the third excitation time corresponds to the third collection time and the fourth excitation time correlates to the fourth collection time, whereby the emission of each of the four fluorophores can be distinguished. The excitation light may include a first laser that emits the first wavelength range and a second laser that emits the second wavelength range, a third laser that emits the third wavelength range, and a fourth laser that emits a fourth wavelength range.

Yet another aspect of the present invention is directed to a method including illuminating a sample with a first wavelength range for a first excitation time, then illuminating the sample with a second wavelength range for a second excitation time, wherein the sample may include a first fluorophore that is excited by the first wavelength range, and a second fluorophore that is excited by the second wavelength range, and directing emitted light from the sample to a single pixel that measures light for a first collection time and then measures light for a second collection time, such that the pixel separately stores charge related to each of the collection times whereby the charge related to each of the collection times can be separately read out, wherein the first excitation time corresponds to the first collection time and the second excitation time correlates to the second collection time, whereby the emission from the first fluorophore can be distinguished from the emission from the second fluorophore.

A further aspect of the present invention is directed to an integrated device for measuring optical signals from an array of optical sources over time. The device may include an array of elements, each element having a top layer comprising an optical source that emits two or more optical signals, each optical signal having a different rate of signal decay, a middle layer capable of transferring light from the top layer to the bottom layer, and a bottom layer comprising a detector having a single pixel. The pixel may measure the characteristic photonic emission lifetime of each of the two or more different optical signals, allowing the pixel to distinguish the identity of each of the optical signals.

At least one of said optical sources may include a zero mode waveguide. At least one of said optical sources may include a chemical or biochemical reaction, and the two or more optical signals may be from fluorescent labels whose fluorescence is indicative of the occurrence of that reaction.

Still a further aspect of the present invention is directed to an integrated device for measuring optical signals from an array of optical sources over time, the device comprising an array of elements, each element including a top layer comprising an optical source that emits two or more optical signals, each optical signal having a different rate of signal decay, a middle layer capable of transferring light from the top layer to the bottom layer, and a bottom layer comprising a detector having a single pixel. The pixel may measure the characteristic absorption depth of each of the two or more different optical signals, allowing the pixel to distinguish the identity of each of the optical signals.

The optical source may include a zero mode waveguide. The optical source may include a chemical or biochemical reaction, and the two or more optical signals may be from fluorescent labels whose fluorescence is indicative of the occurrence of that reaction. The pixel may be a stacked diode. The detector may include multiple proximal pixels. The detector may include a single position sensitive pixel or a position sensitive diode.

Yet another aspect of the present invention is directed to an optics collection and detection system including a reaction cell, an illumination light source providing illumination light to the reaction cell at a first wavelength $\lambda 1$, a detector for detecting excitation light at a second wavelength $\lambda 2$, and a photon band gap (PBG) layer disposed between the reaction cell and the detector, wherein the PBG layer rejects light at the first wavelength $\lambda 1$ but allows light at the second wavelength $\lambda 2$ travel toward the detector.

The optics collection and detection system may further include a plurality of detectors for detecting excitation light, wherein one of said detectors detects light at the second wavelength $\lambda 2$, and another of said detectors detects light at a third wavelength $\lambda 3$, a plurality of PBG stacks, each disposed between the PBG layer and a respective detector, wherein one of said PBG stacks rejects light at the third wavelength $\lambda 3$ but allows light at the second wavelength $\lambda 2$ to travel toward said one detector, and wherein another of said PBG stacks allows light at the second wavelength $\lambda 2$ but allows light at the third wavelength $\lambda 3$ to travel toward said other detector. The system may include four detectors, each formed by a sensor quadrant of a quad photodiode (QPD), and four PBG stacks, wherein each PBG stack may be optically aligned with a respective sensor quadrant. Each detector may be formed by a respective region of a PIN diode. The optics collection and detection system may further include a doped region in which a heavy metal or a semiconductor is doped into fused silica or silicon oxide adjacent the reaction cell to provide an index of refraction gradient to disperse emission light at different angles leaving the reaction cell.

Yet another aspect of the present invention is directed to a method of fabricating optics collection and detection system including providing a substrate, applying a first lithographic protection mask to form a protective dome (PD), applying an anisotropic etch to form a hemispherical cavity, applying thin film deposition to form a filter, applying a second lithographic protection mask to protect the hemispherical cavity, applying a planarization layer, applying a top layer, and etching the top layer to form a reaction cell above the hemispherical cavity. A hemispherical filter may be formed adjacent a bottom surface of the reaction cell.

And yet another aspect of the present invention is directed to a method of DNA sequencing including affixing a polymerase to a photodiode, labeling a nucleotide with a metal nanoparticle, exciting a plasmon resonance in the metal nanoparticles, and monitoring the level of baseline current in the photodiode.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

BRIEF DESCRIPTION OF THE DRAWINGS

FIG. 18A to FIG. 18D is a schematic sequence illustrating an exemplary method of fabricating an analytic device, along with a plan view thereof, suitable for use in the system of FIG. 1.

FIG. 20A to FIG. 20C are schematic representations illustrating an exemplary analytic device suitable for use in the system of FIG. 1.

FIG. 29 is a schematic representation of the operation of an exemplary detector suitable for use in the system of FIG. 1.

DETAILED DESCRIPTION

Figure 1:
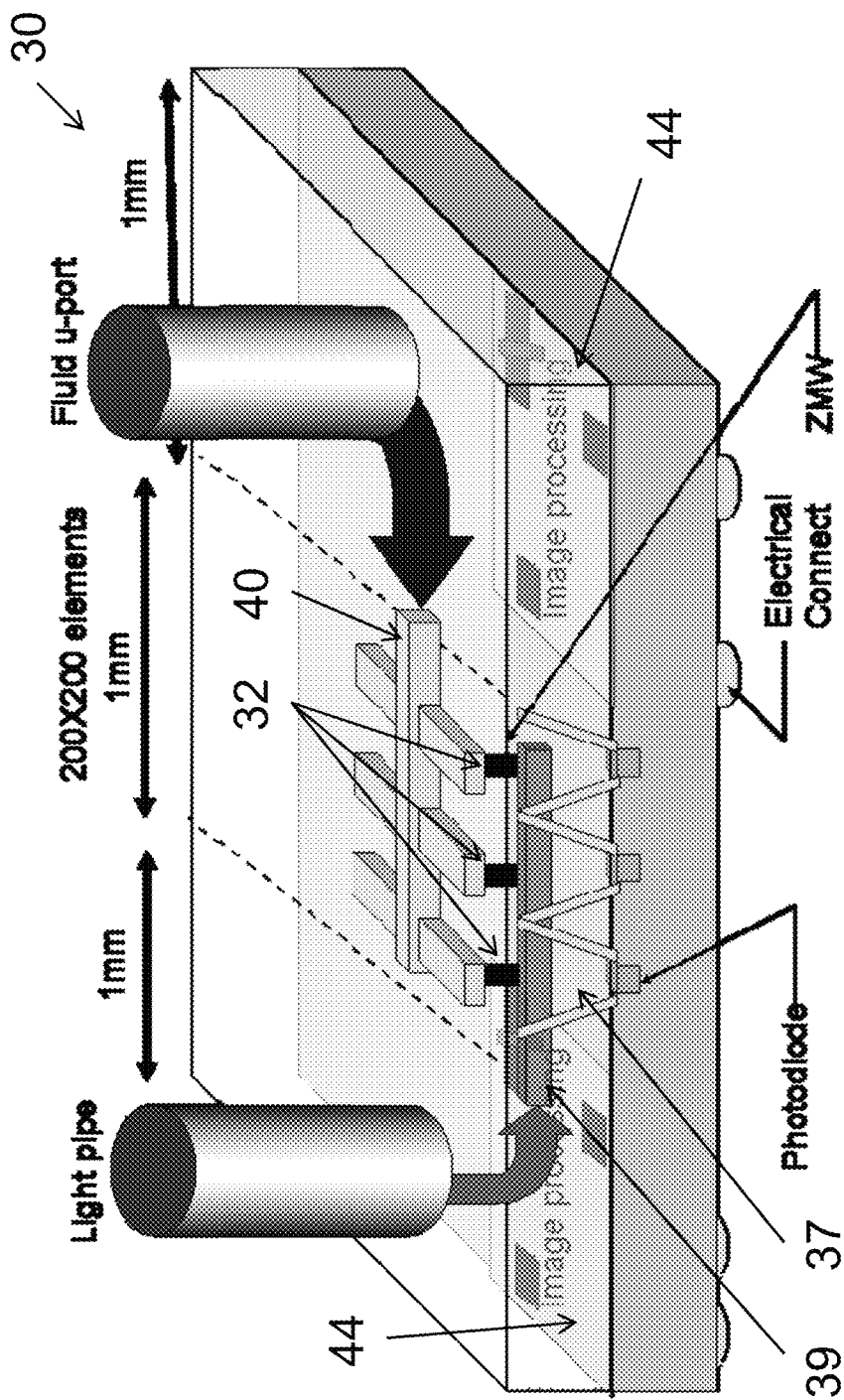
FIG. 1 is a schematic view of an exemplary optics collection and detection system and method in accordance with various aspects of the present invention.

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

The present invention is generally directed to improved systems, methods and devices for use in optical analyses, and particularly, optical analyses of biological and/or chemical samples and reactions.

Various aspects of the systems and methods described herein are similar to those described in U.S. Provisional Patent Application No. 61/306,235 entitled INTEGRATED ANALYTICAL DEVICES AND SYSTEMS, U.S. Provisional Patent Application No. 61/387,916, entitled INTEGRATED ANALYTICAL SYSTEM AND METHOD, U.S. Provisional Patent Application No. 61/410,189, entitled ILLUMINATION OF INTEGRATED ANALYTICAL SYSTEMS, the entire content of which is incorporated herein for all purposes by this reference.

In various respects, the optical analyses of the invention generally seek to gather and detect one or more optical signals, the appearance or disappearance of which, or localization of which, is indicative of a given chemical or biological reaction and/or the presence or absence of a given substance within a sample material. In some cases, the reactants, their products, or substance of interest (all of which are referred to as reactants herein) inherently present an optically detectable signal which can be detected. In other cases, reactants are provided with exogenous labeling groups to facilitate their detection. Useful labeling groups include fluorescent labels, luminescent labels, mass labels, light scattering labels, electrochemical labels (e.g., carrying large charge groups), metal labels, and the like. Exemplars of such labeling groups are disclosed by U.S. Pat. No. 7,332,284 and U.S. Patent Application Publication Nos. US 2009/0233302 A1, US 2008/0241866 A1, and US 2010/0167299 A1, the entire content of which is incorporated herein for all purposes by this reference.

In various embodiments, one or more reactants in an analysis is provided with a fluorescent labeling group that possesses a fluorescent emission spectrum that is shifted from its excitation spectrum, allowing discrimination between the excitation light source and the emission of the label group. These fluorescent labels typically have high quantum yields, further enhancing their detectability. A variety of different fluorescent label groups are well known in the art, and include fluorescein and rhodamine based organic dyes, such as those sold under the Cy3 and Cy5 labels from, e.g., GE Healthcare, and the AlexaFluor® dyes available from Life Technologies, Inc. A wide variety of organic dye structures have been previously described in the art.

Other fluorescent label groups include, for example, particle-based labeling groups. Some such particle label groups constitute encapsulated or otherwise entrained organic fluorophores, while others comprise fluorescent nanoparticles, such as inorganic semiconductor nanocrystals, e.g., as described in U.S. Pat. Nos. 6,207,392, 6,225,198, 6,251,303, 6,501,091, and 7,566,476, the entire content of which is incorporated herein for all purposes by this reference.

By detecting these fluorescent labeling groups, one can ascertain the localization of a given labeled reactant, or detect reaction events that result in changes in the spectral or other aspects of the fluorescently labeled reactant. For example, in binding or hybridization reactions, the ability of a labeled reactant to bind to another immobilized reactant is detected by contacting the reactants, washing unbound labeled reactant away, and observing the immobilized reactant to look for the presence of bound fluorescent label. Such assays are routinely employed in hybridization assays, antibody assays, and a variety of other analyses.

In a number of different nucleic acid sequencing analyses, fluorescently-labeled nucleotides are used to monitor the polymerase-mediated, template-dependent incorporation of nucleotides in a primer extension reaction. In particular, a labeled nucleotide is introduced to a primer template polymerase complex, and incorporation of the labeled nucleotide is detected. If a labeled nucleotide is incorporated, it is indicative of the underlying and complementary nucleotide in the sequence of the template molecule. In traditional Sanger sequencing processes, the detection of incorporation of labeled nucleotides utilizes a termination reaction where the labeled nucleotides carry a terminating group that blocks further extension of the primer. By mixing the labeled terminated nucleotides with unlabeled native nucleotides, one generates nested sets of fragments that terminate at different nucleotides. These fragments are then separated by capillary electrophoresis, to separate those fragments that differ by a single nucleotide, and the labels for the fragments are read in order of increasing fragment size to provide the sequence (as provided by the last-added, labeled terminated nucleotide). By providing a different fluorescent label on each of the types of nucleotides that are added, one can readily differentiate the different nucleotides in the sequence (see, e.g., U.S. Pat. No. 5,821,058, the entire content of which is incorporated herein for all purposes by this reference).

In newer generation sequencing technologies, arrays of primer-template complexes are immobilized on surfaces of substrates such that individual molecules or individual and homogeneous groups of molecules are spatially discrete from other individual molecules or groups of molecules, respectively. Labeled nucleotides are added in a manner that results in a single nucleotide being added to each individual molecule or group of molecules. Following the addition of the nucleotide, the labeled addition is detected and identified.

In some cases, the processes utilize the addition of a single type of nucleotide at a time, followed by a washing step. The labeled nucleotides that are added are then detected, their labels removed, and the process repeated with a different nucleotide type. Sequences of individual template sequences are determined by the order of appearance of the labels at given locations on the substrate.

In other similar cases, the immobilized complexes are contacted with all four types of labeled nucleotides where each type bears a distinguishable fluorescent label and a terminator group that prevents the addition of more than one nucleotide in a given step. Following the single incorporation in each individual template sequence (or group of template sequences,) the unbound nucleotides are washed away, and the immobilized complexes are scanned to identify which nucleotide was added at each location. Repeating the process yields sequence information of each of the template sequences. In other cases, more than four types of labeled nucleotides are utilized.

In particularly elegant approaches, labeled nucleotides are detected during the incorporation process, in real time, by individual molecular complexes. Such methods are described, for example, in U.S. Pat. No. 7,056,661, the entire content of which is incorporated herein for all purposes by this reference. In these processes, nucleotides are labeled on a terminal phosphate group that is released during the incorporation process so as to avoid accumulation of label on the extension product and avoid any need for label removal processes that can be deleterious to the complexes. Primer/template polymerase complexes are observed during the polymerization process, and nucleotides being added are detected by virtue of their associated labels. In one particular aspect, they are observed using an optically confined structure, such as a zero mode waveguide (see, e.g., U.S. Pat. No. 6,917,726, the entire contents of which is incorporated herein for all purposes by this reference) that limits exposure of the excitation radiation to the volume immediately surrounding an individual complex. As a result, only labeled nucleotides that are in the process of being incorporated are exposed to excitation illumination for a time that is sufficient to identify the nucleotide. In another approach, the label on the nucleotide is configured to interact with a complementary group on or near the complex, e.g., attached to the polymerase, where the interaction provides a unique signal. For example, a polymerase may be provided with a donor fluorophore that is excited at a first wavelength and emits at a second wavelength, while the nucleotide to be added is labeled with a fluorophore that is excited at the second wavelength but emits at a third wavelength (see, e.g., the above-mentioned '661 patent). As a result, when the nucleotide and polymerase are sufficiently proximal to each other to permit energy transfer from the donor fluorophore to the label on the nucleotide, a distinctive signal is produced. Again, in these cases, the various types of nucleotides are provided with distinctive fluorescent labels that permit their identification by the spectral or other fluorescent signature of their labels.

As will be appreciated, a wide variety of analytical operations may be performed using the overall reaction framework described herein and are applicable to the present invention. Such reactions include reactive assays, e.g., examining the combination of reactants to monitor the rate of production of a product or consumption of a reagent, such as enzyme reactions, catalyst reactions, etc. Likewise, associative or binding reactions may be monitored where one is looking for specific association between two or more reactants, such as nucleic acid hybridization assays, antibody/antigen assays, coupling or cleavage assays, and the like.

The analytical system in accordance with the present invention employs one or more analytical devices referred to as "optode" elements. In an exemplary embodiment, the system includes an array of analytical devices formed as a single integrated device. An exemplar of a suitable optode element is disclosed by the above-mentioned '235 application. The exemplary array is configured for single use as a consumable. In various embodiments, the optode element includes other components including, but not limited to, local fluidics, electrical connections, a power source, illumination elements, detector elements, logic, and a processing circuit. Each analytical device or array is configured for performing an analytical operation as described above.

Turning now to the drawings, wherein like components are designated by like reference numerals throughout the various figures, attention is directed to FIG. 1 which shows a optics collection and detection system, generally designated 30 which generally includes a reaction cell 32, in which the reactants are disposed and from which the detector optical signals emanate.

"Reaction cell" is to be understood as generally used in the analytical and chemical arts and refers to the location where the reaction of interest is occurring. Thus, "reaction cell" may include a fully self-contained reaction well, vessel, flow cell, chamber, or the like, e.g., enclosed by one or more structural barriers, walls, lids, etc., or it may comprise a particular region on a substrate and/or within a given reaction well, vessel, flow cell or the like, e.g., without structural confinement or containment between adjacent reaction cells. The reaction cell may include structural elements to enhance the reaction or its analysis, such as optical confinement structures, nanowells, posts, surface treatments such as hydrophobic or hydrophilic regions, binding regions, or the like. The reaction cell can comprise a nanoscale feature such as a nanoscale well, and can comprise a zero mode waveguide (ZMW) as described in U.S. Pat. No. 7,315,019, the entire content of which is incorporated by reference herein for all purposes.

In various respects, "analytical device" refers to a reaction cell and associated components that are functionally connected. In various respects, "analytical system" refers to one more associated analytical devices and associated components. In various respects, "analytical system" refers to the larger system including the analytical system and other off-chip instruments for performing an analysis operation such as a power source and reservoir.

In some cases, one or more reactants for the reaction of interest may be immobilized, entrained or otherwise localized within a given reaction cell. A wide variety of techniques are available for localization and/or immobilization of reactants including surface immobilization through covalent or non-covalent attachment, bead, or particle-based immobilization, followed by localization of the bead or particle, entrainment in a matrix at a given location, and the like. Reaction cells may include ensembles of molecules, such as solutions or patches of molecules, or it may include individual molecular reaction complexes, e.g., one molecule involved in the reaction of interest as a complex. Similarly, the overall devices and systems of the invention may include individual reaction cells or may comprise collections, arrays, or other groupings of reaction cells in an integrated structure, e.g., a multiwell or multi-cell plate, chip, substrate or system. Some examples of such arrayed reaction cells include nucleic acid array chips, e.g., GeneChip® arrays (Affymetrix, Inc.), zero mode waveguide arrays (as described elsewhere herein), microwell and nanowell plates, multichannel microfluidic devices, e.g., LabChip® devices (Caliper Life Sciences, Inc.), and any of a variety of other reaction cells. In various respects, the "reaction cell", sequencing layer, and zero mode waveguides are similar to those described in U.S. Pat. No. 7,486,865, the entire content of which is incorporated herein for all purposes by this reference.

Although the exemplary analytical system includes an array of analytical devices having a single waveguide layer and reaction cell layer, one will appreciate that a wide variety of layer compositions may be employed in the waveguide array substrate and cladding/reaction cell layer and still achieve the goals of the invention (e.g., U.S. Patent Application Publication No. US 2008/0128627 A1, the entire content of which is incorporated herein for all purposes by this reference).

With continued reference to FIG. 1, analysis system 30 typically includes one or more analytical devices 33 having a detector 35, which is disposed in optical communication with a respective reaction cell 32, that is, the detector element is configured for direct detection of an emission event within respective reaction cell. One will appreciate that such optical communication may include radiative or non-radiative communication. Optical communication between the reaction cell and the detector element may be provided by an optical train or channel 37 which may include one or more optical elements for efficiently directing the signal from reaction cell 32 to detector 35. These optical elements may generally comprise any number of elements, such as lenses, filters, gratings, mirrors, prisms, refractive material, or the like, or various combinations of these, depending upon the specifics of the application. The reagents can be supplied to the reaction cells via a fluid port which is connected to the reaction cells through fluid conduits 40. Typically, the analytical reaction that is measured within the reaction cell can be monitored using fluorescence. The illumination (excitation) light for such fluorescence can be supplied via a light pipe as shown in FIG. 1, via a waveguide 39. The fluid port and light pipe can each be used to address multiple analytical devices or elements at one time.

Figure 2:
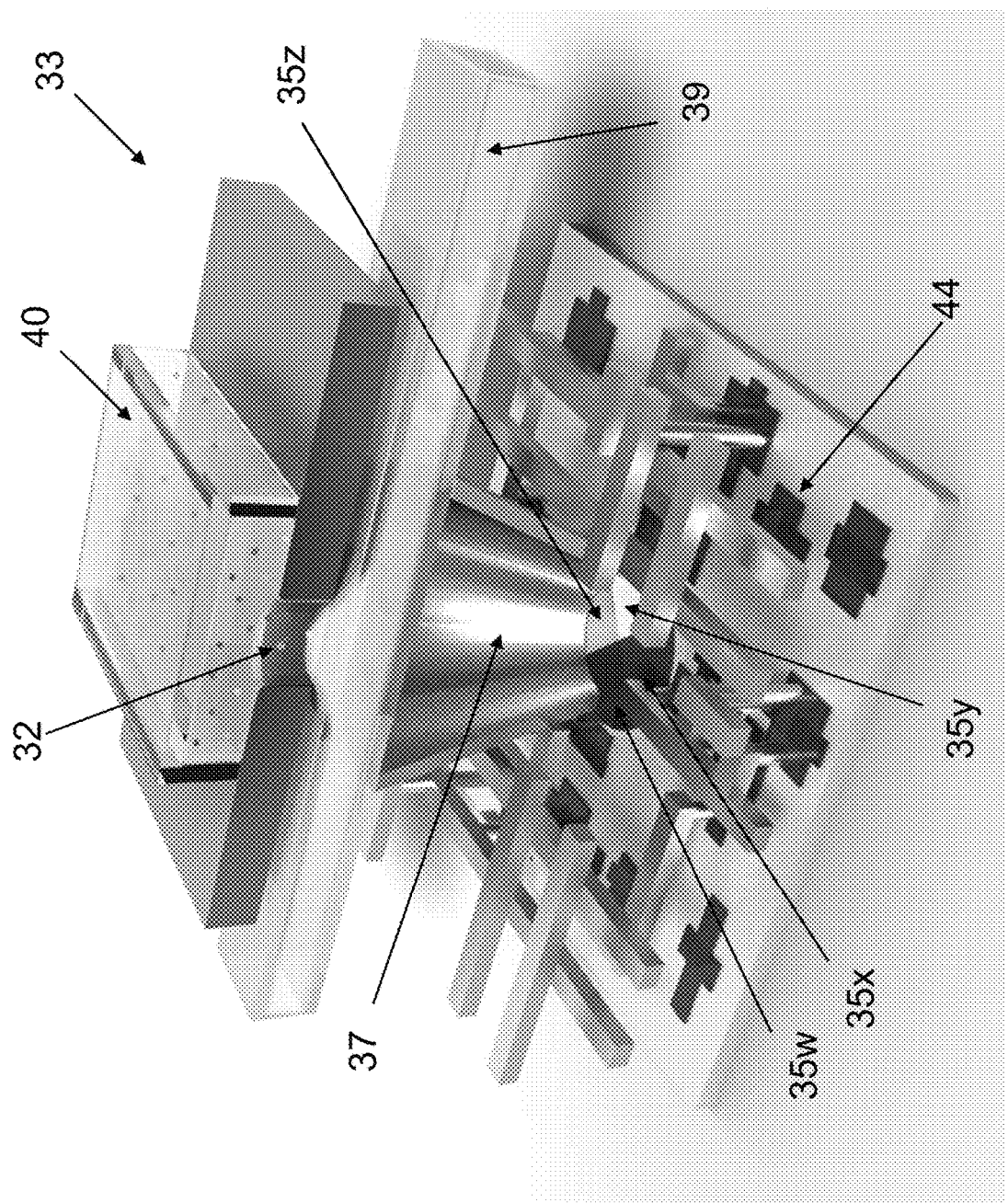
FIG. 2 is a perspective rendering of an exemplary optics collection and detection device of the system of FIG. 1.

In various embodiments, the reaction cell and detector element are provided along with one or more optical elements in an integrated device structure, such as that shown in FIG. 2. By integrating these elements into a single device architecture, one improves the efficiency of the optical coupling between the reaction cell and the detector. In particular, in conventional optical analysis systems, discrete reaction vessels are typically placed into optical instruments that utilize free-space optics to convey the optical signals to and from the reaction vessel and to the detector. These free space optics tend to include higher mass and volume components, and have free space interfaces that contribute to a number of weaknesses for such systems. For example, such systems have a propensity for greater losses given the introduction of unwanted leakage paths from these higher mass components, and typically introduce higher levels of auto-fluorescence, all of which reduce the signal-to-noise ratio (SNR) of the system and reduce its overall sensitivity, which in turn can impact the speed and throughput of the system. Additionally, in multiplexed applications, signals from multiple reaction regions (i.e., multiple reaction cells or multiple reaction locations within individual cells) are typically passed through a common optical train, or common portions of an optical train, using the full volume of the optical elements in that train to be imaged onto the detector plane. As a result, the presence of optical aberrations in these optical components, such as diffraction, scattering, astigmatism, and coma, degrade the signal in both amplitude and across the field of view resulting in greater noise contributions and cross talk among detected signals. Furthermore, these free-space optical systems can be large and bulky.

The devices of the invention, in contrast, include relatively low volumes between the reaction cell and the detector, thereby reducing the noise contributions from those components and provide few or no free space interfaces that can contribute to the noise profile of the system through the introduced reflections and losses from large index changes from the components to air or free space. Further, in preferred aspects, a given reaction region is provided with its own devoted optical train to direct signals to a devoted portion of the sensor. In addition the integrated systems described herein can be made small and compact.

In various embodiments, the device is configured such that emitted light from the fluorescent species in the nanoscale well is not transmitted through free space. By "not transmitted through free space" it is generally meant that the respective element (e.g. a signal or energy) is not transmitted through open space or free space optics, and in various respects, is transmitted only through light-modulating media. Such light-modulating media may include refractive devices such as an optical lens that makes use of the refractive index of a defined volume of air. By contrast, light-modulating media generally does not include ambient air open to the environment.

As a result of the integrated architecture, optical aberrations are confined to individual reaction regions as opposed to being applied across an entire array of reaction regions. Likewise, in a further aspect, the reaction region, optical train, and detector are fabricated in an integrated process, e.g., micromechanical lithographic fabrication processes so that the components are, by virtue of the manufacturing process, pre-aligned and locked into such alignment by virtue of the fabrication process. Such alignment is increasingly difficult using free space optics systems as reaction region sizes decrease and multiplex increases. In addition, by integrating such components into one unified component, relative movement between such sub-components, as is the case with free space optics, can make drift and continued alignment resulting from vibrations a more difficult task. Likewise, the potential for contamination in any of the intermediate spaces (e.g. dust and other contaminants), is eliminated (or at least substantially reduced) in an integrated system as compared to free space systems.

In addition to reducing noise contributions from the optical pathway, the integrated devices of the invention also benefit from fabrication processes and technology that eliminate other issues associated with discrete reaction cell, optic, and detection components. For example, with respect to certain highly multiplexed or arrayed reaction cells, initial alignment and maintaining alignment of the detection with the reaction cell over the full length of the analysis can raise difficulties. This is particularly the case where excitation illumination may be specifically targeted among different array locations of the reaction cell and/or among different reaction cells.

As used herein, the term "integrated" may have different meanings when used to refer to different aspects of the invention. For example, in the case of an integrated device or an integrated optical system, the term "integrated" generally means that the various components are physically connected, and that the optical signals pass from component to component without passing into air or free space, as would be understood by one in the field of optics. In the context of the description of a system, the term "integrated" is to be understood as generally used in the analytical and electrical engineering fields, where "integrated" would refer, for example, to a combination or coordination of otherwise different elements to provide a harmonious and interrelated whole, whether physically or functionally. The meaning of the term will generally be understood by one of skill in the art by the context in which it is used.

With continued reference to FIG. 2, being an integrated device, the light emitted from the reactor cell 32 will pass through to detector 35 without passing through air or free space. In some embodiments, the integrated analytical device also comprises components for providing illumination to the reactor cell. For example, in many cases where the reactor cell includes a zero mode waveguide, it is often desirable to provide illumination from below the reactor cell, for example between the bottom of reactor cell and the transmission layer or optical train 37. In some cases, a waveguide 39 is incorporated into the analytical device to provide such illumination. Analytical devices comprising waveguides for illumination are described in more detail herein, and for example, in U.S. Pat. No. 7,820,983 and U.S. Patent Application Publication No. US 2010/0065726 A1, the entire content of which is incorporated herein for all purposes by this reference.

In various embodiments, the analytical device is a substrate including a reaction cell array, and a detector array on a bottom surface of the array. The device may also include other components such as processing circuits, optical guides, and processing circuits. In various embodiments, the analytical device may be formed by building layers on a substrate or by bonding two or more substrates. In an exemplary device, a fused silicon (FuSi) substrate, a zero-mode waveguide (ZMW) layer, and a silicon substrate with a photodetector array are bonded together to form the array of analytical devices, such as the ones described in the above-mentioned '189 and '916 applications. One will appreciate that such integrated analytical devices have significant advantages in terms of alignment and light collection. For example, the reaction site and detector are aligned through the manufacturing process. One will appreciate from the description herein, that any of the components and systems may be integrated or modified in various ways. In another example, the ZMW substrate and detector array are on separate substrates that are brought together for the experiment, after which the ZMW substrate is replaced with another substrate for a second experiment. With this approach, the detector array may be re-used rather than being disposed with the ZMW substrate after an experiment. It may also be more cost effective as the yields from each of the processes are separated. In this manner, the ZMW array and detector array are in intimate contact during the experiment (as if they are part of an integrated device), but they can be separated after the measurement.

The size of the processing circuits in each of the analytical devices may be minimized to reduce costs. By developing a board in the receiver camera electronics (e.g. massively parallel DSP or microprocessor or a dedicated FPGA, CPLD or ASIC), overall operating costs (i.e. $/mega-base) may be minimized.

With further reference to FIG. 2, analytical device 33 has a reaction cell 32 that is coupled with a reagent reservoir by fluid conduit 40 which delivers reactants to the reaction cell. The reaction cell can be a nanoscale well or zero mode waveguide. In some cases, the reaction cell will have a biomolecule such as a polymerase enzyme immobilized within it. The fluidic conduit can provide reagents across a number of reaction cells. Below the reaction cell is a waveguide for providing excitation illumination to the reagents within the reaction cell. While a waveguide is shown here, other optical elements such as those provided elsewhere herein can be used to provide light from under the reaction cell. The illumination light can be used to excite fluorescent emission from reagents with the reactor cell. The light emitted from the reaction cell is directed downward through a transmission layer, which acts to transmit the light from the reaction cell to the detector. In some cases, the transmission layer will have optical components to enhance the efficiency of the light transfer or modulate the light.

In the analytical device of FIG. 2, optical conduit or optical train 37 is in optical communication with reaction cell 32, and is in turn in optical communication with detector 35. In some cases, the detector has multiple sensing elements, each for detecting light having a different color spectrum. For example, in the case of sequencing, the detector for each reaction cell may have four elements, one for each of the four bases. In some cases the sensor elements provide color discrimination, in other cases, color filters are used to direct the appropriate color of light to the appropriate sensor element shown as a multicolor discriminating set of sensor elements $35w$-$35z$. In the illustrated embodiment, four sensor elements are shown (e.g., $35w$, $35x$, $35_y$, and $35_z$), however, one will appreciate that one, two, three, four or more sensors may be utilized. The sensor elements are coupled to appropriate electronic components 44, such as busses and interconnects, that make up the overall sensor or camera. The electronic components can also include processing elements for processing the signal from the detectors.

One aspect of the invention is an integrated sensor element that is capable of discriminating signal from multiple fluorophores as a function of time in real time. These types of systems can be used for monitoring analytical chemical and biochemical reactions such as the action of a polymerase in order to carry out nucleic acid sequencing as described above. Several approaches for monitoring multiple fluorophores from one sensor element are described herein. In some embodiments, the different fluorophores are detected at spatially different locations. In some embodiments, each different fluorophore is detected by a single detector element, for example using a pixel which can discriminate different colors of light by the depth at which the light penetrates prior to detection. In some embodiments, the different fluorophores are discriminated by their different fluorescent decay profiles (lifetime). In yet other embodiments, the different fluorophores are excited by different illumination sources, each of which is modulated with time, and the identity of the fluorophore is identified by correlating the timing of the emission with the timing of the excitation. In some cases, these methods for discriminating the fluorophores can be combined for improving detection and discrimination.

Photonic Band Gap Detector

The excitation/detection components of current optical collection systems are generally very complex with numerous lenses, dichroics, holographic phase masks and other elements that are expensive, difficult to keep in proper alignment and prone to increased downtime due to their complexity.

In some embodiments, the system of the present invention combines the waveguide illumination of the reaction cell with a set of photonic band gap (PBG) layers that take the place of dichroic filters in current systems, and one to four detectors per reaction cell, and a unified solid state device can be achieved. This PGB approach provides one method of spatially discriminating different fluorophores.

Figure 3:
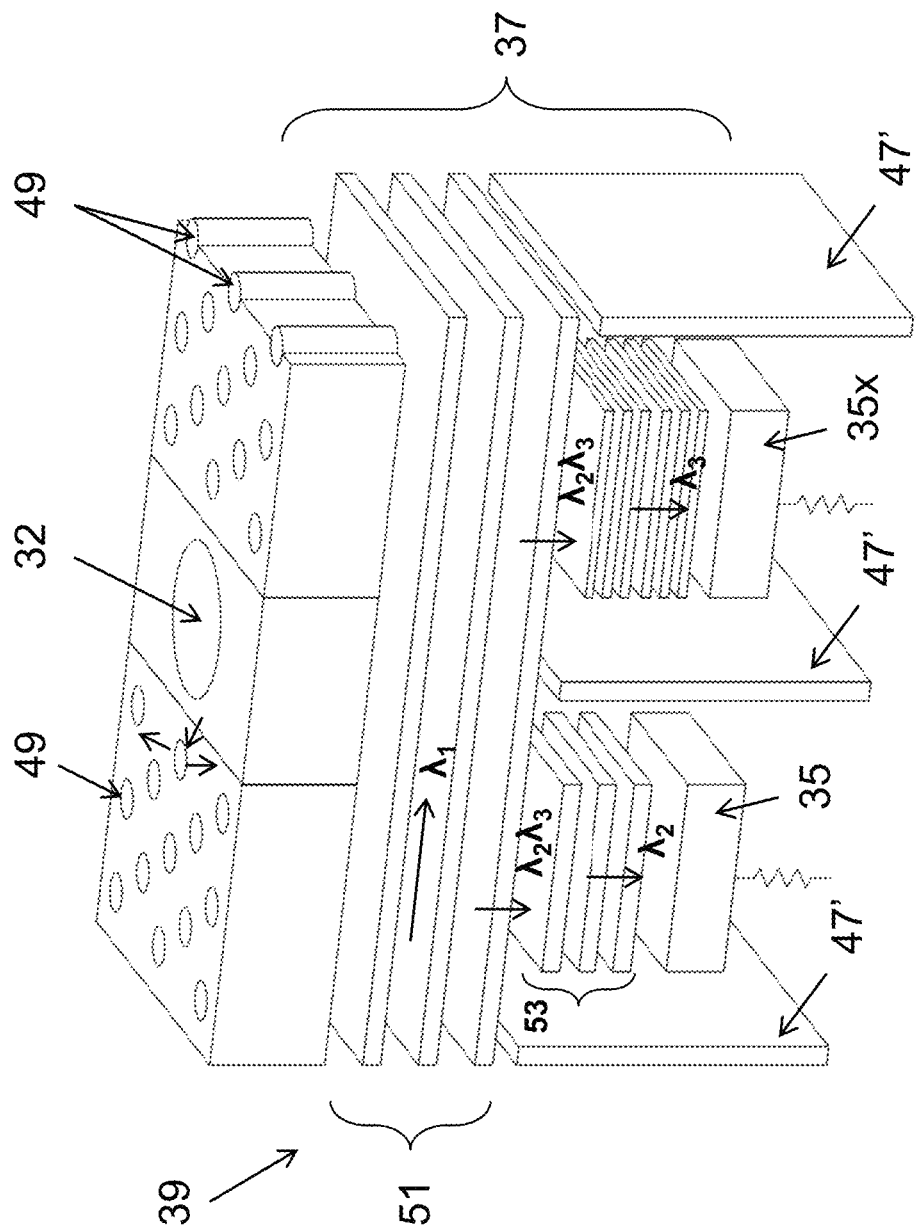
FIG. 3 is a schematic view of an exemplary optics collection and detection device of FIG. 1.
Figure 4A:
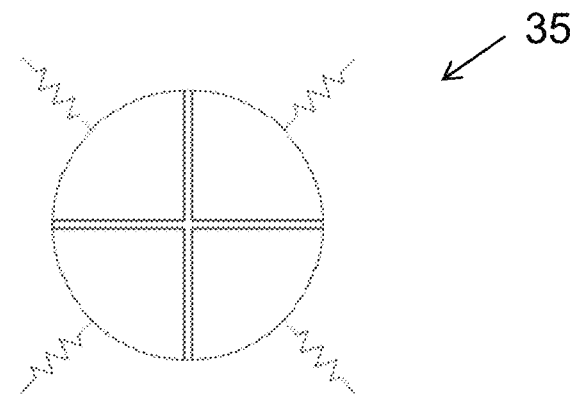
FIG. 4A is a schematic view of quad photodiode (QPD)
Figure 4B:
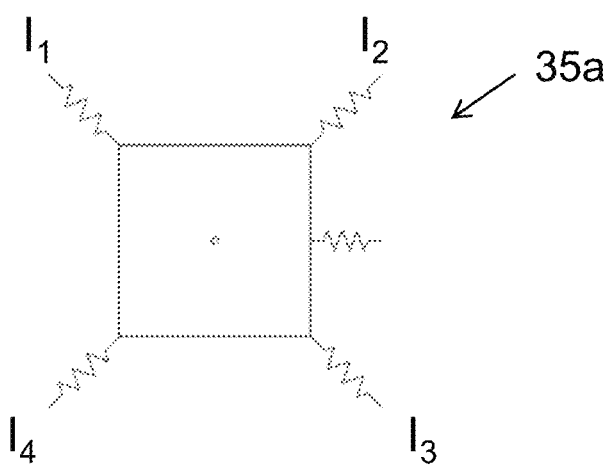
FIG. 4B and FIG. 4C are schematic top and side views of another photodiode, both of which are suitable for use with the device of FIG. 3.
Figure 4C:
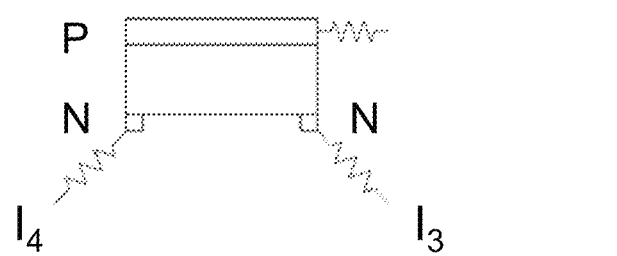

With reference to FIG. 3, each reaction cell 32 is provided with an optic train 37 including at least one channel having several layers of PBG layers 51 which are configured to initially reject the pump laser, that is, to reject the illumination light ($\lambda_1$) provided by illuminating waveguide 39 but allow excitation light to selectively pass through each channel to a respective detector (e.g., 35, $35_x$). For example, the illustrated embodiment includes four channels (two of which are shown in FIG. 3, all of which are shown in FIG. 4A), each of which are optically isolated from one another by a metal shield or other suitable cladding 47 so that excitation light may be directed to a respective sensor element (e.g., 35, $35x$).

The top layer contains reaction cell 32 with an illuminating waveguide 39 below. As illustrated, a device channel may be created with a series of dielectric posts 49 with high index of refraction, which posts provide lateral confinement of pump laser light from the illuminating waveguide to the region about the reaction cell, and may allow higher light density than a simple fused silica layer without PBG layers for the same pump intensity.

Even though the index mismatch of the waveguide and cladding may prevent most light from escaping towards the sensor (by total internal reflection), a one-dimensional (1-D) PBG layer 51 that passes emission wavelengths but attenuates pump lines may be added for better SNR. For example, the 1-D PBG layer may reject $\lambda_1$ but allow $\lambda_2$ and $\lambda_3$ to pass to the photodetectors below. The 1-D PGB layer may include one or more semiconductor-based structures of miniature band-stop filters. PBG filters are especially suitable for use with the systems and devices of the present invention as they are much easier to manufacture and use with other circuits, and is far more compact than conventional filters.

In the next level down, two more PBG stacks 53 are shown side-by-side, which pass different wavelengths, hence create wavelength specificity. These are essentially band-pass filters. The illustrated embodiment is a four color system including the two stacks shown in FIG. 3 (e.g., stacks 53, $53_x$), and two more stacks with different spectral properties are directly behind. In the illustrated embodiment, the PBG stacks are configured to pass different excitation light of different wavelengths in the range of approximately 100 nm to 1 μm. For example, stack 53 may be configured to allow excitation light of wavelength $\lambda_2$ to pass but reject light of wavelength $\lambda_3$, while stack $53_x$ may be configured to allow excitation light of wavelength $\lambda_3$ to pass but reject light of wavelength $\lambda_2$. The illustrated embodiment includes four stacks, which in various embodiments may be sufficient to pass sufficient light with out further guides, however, one will appreciate that one, two, three, four or more PBG stacks may be utilized to provide the desired number of channels.

Optionally, metal attenuators 47' or other suitable cladding may be added adjacent to the stacks to prevent crosstalk, or vertically-oriented 1-D broadband PBG layers can be added that reflect and guide light toward the respective sensor elements 35, 35x of the detector.

Turning now to FIG. 4A, detector 35 is may be a quad-photo-diode (QPD) detector having electrically separated quadrants serving as each sensor element (e.g., 35, $35_x$, $35_y$ and $35_z$) which measures respective signals. Preferably, each sensor element is aligned directly below a corresponding PBG stack (e.g., 53, $53_x$) thereby forming respective optic channels. Each sensor element may determine when excitation light passes through a respective PBG stack (e.g., 53, $53_x$, etc.).

Alternatively, the detector may be a position sensitive diode such as a PIN diode junction that provides the relative location of the each photon pulse as it lands on the detector. For example, detector 35a may have a generally square configuration including a relatively thick intrinsic semiconductor (I) between an upper p-type semiconductor (P) and n-type semiconductor regions (N) positioned at the four lower corners of the detector. Depending upon the proximity to the respective corner n-type regions (e.g., $I_1, I_2, I_3, I_4$), one may determine through which PBG stack (e.g., 53, $53_x$, etc.) excitation light passes.

Alternatively, a Bragg filter/dielectric stack/PBG can be used with a single mode fiber and can be used to filter out (e.g., reflect) the input light from the laser while letting the emission light through to the detector. One will appreciate that ZMW emissions have a wide distribution of angles, and that multi-layer dielectric filters can tolerate only a narrow distribution of angles. The fluorescent dipole is very small and thus the emissions occupy a very small phase space volume, and it may be efficiently coupled into a single-mode waveguide, and grating filters can be implemented in singlemode filters. Accordingly, a coupling between a ZMW and a single-mode waveguide may include an in-line Bragg filter to screen out the excitation light.

Figure 34:
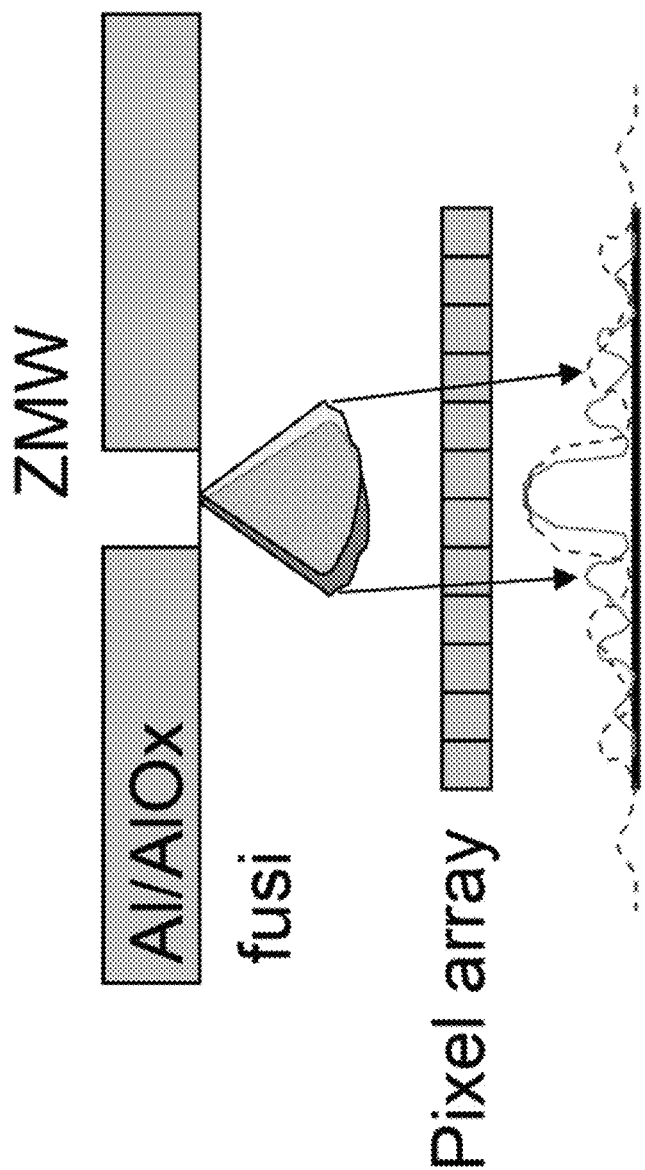
FIG. 34 is a schematic representation of an analytic device converting emission profiles suitable for use in the system of FIG. 1.

For example, a Bragg grating between the ZMW and the detector may simply acts as an interference element to make spatially unique patterns on a 1D or 2D detector, in a manner similar to that shown in FIG. 34 (discussed below), which assumes a point source and the optical path length variation to cause the interference. One would appreciate that one generally wants collimated light at the grating, and thus a microlens may be provided to direct light from the ZMW to the Bragg grating, and in turn, the detector. Optionally, the Bragg grating might be at an angle so that the 00 pump spot is dumped off the detector array and only higher order peaks of the pump are measured and all orders of the dyes.

Integrated Readout Buses, Detector Absorption, Etc.

Integrated sequencing systems and devices require compact and efficient illumination methods to operate at high resolution for low cost sequencing. One limitation is the rejection of source illumination. To effectively reject the source illumination, a method for filtering the frequencies of the source and passing the frequencies of the excitation light or emission need to be incorporated. Various aspects of the present invention relate to methods of using the detector optical properties to perform this filtering to enable compact and low cost sensors.

Figure 5:
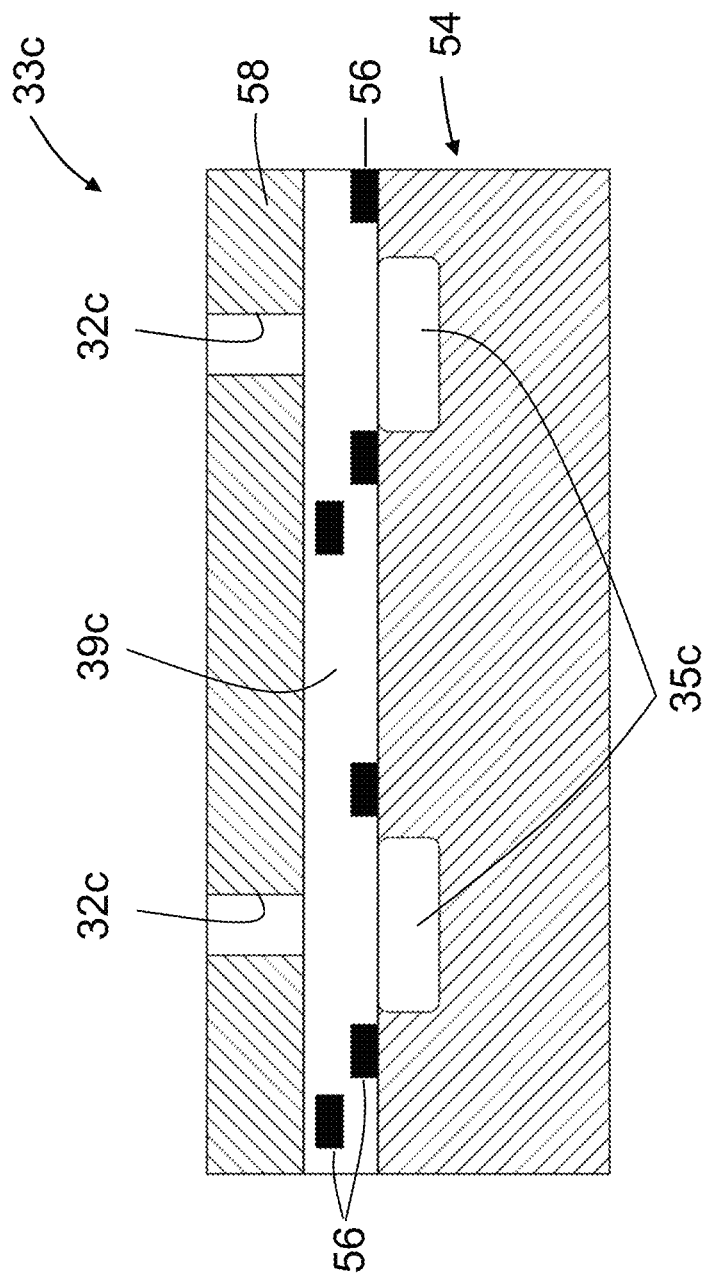
FIG. 5 is a schematic cross-sectional representation of an exemplary integrated structure suitable for use with the system of FIG. 1.

Various aspects of integrated sequencing sensors utilizing illumination confinement to small molecular volumes has been described in the above-mentioned '235 and '916 applications. A cross-section of an exemplary integrated device 33c is shown in FIG. 5 and includes a substrate 54 that may be provided with patterned photodetectors 35c which can be single devices or an array of 1 or 2 dimensions of arbitrary resolution. These photodetectors are arranged with conductive readout busses 56 which generally are opaque to radiation. These metal conductors are arranged in an insulating layer. In the illustrated embodiment, the insulating layer is made from an oxide dielectric and transmissive to optical radiation frequencies and may function as the illuminating waveguide 39c. Such an integrated device may contain a sequencing layer which is made from very small volume optical cavities or reaction cells 32c arranged over the photodetectors 35c. These reaction cells may be made within a top layer 58 which is generally opaque and biocompatible with any required surface treatments to facilitate the sequencing chemistries.

Figure 6:
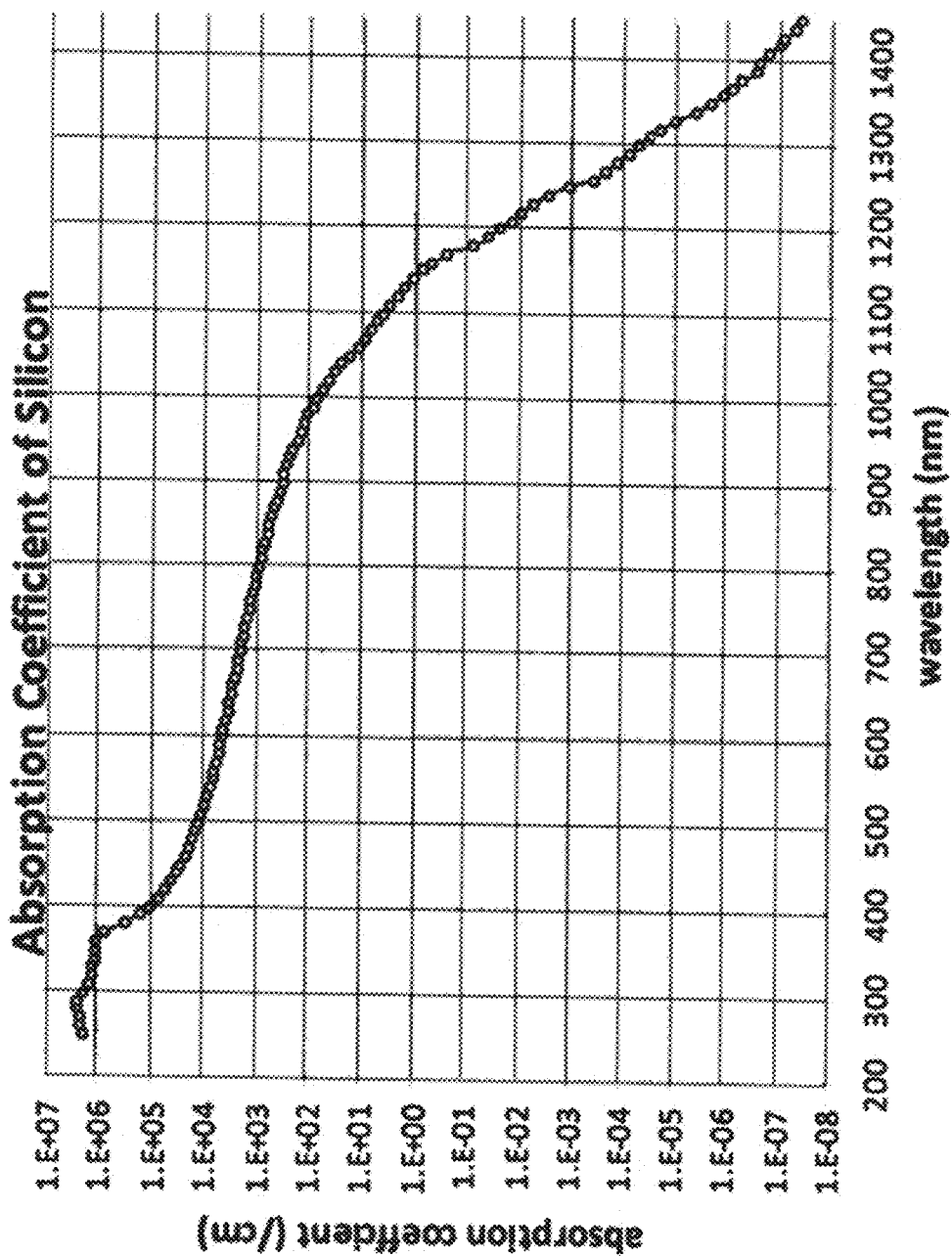
FIG. 6 is a graph showing an exemplary absorption coefficient of silicon.
Figure 7:
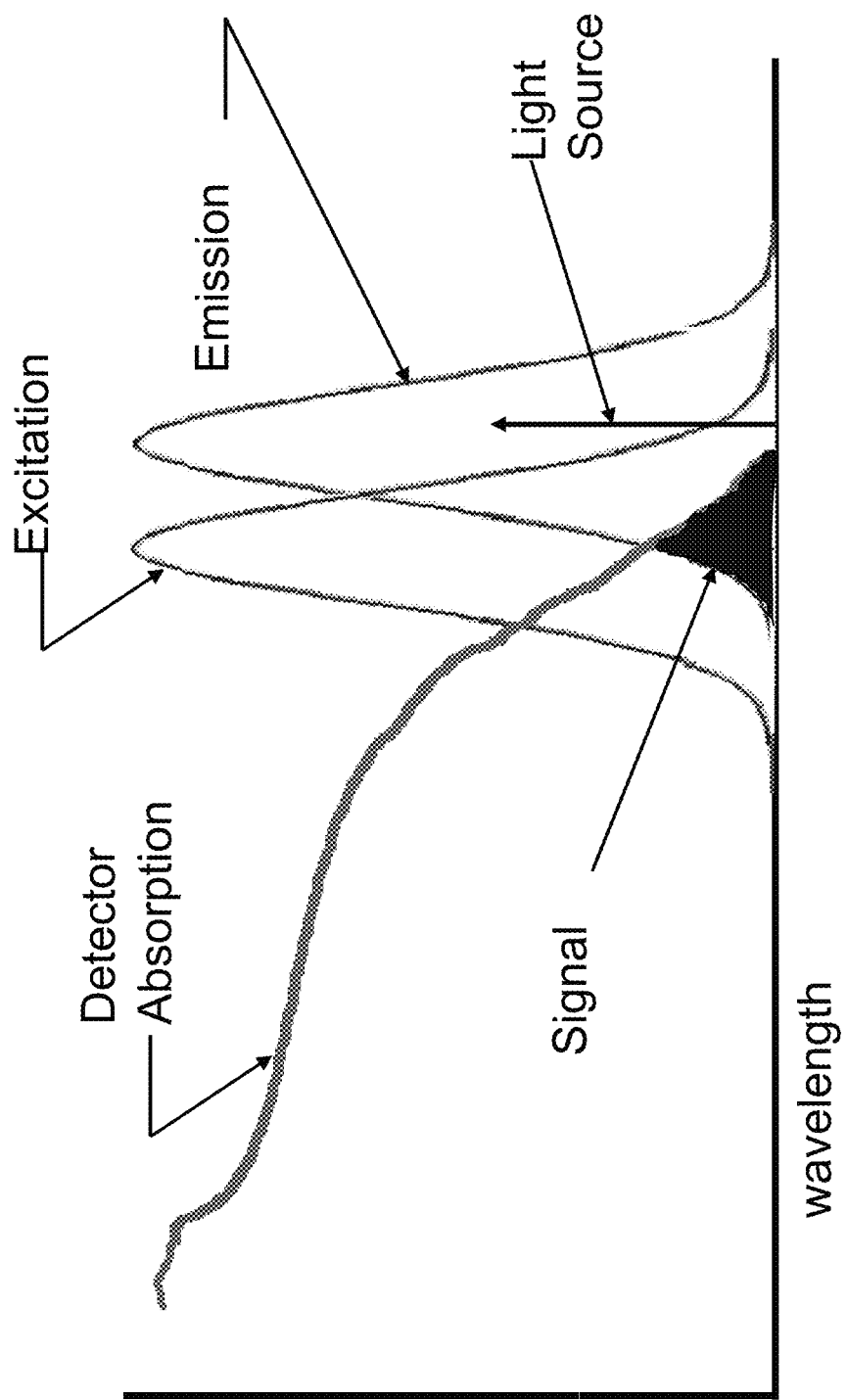
FIG. 7 is a graph showing an exemplary detector absorption curve.

The detector layer has a spectral range where it can operate. As an example, the optical absorption coefficient for silicon is shown in FIG. 6. This represents the coefficient in the exponential decay of normal directed incident photons at each wavelength into the material. It is easily shown from this curve that longer wavelength photons can pass through the material if the material thickness is thin enough. A source of radiation may be chosen to match with an engineered material thickness of substrate to be fully transmitted through the photo detector and substrate. If a standard fluoroscopic dye material is used and the emission and excitation frequencies are carefully chosen to straddle the absorption profile of this engineered wafer, the short wavelength tail of the emission distribution could fall within the detector absorption band while the excitation frequency can be placed in the transmissive region. This is shown in FIG. 7 using the silicon absorption curve as example.

The effectiveness of this approach is increased by maximizing the Stokes shift of the dye and operating in a region where the thickness of the wafer can be manufacturable. For a silicon based detector, this is in the 1100-1200 nm region.

An alternative to wafer thickness tuning of the transmission edge is to use a buried detector or a back illuminated detector with a thick substrate. Another alternative is to use a signal collection photodiode on the front surface and an emission drain photodiode on the back surface. In this approach, the deeper penetrating source photons may be captured and drained to the external circuit while the less penetrating signal photons are captured by the front surface detector and stored.

Doped Fused Silica, Microprism

Dispersion prisms were critical to the performance many existing systems, while dichroic optics are increasingly used for wavelength selectivity. Various aspects of the present invention allow for the integration of dispersion optics into the a semiconductor chip, preferably combining reaction cell with the dispersive element(s). Dispersive elements allow for the spatial separation of different wavelengths of light, allowing for the detection of more than one fluorophore in one optical analysis element.

With reference to FIG. 5, various components of system 30c may be integrated into a semiconductor chip. For example, reaction cell 32c, detector 35c, illuminating waveguide 39c and electronic components (e.g., readout busses 56 may be formed directly on substrate 54, various aspects of which will be discussed in further detail below.

Figure 8:
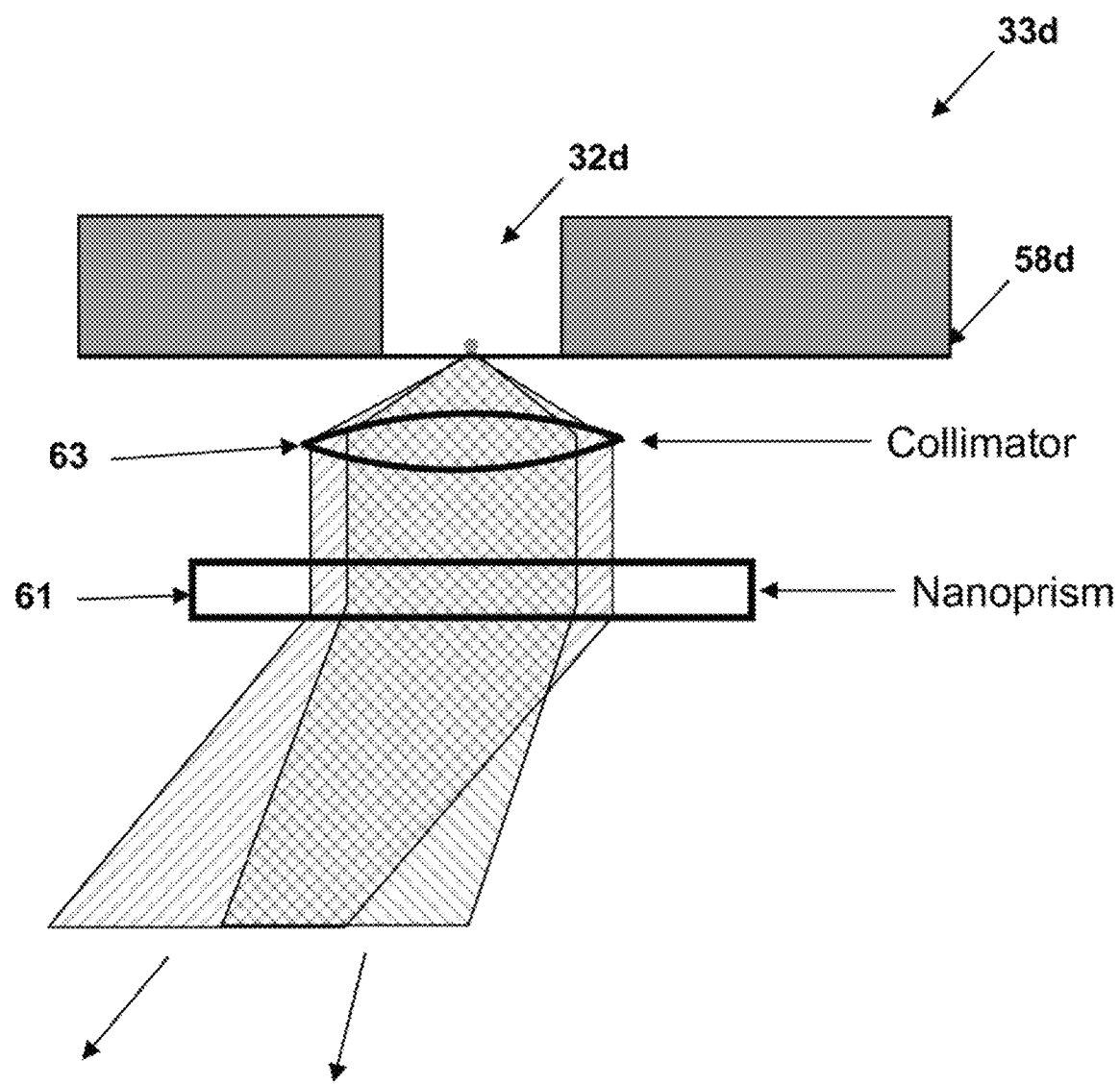
FIG. 8 is schematic representation of an exemplary collimator and prism suitable for use with the system of FIG. 1.

In accordance with the present invention, heavy metals or semiconductors may be doped into fused silica or standard silicon oxide to create an index of refraction gradient, essentially creating a microprism 61, as shown in FIG. 8.

This doped region, mounted near a reaction cell would disperse the light at different angles by wavelength, essentially converting the spectral difference to an angular difference (or in the Fourier plane, a transition). Generally, this device would be on the order of a couple of microns dimensionally.

Optionally, a collimator 63 may be provided adjacent the reaction cell 32a micromirror or a micromirror be fabricated adjacent to or under the reaction cell collimate the outgoing beam and simplify the action of the microprism to be acting on parallel rays.

Various dopants, gradients, size ranges (nanometers to microns), as well as various structures (e.g., various micromirror configurations, microlens configurations) may be utilized with the present invention. One will also appreciate that laser illumination may be provided via an illumination waveguide above microprism or through chip.

Processes for Producing Filters

Other aspects of the present invention are directed to the use of multi-layer optical filters over photodetectors for improved spectral selection and rejection. In particular, a compact molecular sequencing detection system can benefit from the rejection of source excitation radiation that would reduce the sensitivity of the fluorophore signal. The effectiveness of the filter is dependent on the incident angle of the illumination.

Described herein are methods to pattern multi-layer filters below the surface, as well as methods to pattern these materials on a non-planar surface to reduce the distribution of incident angles from a wide angle illumination source.

Methods for the patterning of thin films for optical filtering on semiconductor substrates is well known in the art. Techniques for patterning these films at the atomic level are performed on commercial devices. Multi-layer devices are effective at narrow band rejection or transmission of light. In particular, dichroic filters are important as they pass a narrow band of light while reflecting the out of band wavelengths. These filters do not absorb out of band spectra and do not heat as much. They are however very sensitive to incident angle variations.

In the case of local dye emitters located close to the photodetectors, the emission profile is generally broad in solid angle extent (up to Lambertian). By placing a hemispherically patterned optical filter in proximity to the source (prior to significant scattering or reflection), each ray of light will he normally incident on the filter surface. By patterning hemispherical filters near these emitters, high performance filters can be utilized for high performance sensing applications like single molecule spectroscopy without the need for large free-space optics.

Figure 9A:
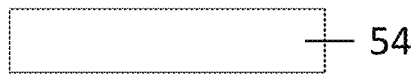
FIG. 9A to FIG. 9N is a schematic sequence illustrating an exemplary method of fabricating optic filter layers suitable for use with the system of FIG. 1.
Figure 9B:
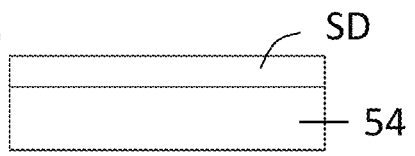
Figure 9C:
Figure 9D:
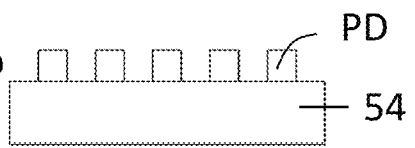
Figure 9E:
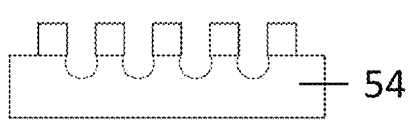

FIG. 9(a) to FIG. 9(m) illustrate a set of semiconductor processing steps enable this device. The set of filters is patterned on the surface of substrate 54, which may be a 6" fused silica substrate (see FIG. 9(a)). A sacrificial deposition (SD) is applied, for example by a Ti/Chrome/DC sputter in an otherwise conventional fashion (see FIG. 9(b)), and a poly etch back and surface clean may then be applied is an otherwise conventional fashion (see FIG. 9(c)). Non critical lithography may be used to form a protective dome (PD) to protect areas of the substrate to remain intact (see FIG. 9(d)). An anisotropic silica etch is performed which leaves the protected areas intact and etches the unprotected areas with significant sidewall ingress (see FIG. 9(e)) to form hemispherical cavities. One will appreciate that various suitable anisotropic etch chemistries may be used, and may be wet or dry to create the desired shape.

Figure 9F:
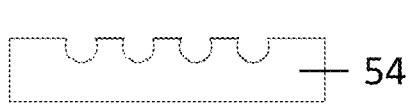
Figure 9G:
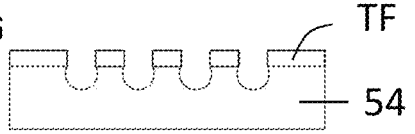
Figure 9H:
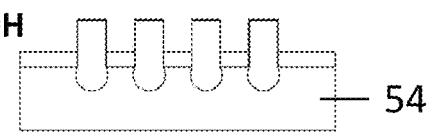
Figure 9I:

The mask may then be removed by conventional ash and clean techniques (see FIG. 9(f)), and the thin film filter is processed with standard vapor deposition techniques to provide a combination thin film deposition for filter. Conventional PVD/CVD techniques may be used to deposit a thin film (TF)(see FIG. 9(g)). Conventional lithography techniques may again be used to provide protection within the hemispheres formed.

Figure 9J:
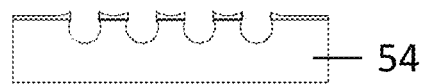
Figure 9K:
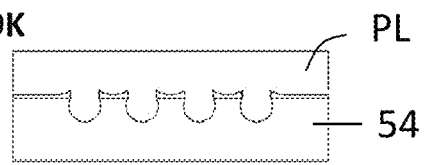
Figure 9L:
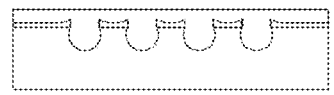
Figure 9M:
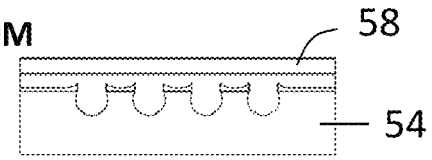
Figure 9N:
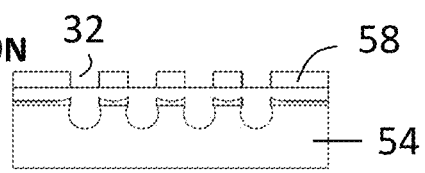

The filters within the hemispheres are protected as the filter material removed from the top silica surface (see FIG. 9(j)). An index matched planarization layer (PL) is deposited into the hemispheres for optical performance and surface planarization (see FIG. 9(k)). The planarization layer may be a hard layer such as PECVD oxide, or depending on desired optical properties. A chemical polishing step is used for a clean flat surface (see FIG. 9(1)). One will appreciate that conventional CMP or etch back techniques may be used to provide a flat topography. Follow on steps to complete the device can be made on this layer. In particular, a reaction cell array (e.g., a ZMW array) can be patterned with a metal pattern above this glass using proven processes to provide a top layer 58 (see FIG. 9(m)) into which the reaction cells 32 may be formed (see FIG. 9(n)). One will appreciate that PVD deposition may be used to deposit aluminum or other metals to form the top layer.

It is important to note that the steps described above are compatible with follow-on steps following a conventional CMOS device fabrication. One will appreciate that this filter layer and ZMW device can be grown monolithically above a CMOS imaging array to develop an integrated lab on a chip biosensor in a standard commercial foundry.

Coupling of Fiber Optics

One problem that arises in collection systems for ZMW observation is that it is difficult to raise the number of observed reaction cells beyond a limit imposed by available microscope objectives. Since the emission signal is weak it is necessary to collect over as large a numerical aperture as possible and then to relay the collected light with free-space optics to the camera pixel array with the appropriate magnification, for example, approximately 60×. Objectives with magnification and large numerical aperture (NA) have a limited field of view and vice versa. There is an interrelationship between the lens NA, focal length (which relates to magnification), optical quality (which relates to the usable portion of the field of view) and the number of resolvable points within its field of view.

One solution is to use a tapered fiber bundle array to help collect the emission from the reaction wells with a single fiber dedicated to each single reaction cell. The most practical use of such an array would be to use a large field of view objective at a small magnification to convey the light from the system chip to the input face of the fiber bundle. A minimum spacing for the fibers is around 3 microns. Current ZMW spacing of the type described in the above mentioned '235 and '916 applications is 1.33 microns so that only a magnification of 2.5 or 3× is necessary. Such a lens could cover a larger field of view than current objectives. The individual fibers have large acceptance numerical apertures near 1 and will therefore be efficient receivers of the light signal. The objective lens must also have a large NA so as not to lose light along the way, but since the fibers would act like light buckets imaging quality tolerances could be much looser than currently required. Once conveyed to the far end of the bundle the light would be handled in a conventional manner, for example, it may be separated into different spectral components and imaged onto the camera pixels.

Because the fibers can be tapered up to a much larger size and/or spacing the magnification step is taken care of without the need for high tolerance optics and alignments. The size of the fibers at the far end can be chosen to optimize these steps. Another way to use the fiber bundle is to place the reaction cells directly on them. In this case the whole tapered fiber bundle assembly becomes a part of the system chip. Alternatively, plates of fused fiber may be prepared where the fibers are oriented perpendicular to the plate faces. Such plates may be made much more economically. The fibers in these plates will act to conduct the reaction cell emission from one side to the other where a tapered fiber bundle could be positioned to further conduct the light to its far end where the individual ZMW signals are appropriately sized and spaced for relay to the camera.

Because of the guided nature of the solution the form of the collection array at the reaction cells does not have to correspond to the form of the array imaged on the camera. For example a linear array of reaction cells could be reformed by appropriate arrangements of the fibers in the bundle into a 2D array, or a circularly symmetric pattern could be reformed into a rectangular array, etc. The light conducting elements do not have to be glass fibers but may be hollow tubes with reflective internal surfaces.

Photodiode Surface Plasmon Resonance

Existing systems for optical detection of real-time single-molecule DNA sequencing have several other problems. First, multiplexing is partially limited by the physical limitations of optical resolution (which affects the density with which reaction wells can be placed on a chip and still be distinguished). Autofluorescence also limits multiplexing. In addition, when using fluorophores as the detection label, photodamage, may occur, affecting the achievable sequencing read-length. Finally, speed of data acquisition is often limited when using CCD cameras as detectors, and it can be difficult to distinguish a true nucleotide incorporation from a branching event.

Figure 10A:
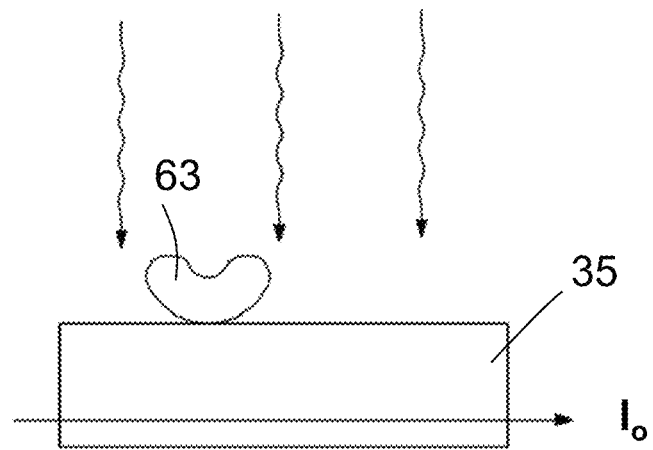
FIG. 10A and FIG. 10B are schematic representations of an exemplary polymerase affixed to a photodiode suitable for use with the system of FIG. 1.
Figure 10B:
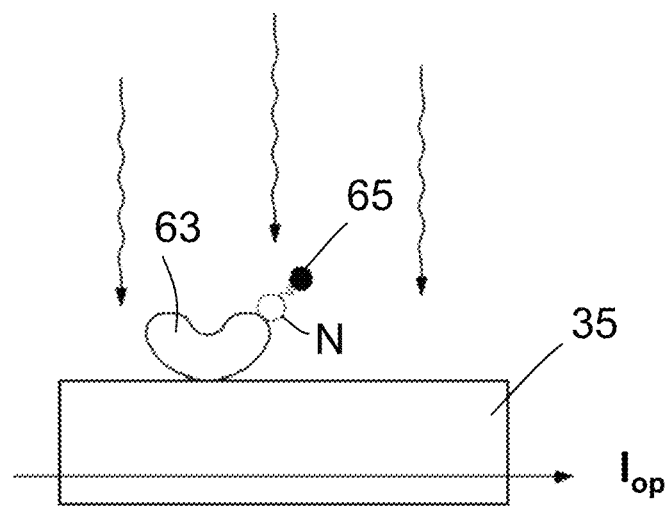

FIGS. 10A and 10B illustrate this aspect of the invention. In accordance with the present invention, a polymerase 63 may be fixed to the detector 35, for example, a photodiode in which the amount of current flowing through the device depends on the amount of incident light. In various embodiments, the nucleotides may be labeled with a metal nanoparticle or a core-shell surface-enhanced Raman scattering particle 65, and for the incident illumination use a wavelength that is at or near the plasmon resonance of the nanoparticle. When the nucleotide (N) is incorporated into the polymerase, the nanoparticle will be very close (within several nm) of the photodiode. A plasmon resonance will be excited in the nanoparticle, which will change the electromagnetic field in the vicinity of the photodiode. In this way, the presence of the nanoparticle will either enhance or reduce the baseline level of photocurrent in the photodiode (e.g., from original photocurrent $I_{op}$ to differential photocurrent $I_{op}$.

In various embodiments, one could use nanoparticles of different size, shape or material to distinguish between the four different nucleotides. Since there is no fluorescence involved, there would be less possible photodamage. Furthermore, the density of photodiode detectors would be limited by semiconductor fabrication methods rather than by optical resolution, enabling greater multiplexing. Finally, data acquisition from a photodiode may be faster than it is with a CCD camera, thus enabling fast polymerase dynamics to be captured more easily.

Four nucleotides could be distinguished by using different sizes/shapes/compositions of metal nanoparticles or by using different types of SERS-active nanoparticles. In addition, different excitation lasers that excite plasmons preferentially in certain nanoparticles could be pulsed, and the detection of photocurrent in the photodiode could be gated to these pulses.

One will appreciate that various types of nanoparticle may be used to label the respective nucleotides, various wavelengths of light may be employed, various materials/structures may be used to fabricate the photodiode, and/or various filtering coatings may be laid down on the photodiode. In addition, since scattering is a coherent affect, the incident light may be modulated for heterodyne detection to decrease the background noise level.

Integrated Sensing and Reactor Cell

Figure 11:
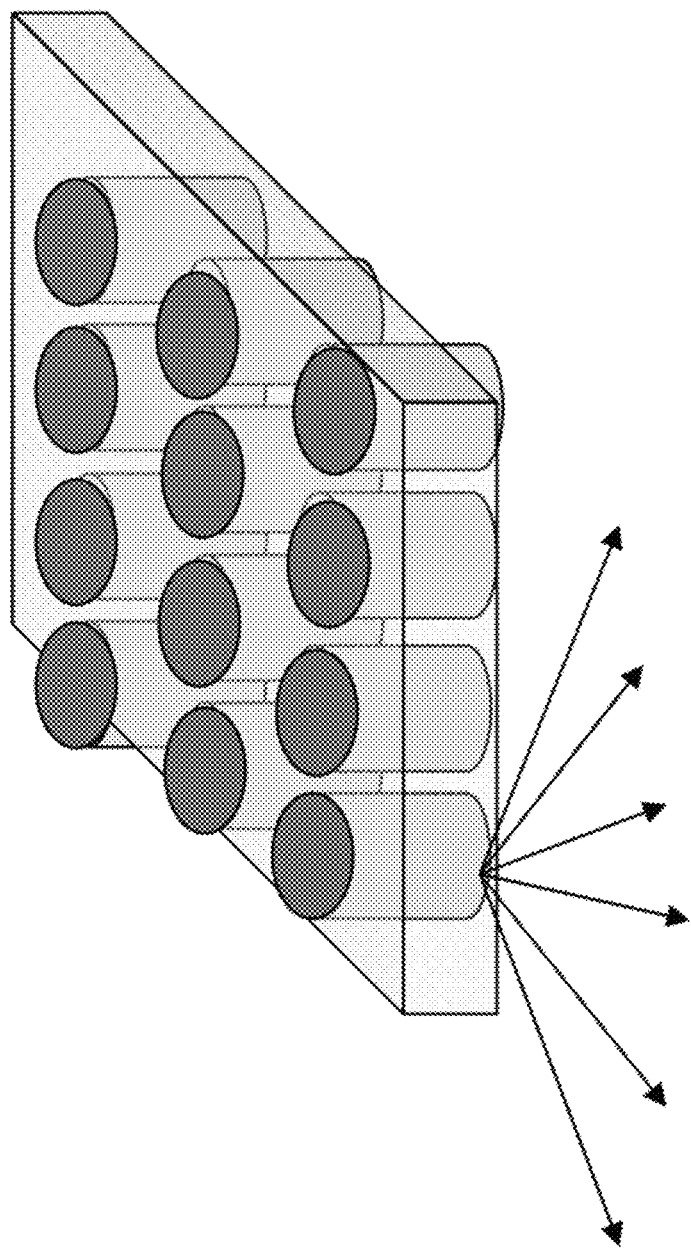
FIG. 11 is a schematic representation of an array of reaction chambers suitable for use in the system of FIG. 1.

Other aspects of the present invention are directed to a design of an integrated sensing and reaction cell where the contents of the emitted optical signal are directed to the sensing element. As described above, the reaction cell is a chamber with extremely low volume as described in the above-mentioned '215 and '916 applications, and known as a zero mode waveguide (ZMW). This reaction cell creates a stimulus illumination volume small enough to isolate a single nucleotide tagged with a fluorophore during chemical incorporation. During this time, the illumination signal is emitted from reaction cell 32 in a Lambertian distribution as shown in FIG. 11. To capture this light, reflective or refractive elements capable of directing this light into a reduced solid angle or a detector capable of gathering the light over this hemispherical surface area can be incorporated to enhance the amount of light that is captured.

Figure 12:
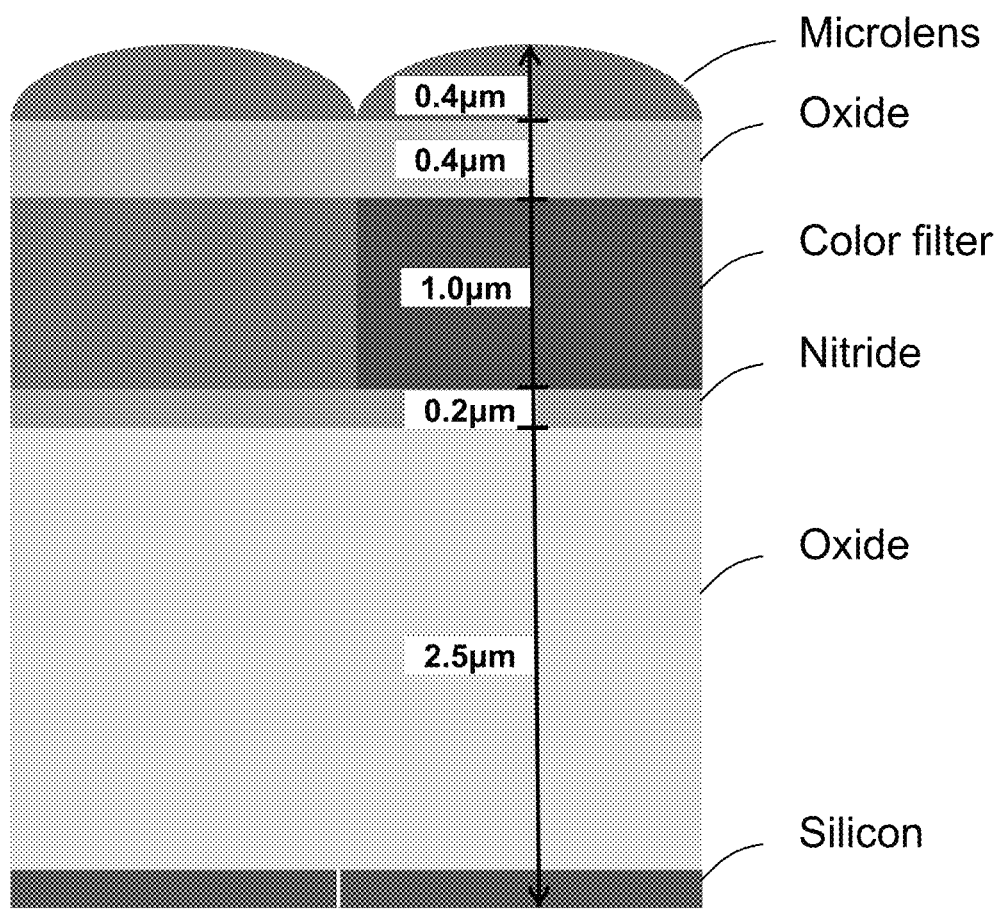
FIG. 12 is a schematic representation of a typical imaging pixel.

A typical imaging pixel cross-section is shown in FIG. 12. A typical CMOS pixel consists of a microlens, a color filter, dielectric stacks, metal interconnects and a photodiode. The photodiode element is located in the silicon substrate and is 4.5 microns below the top of the sensor surface in this example. A microlens is added to many pixel designs to direct light towards the optically sensitive collection area of the pixel and away from the metal interconnects. Scattering and reflection can occur in the regions above the photodiode and the metal interconnects disadvantageously reducing sensitivity.

In accordance with various aspects of the present invention, a pixel designed for intimate contact with the source signal is described. The microlens array is replaced with light guiding methods to confine and direct all light coming from the wide distribution angles of the source to the photoactive area of the pixel. These approaches also reduce the leakage out of the pixel through reflection and scattering to other pixels which would result in crosstalk. A method for fabricating the ZMW arrays directly on the unpassivated CMOS imaging array is presented herein in addition to a method to align the two devices after manufacture. Utilizing a metal cladding tunnel from the nitride passivation layer to the pixel for a reflective path as well as a total internal reflective path utilizing differences in refractive index is also described.

Figure 13:
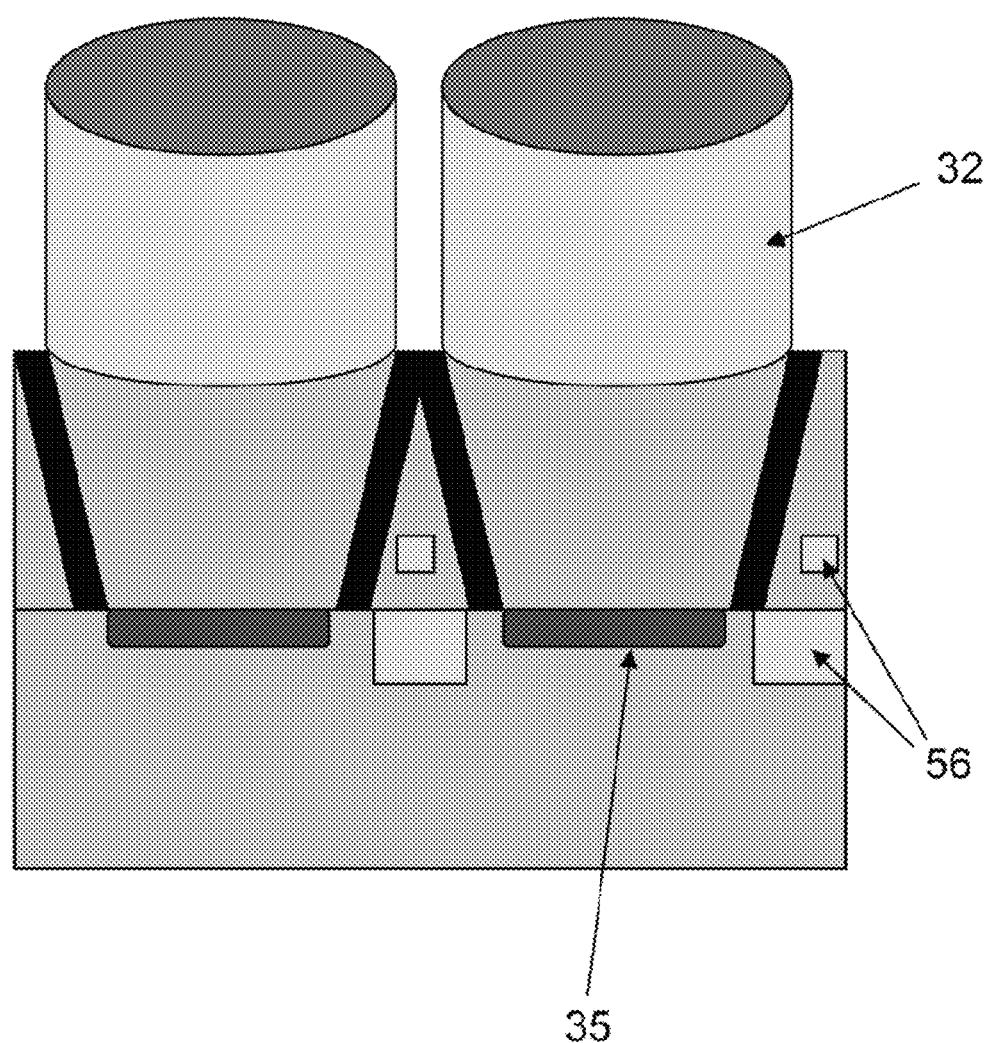
FIG. 13 is a schematic representation of an array of analytic devices suitable for use in the system of FIG. 1.

With reference to FIG. 13, a design utilizing a metal tunnel created above photodiode 35 is created to reflect incoming light to the photodiode is shown in a cross section. Metal interconnects and busses 56 are located in the areas between pixels at lower metal layers creating cones of in coming illumination that are funneled by the metal. At dimensions smaller than the wavelength of light, the transverse-magnetic (TM) polarization at the metal surfaces attracts the light to the metal dielectric interface forming a plasmon-polarization that propagates near the metal surface. This can lead to losses especially in less conductive metals (i.e. tungsten versus aluminum). The transverse-electric (TE) polarization efficiency is much higher.

Figure 14B:
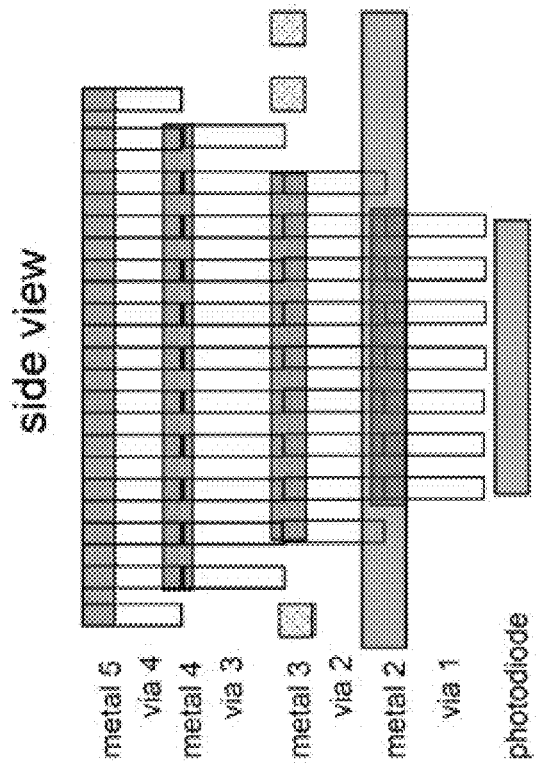
FIG. 14A and FIG. 14B are a schematic top and side views, respectively a Faraday cage suitable for use in the system of FIG. 1.
Figure 14A:
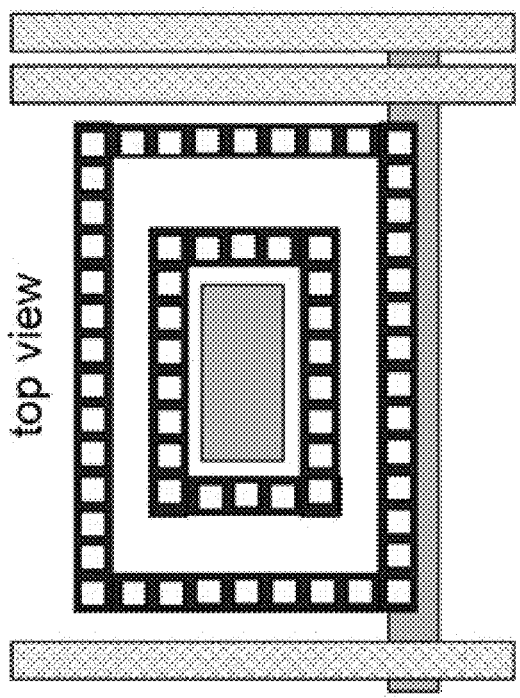
Figure 15A:
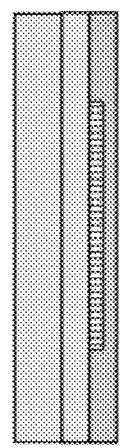
FIG. 15A to FIG. 15G is a schematic sequence of illustrating an exemplary method of fabricating an analytic device suitable for use in the system of FIG. 1.
Figure 15B:
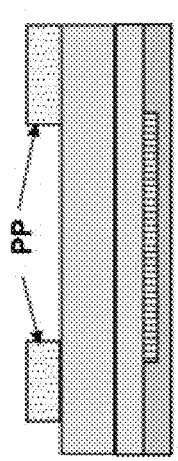
Figure 15C:
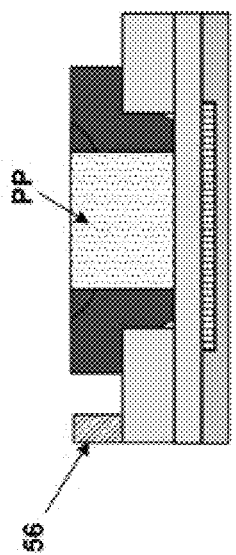
Figure 15D:
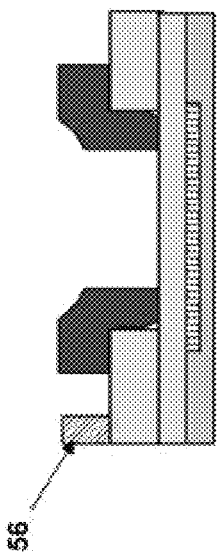
Figure 15E:
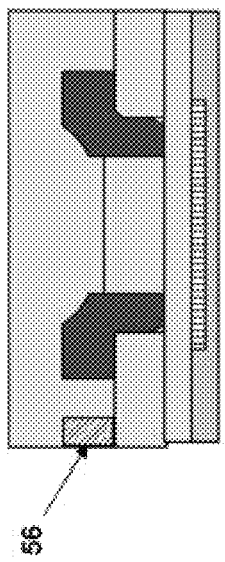
Figure 15F:
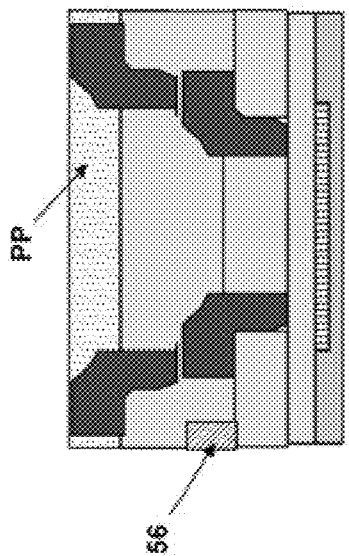
Figure 15G:
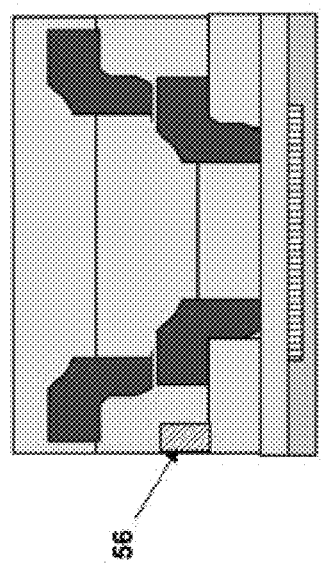

One method of fabricating such cones utilizes planar metal layers and vias placed at a pitch much less than the wavelength of light, which creates a Faraday cage to confine electromagnetic (EM) waves within the cone, directing light to the detector as shown in FIG. 14A and FIG. 14B.

In various embodiments, a set of interconnected metal structures may be formed by the overlapping of a metal ring with an oxide step. In this fashion detailed in FIG. 15(a) to (g), metal rings of increasing radius are stacked on dielectric spacers to build the metal cone 67. The oxide steps and metal thicknesses are designed to allow for full step coverage of the lattice. These same dielectric layers are utilized to insulate the metal vias and busses (e.g., 56) on these same layers around the optical cones. It is noted that photoresist patterning is designated "PP" in these Figures.

The use of a higher refractive index plug (such as silicon nitride (n=2.04) can be used to create a region with total internal reflection. When interfaced with silicon dioxide (n=1.46), total reflection occurs for angles less than 30°. The critical angle of reflection may be calculated from Snell's Law.

$$\theta_{C}=cos^{-1}(n_{cladding}/n_{core}) \qquad \text{Eq. (1)}$$

Figure 16:
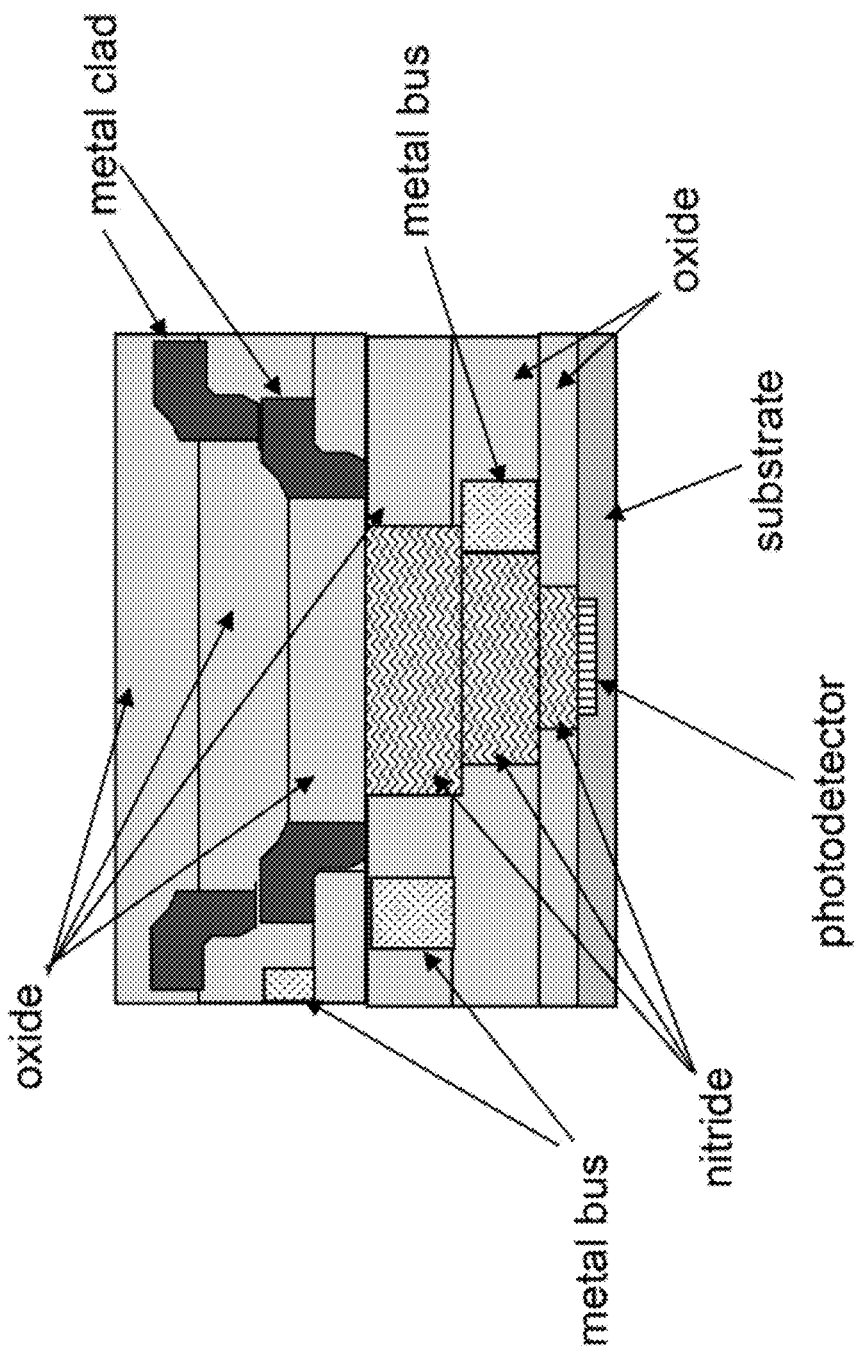
FIG. 16 is a schematic representation of an exemplary analytic device suitable for use in the system of FIG. 1.

In accordance with the present invention, a combination of upper level metal cladding and lower level nitride plugs can be used to direct light to a pixel with high angles of incidence as shown in FIG. 16. The higher efficiency of coupling with nitride plugs can be used to advantage if the incident angles can be reduced from the wide angles output from the reactor chip. By designing the more lossy metal layers to direct light to the lower layers and reduce the angles of incidence, this hybrid approach will yield higher efficiencies. In addition it is further disclosed that high density bussing can be achieved by placing metal lines adjacent to the nitride plug with reduced feature design rules.

Several approaches to an integrated monolithic manufacture of the reaction cell and pixel sensing cells may create a self contained structure that contains all the emitted light to the cell. Three exemplary fabrication methods are shown in FIG. 17(a) to (i).

Figure 17A:
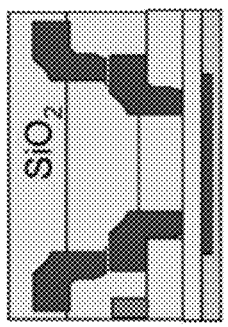
FIG. 17A to FIG. 17I are schematic sequences illustrating exemplary methods of fabricating analytic devices suitable for use in the system of FIG. 1.
Figure 17B:
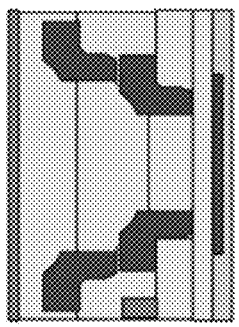
Figure 17C:
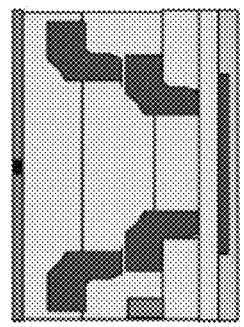

In various embodiments, the reactor cell is grown on top of the imager oxide layer, as shown in FIG. 17(a) to (c). This is similar to the existing fabrication techniques in which a thin layer of aluminum is sputtered on a SiO2 substrate. Features are formed with a sub-micrometer immersion lithography system (For example, like the ASML XM 1950) and etched. These low temperature processes can be performed after the standard CMOS imaging device is fabricated.

Figure 17D:
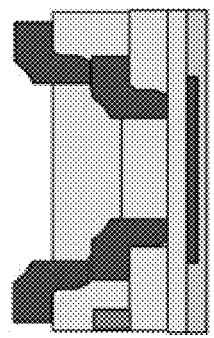
Figure 17E:
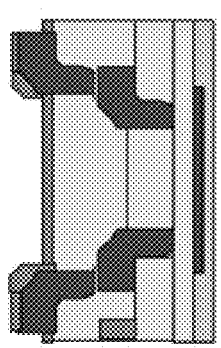
Figure 17F:
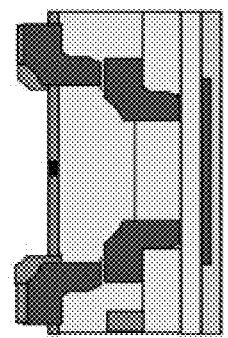

In an alternative approach, the oxide above the top metal layer is removed and the reactor aluminum layer is deposited directly on the remaining layers, as shown in FIG. 17(d) to (f). The pixel shield and reactor layer are conformally merged with the reactor aperture located within the flat oxide layer.

Figure 17G:
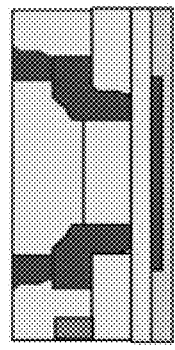
Figure 17H:
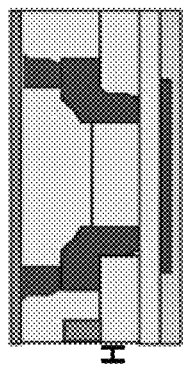
Figure 17I:
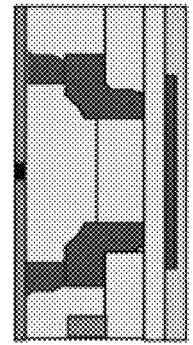
Figure 19D:
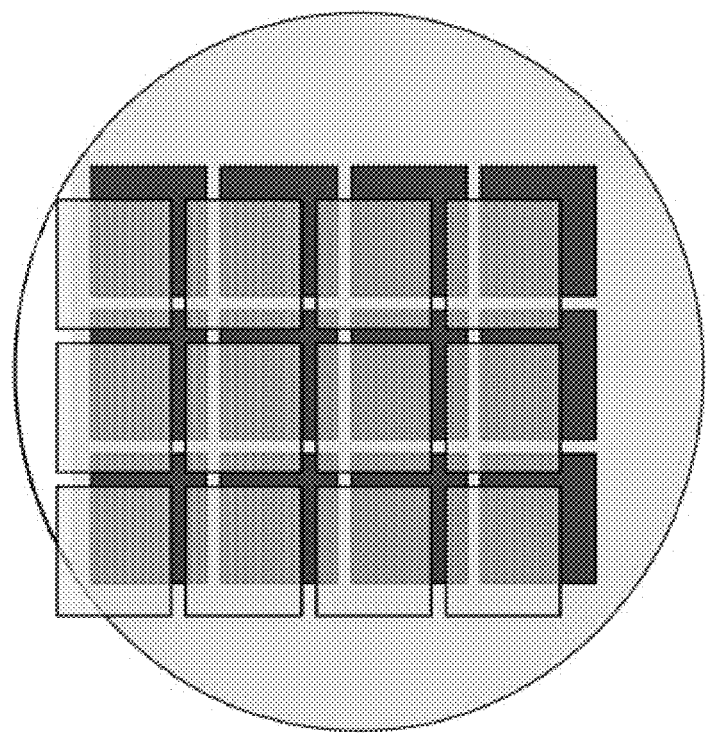
FIG. 19A to FIG. 19D is a schematic sequence illustrating an exemplary method of fabricating an analytic device, along with a plan view thereof, suitable for use in the system of FIG. 1.
Figure 19A:
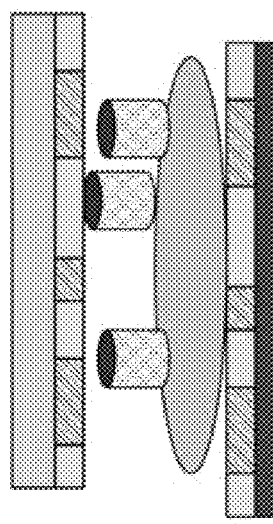
Figure 19B:
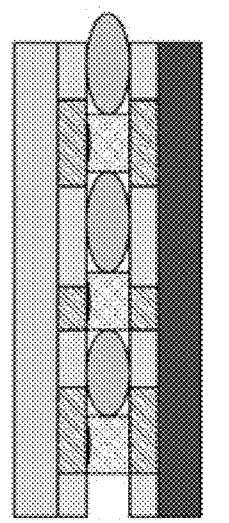
Figure 19C:
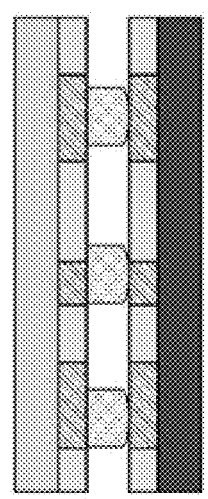

In another alternative approach, the surface of the CMOS sensor is planarized using a standard chemical mechanical polish (CMP) step, as shown in FIG. 17(g) to (i). This exposes the top layers of the metal pixel shield with the Sift optical pixel path in a flat plane. A ZMW metal layer is sputtered onto this layer creating a self contained optical cavity. The reactor aperture is patterned. The use of self assembled multi-chip modules is also disclosed where known good die of the lower yielding component are impressed upon a wafer of the second constituent device.

Using one known approach, a silicon dioxide pattern is placed on the top surface of the acceptor device, as shown in FIG. 18(a) to (c). This layer is hydrophilic and identified as "H" areas in the Figure. Contrasting areas of hydrophobic surrounding areas remain between and adjacent the "H" regions. One approach is in the preparation of an excessively hydrophobic surface on the conductor and light shield by treating an aluminum surface with nitric acid. The nitric acid treatment has been shown to alter the surface properties and increase hydrophobicity. After patterning these contrasting areas on both acceptor and donor components, subsequent positioning these components in near alignment with a small amount of liquid shown in as gray ovals, surface tension self aligns these components. It has been shown that alignment accuracy of less than 400 nm is possible and occurs within 100 msec. The liquid evaporates and the devices are bonded with Van der Waals forces.

In various embodiments, the use of nanoscale optical spacers self align to hydrophilic regions using surface tension in a liquid interface. These optical spacers can provide added optical distance, illumination pathways, filtering, steering or focusing. This enhanced integrated photonics assembly is shown in FIG. 19(a) to (d). An optical processing layer may be comprised of individual elements or a patterned array of optical elements equivalent to the sensing and reacting pitch.

In these hybrid assemblies, with or without optical spacers, options for fully enclosed optical cavities are disclosed and illustrated in FIG. 20(a) to (c). It should be noted that an illumination waveguide is added to these figures. These waveguides are placed close to the zero mode waveguides to couple evanescent waves but isolated from transmission of this spatially decaying field from the sensing or reflective elements.

In FIG. 20(a), a discrete optical element used to focus energy to the pixel is shown. This element can be fabricated as a Fresnel, classical, spherical or holographic element with higher performance than traditional photoresist based microlenses. This will direct energy from a high incident angle range onto the proximal pixel. The optical element may also contain antireflection or spectral filtering materials or layers.

In FIG. 20(b), the optical spacer contains an optical aperture with reflective elements to contain the optical energy within the horizontal pixel extent. In addition, the use of a higher index material such as silicon nitride (shown in pink) may be patterned to enhance directed energy to the lower pixel regions through total internal reflection. In this drawing, two example ray traces with reflections off the metal and nitride layers is shown to direct the energy downward to the pixel and contain it within the horizontal pixel extent.

In FIG. 20(c), a zero mode waveguide made from optically transmissive material is shown. The evanescent wave is determined by the relative location of the illumination waveguide and the well. The addition of a very thin metal layer may also be added to enhance chemical performance without introducing significant optical effects (like scattering and plasmon resonance). To contain the emitted optical energy, the top layer contains reflective elements to redirect the energy within the horizontal pixel extent. An optional spacer or focus element is shown as the middle stacked layer that is aligned to continue optical reflective paths towards the photodetector.

Mulitplexed Homodyned and Heterodyned Pixels

Figure 21:
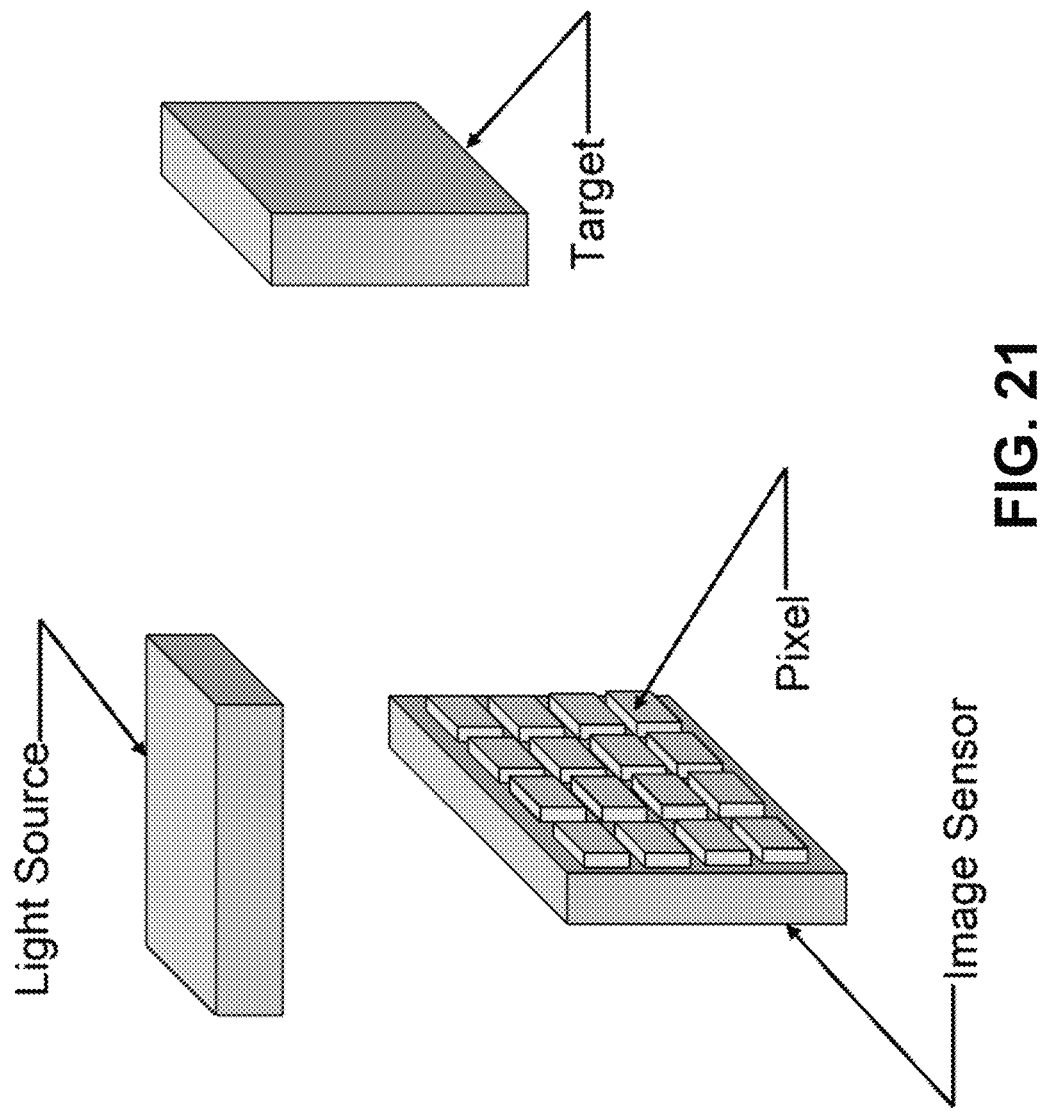
FIG. 21 is a schematic representation of an active illuminated system suitable for use in the system of FIG. 1.
Figure 22:
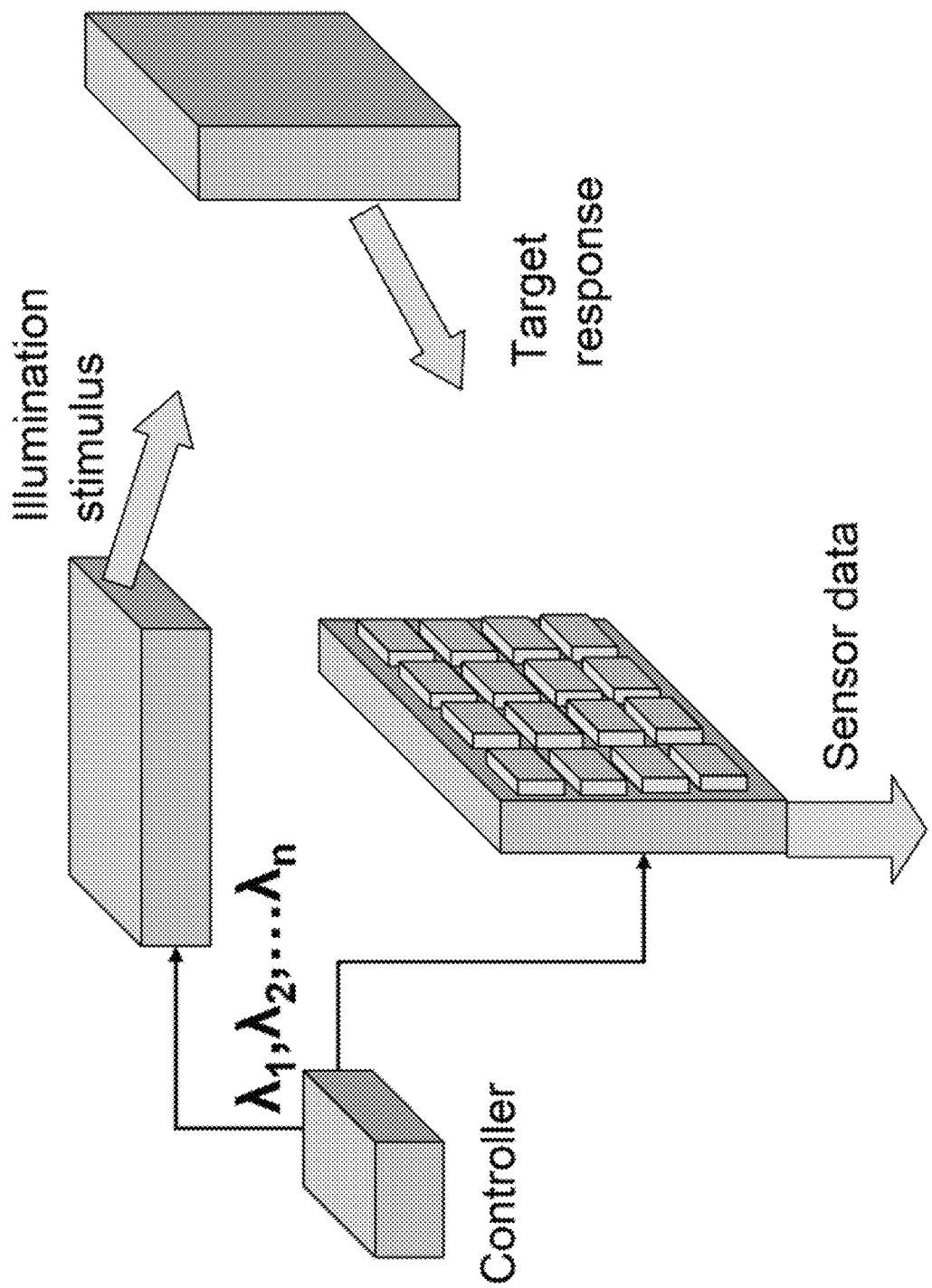
FIG. 22 is a schematic representation of an imaging system with selectable illumination wavelengths suitable for use in the system of FIG. 1.

Turning now to FIG. 21 and FIG. 22, the need to discriminate between the signals of multiple tagged nucleotides with a single photo detector with a priori knowledge of the illumination wavelength energy and arrival time is addressed. This provides a means to incorporate a single photodetector to monitor the process of a chemical reaction with multiple reagent tags as is done in the single-molecule real-time (SMRT) sequencing cell.

With a single photodetector, a savings in cost, complexity and size will be realized. In one embodiment, an integrated pixel matched to the SMRT cell can be developed where the removal of free space optics will enhance photonic sensitivity. In the specific case where free space optics is removed, reduced spectral effects for absorption, angular reflection to spectral distribution, etc. are reduced and the implementation of a polychromatic stimulus is favorable for increased discrimination.

A schematic of the system is shown in FIG. 21. In this system, an active illumination source is used to stimulate the target. The target emission and reflected stimulus signal is incident on an imaging array. The imaging array contains a multitude of pixel sensing elements arranged in a repeating pattern to code the received image.

If the active imaging system is used with polychromatic multi spectral illumination, a system that can utilize this illumination is shown in FIG. 22. In this system, a controller is added that can sequence the illumination wavelength with varying power or pulse widths. Multiple wavelengths can be simultaneously activated or pulses can overlap or be discretely enabled. Knowledge of the current or predicted illumination of each wavelength can be provided to the imaging array. Alternatively, the illumination can be controlled based on feedback from the imaging array.

A pixel design is provided that is able to discriminate multiple signals by synchronizing with a modulated or pulsed stimulus light. The light stimulus may be monochromatic or polychromatic and the pulses may be simultaneous or time division multiplexed. Inventions for systems responding to each type of stimulus are disclosed.

An imaging device is provided containing pixels that can discriminate between multiple signals by synchronization with the stimulus source, arranged in an array and containing circuitry to address, process, and synchronize the device.

A pixel containing a photodiode that is sensitive to polychromatic light is attached to multiple integrating nodes. These nodes can all be connected simultaneously or can be individually selected during the frame time. The frame time is the period between pixel interrogations where the contents are recorded externally.

The photodiode may be connected to each integrating storage node via transfer gates. Charge is accumulated in the photodiode until the transfer gate is asserted. Charge flows to the storage node via charge repulsion, thermal diffusion and node fringing fields.

Figure 23:
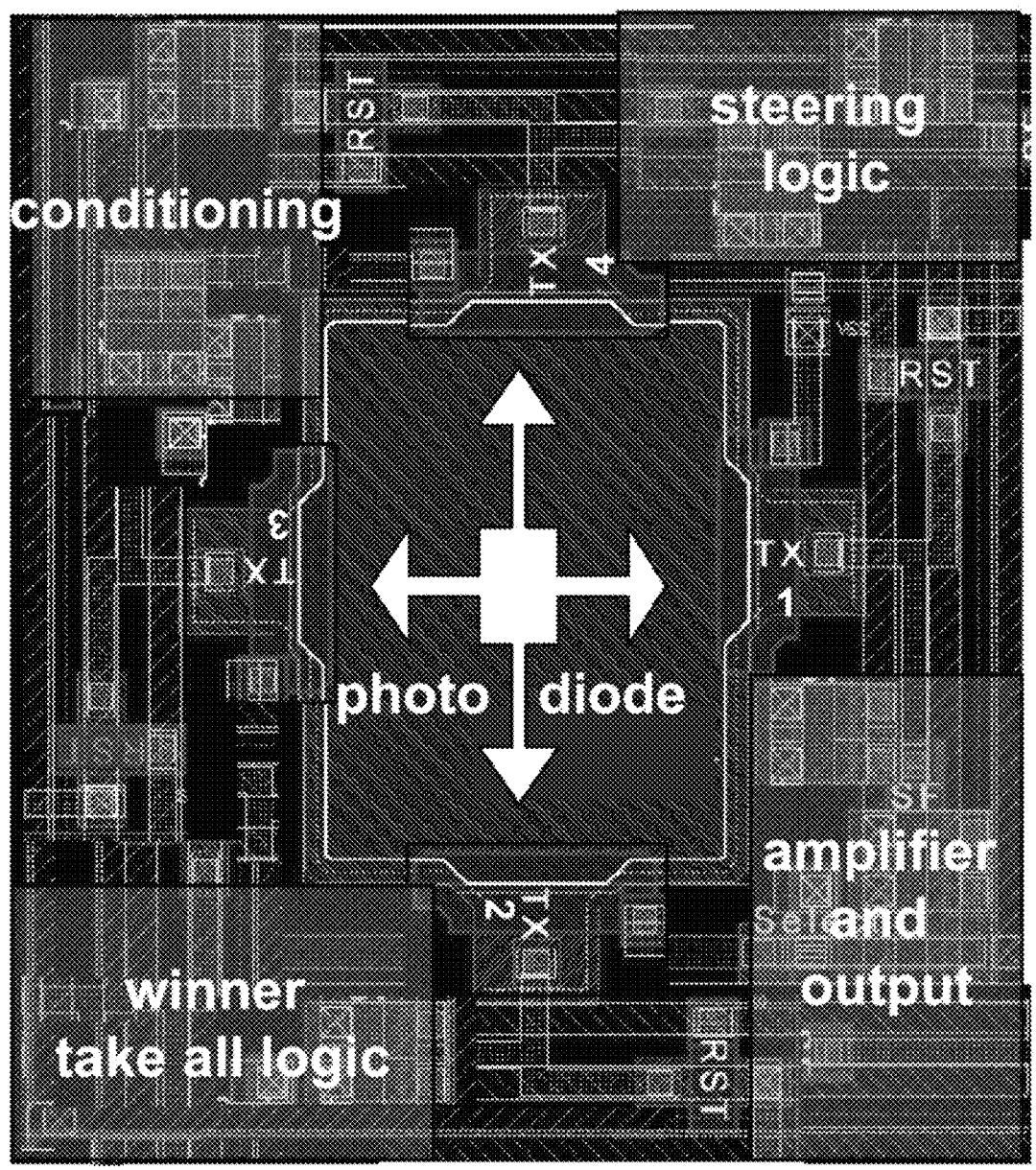
FIG. 23 is a schematic representation of an integrated photodiode suitable for use in the system of FIG. 1.

If the signals from each reactant can be separated in time within a frame period, by switching rapidly to each storage node in the pixel cell signal separation can be gained. An example representation of a pixel layout capable of collecting up to four simultaneous or sequential signals is shown in FIG. 23. At the end of the frame time, local determination of the most likely reactant can be made with amplitude comparators and this in-pixel processing feature is disclosed herein.

A method in accordance with the present invention provides increased accuracy in detecting a longer duration signal pulse via synchronized high speed sampling of the slower pulse within an imaging frame time. By knowing the sampling onset and duration, local averaging of the noise before, during and after the sample can be measured. This is similar to existing methods used with lock in amplifiers and algorithms like discrete saturation transforms to increase the detectivity of low signal to noise pulses.

Figure 24:
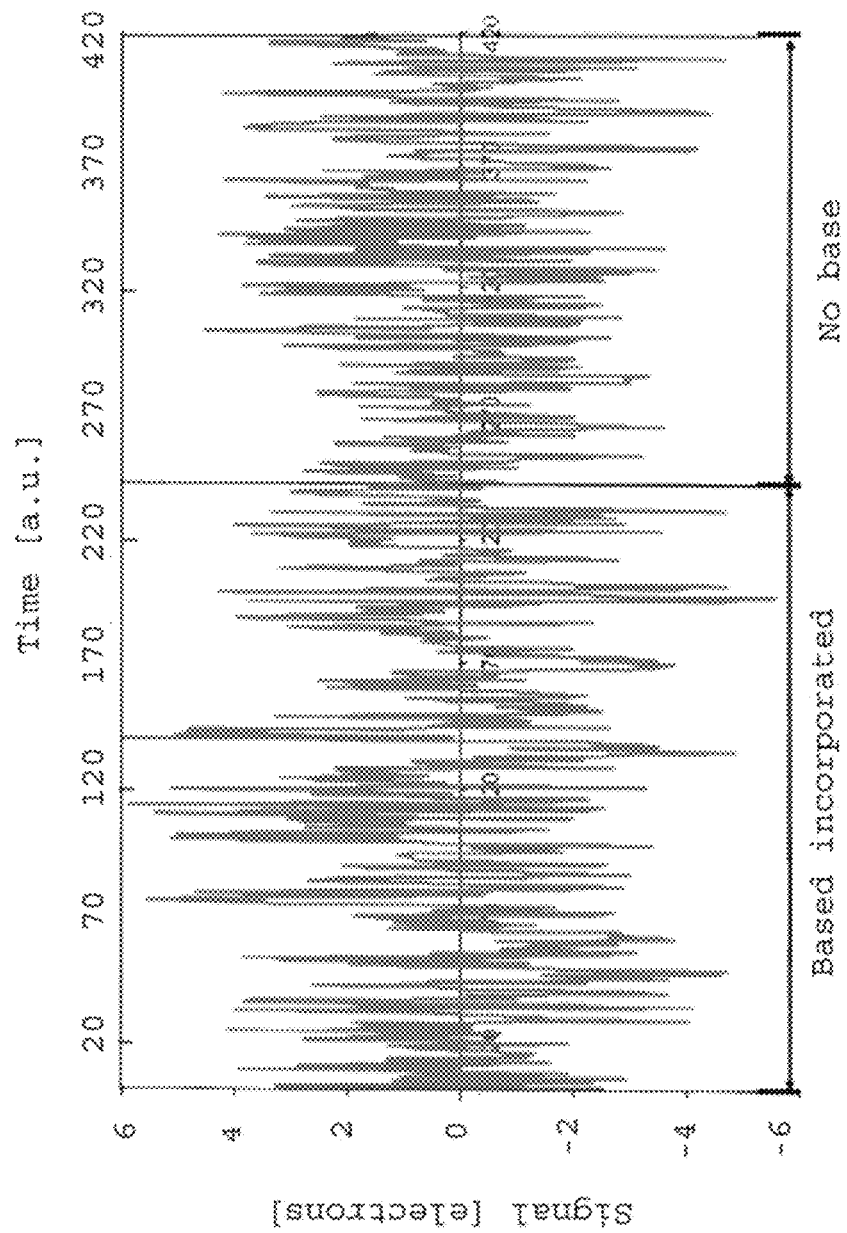
FIG. 24 is a graph illustrating an exemplary time series of a sampled event with 0.6e/sample and 1e-background.

An example of this is shown in FIG. 24. In this figure, a signal of only 0.6 electrons is embedded in an environment with one electron of background signal. This signal is sampled 6 times per frame. The left half of the frame contains a signal during an incorporation event and the right half of the chart does not contain any tagged signal. The tagged signal is not apparent in the data series.

Figure 25:
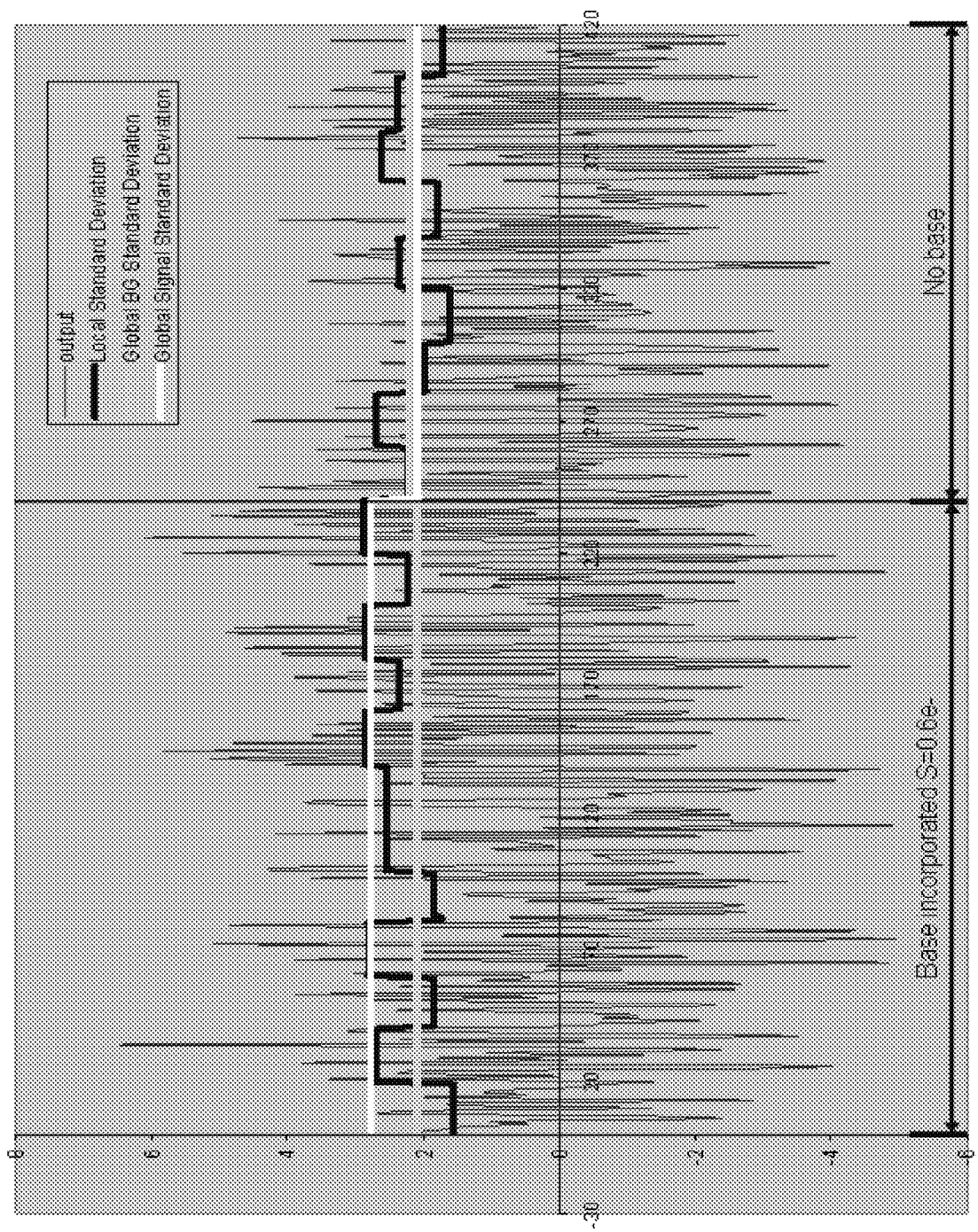
FIG. 25 is a graph illustrating an exemplary result of TDM Pulse extraction with signal=0.5 electron/sample and 6 samples/frame.

The signal is only active when there is an emitting signal (such as an incorporating nucleotide) and a pulse of stimulus: light. By pulsing the stimulus during the frame and measuring the local standard deviation, during both the active and inactive stimulus events, the embedded signal can be extracted from a very noisy environment with a signal to noise ratio of less than 1. This is shown in FIG. 25. In this figure, the local standard deviations during the active illumination periods are combined (shown in the white trace) and compared against the inactive illumination periods (shown in the aqua trace). Clear discrimination of the incorporating period and the time when no incorporation is occurring is shown.

Interleaved sampling can extend this discrimination to n-varieties of signals. The samples corresponding to the variety of emitter sensitive to the stimulus during that frame will provide higher signal and the other stimuli will provide background samples. With this method, if incorporation is occurring in one of four varieties as an example, 25% of the samples will contain signal data and the balance provide background data Also disclosed are methods to utilize the phase shift of a carrier sinusoid to extract signals in extremely noisy environments. This method essentially creates a homodyne with an inherent low pass filter to reduce noise.

After determination of the most likely reactant, the amplitude and species identification can be read out from each pixel in the array up to each frame period. A layout of an example smart pixel is shown in FIG. 23, for example, a pixel with multiple parallel processing elements and additional conditioning and logical circuits to compare each component and perform data reduction.

Figure 26:
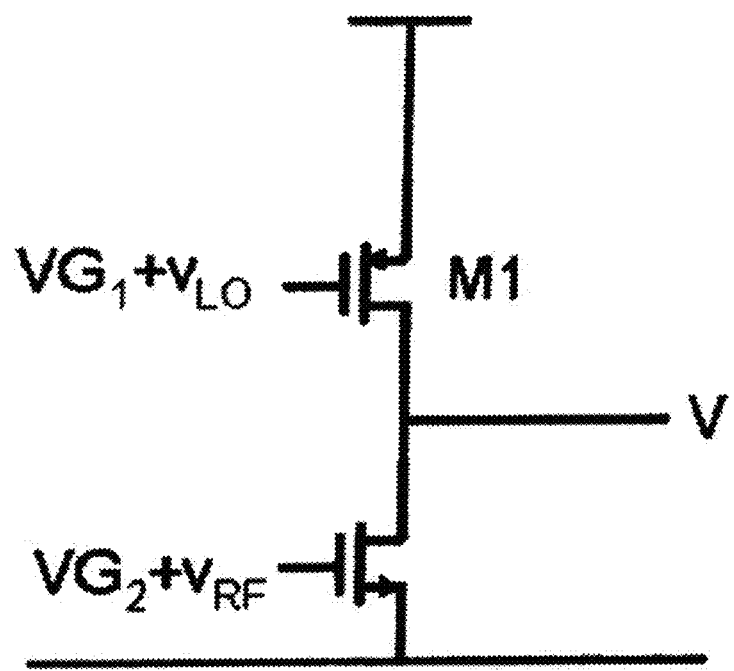
FIG. 26 is a schematic view of an exemplary compact CMOS mixer circuit suitable for pixel implementation in the system of FIG. 1.

Further aspects of the present invention discriminate species based upon frequency differences is disclosed. In this case, each species can be identified by an unique modulation frequency. The signal is recovered with a local mixer circuit embedded in each transfer node of the pixel. A compact low voltage circuit without lumped parameter inductance designed for CMOS device implementation is shown in FIG. 26 and is known commonly as the Gilbert mixer. This down converting mixer takes two inputs, the photodiode output and a local oscillator signal broadcast to all pixels. The top transistor (M1) operates in the linear region while M2 operates in saturation. The current flow through M1 and M2 is therefore equal.

In various embodiments, system designs may utilize multiple illuminants that rely on the separation of dye absorption regions for maximum discrimination. By separating the dye absorptions, each dye can be tuned to the stimulus wavelength with maximum efficiency. As an example. four commercial dyes are detailed in the table below. There are four stimulus wavelengths used and the relative responses for each wavelength are tabulated. In all cases, the contrast in absorption is nearly 4:1 or greater.

Using this approach, there is a one to one response from the dye to its corresponding stimulus with low contamination from other dyes.

| Stimulus | Alexa488 | Alexa532 | Alexa610 | Alexa750 |
|---|---|---|---|---|
| 488 nm | 1 | 0.28 | 0.03 | 0 |
| 532 nm | 0.01 | 1 | 0.09 | 0.01 |
| 610 nm | 0 | 0 | 1 | 0.09 |
| 750 nm | 0 | 0 | 0 | 1 |

Figure 27:
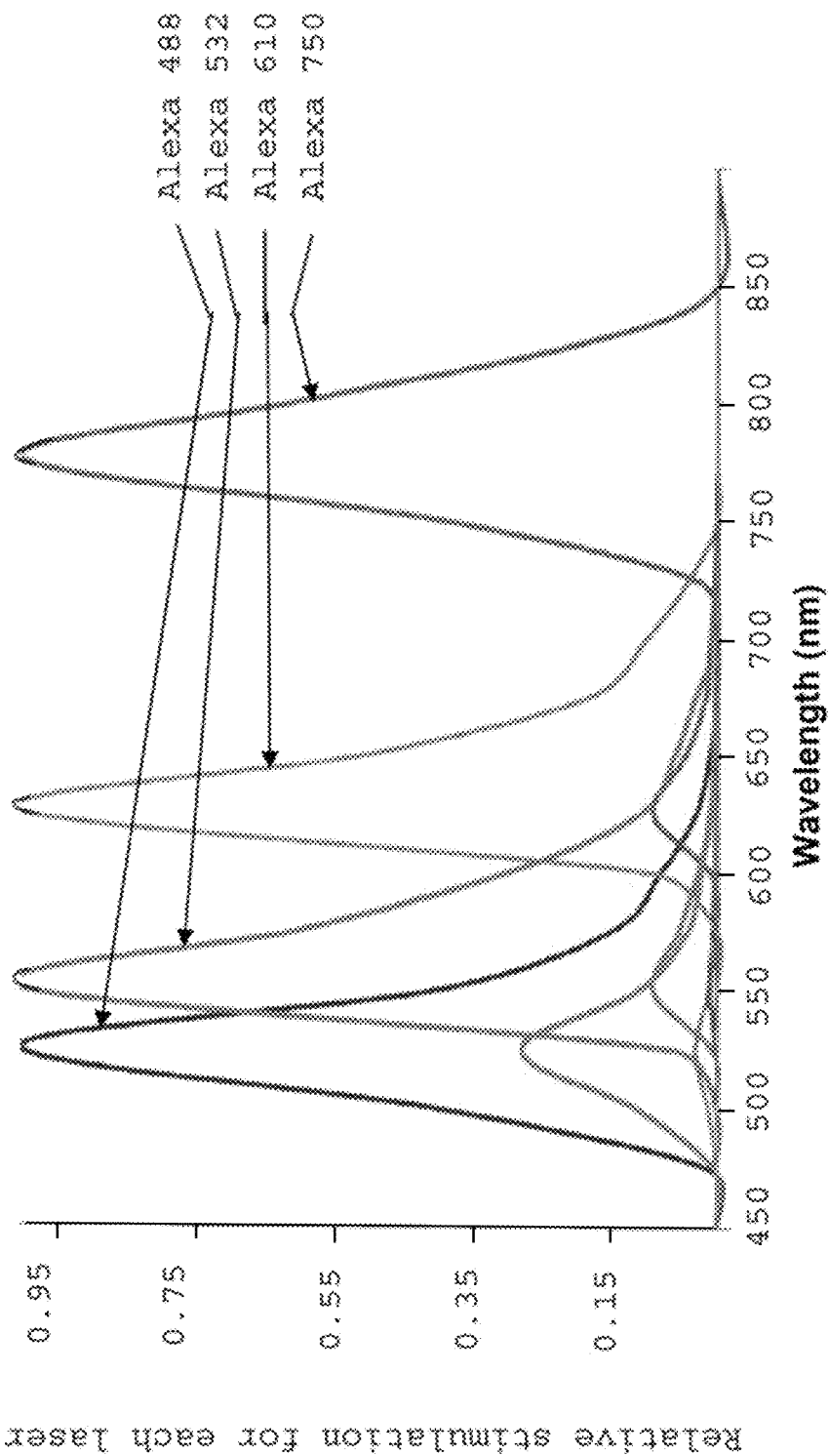
FIG. 27 is a graph illustrating an exemplary excitation for each dye and laser.

The absorption of each illuminant by these four dyes is shown in FIG. 27. In this figure, the cross talk is shown by the reduced power peaks underneath each curve for the matched dye. The 488 nm absorption of Alexa488 is shown in the blue curve. Absorption of Alexa532 of nearly 29% of the. energy is shown in red. The longer wavelength excitations have considerably less absorption cross talk.

Vertical Detector

The current excitation/detection side of many current systems is generally very complex with numerous lenses, dichroics, holographic phase masks and other elements that are expensive, difficult to keep in proper alignment and increase the time-between-failures due to their sheer number. Here we combine the waveguide illumination of the ZMW with a photonics band gap rejection layer and one novel wavelength-sensitive "pixel" per ZMW to measure emission. Registration issues between ZMW, optics and camera are removed by the introduction of this single rigid solid state device.

Figure 28:
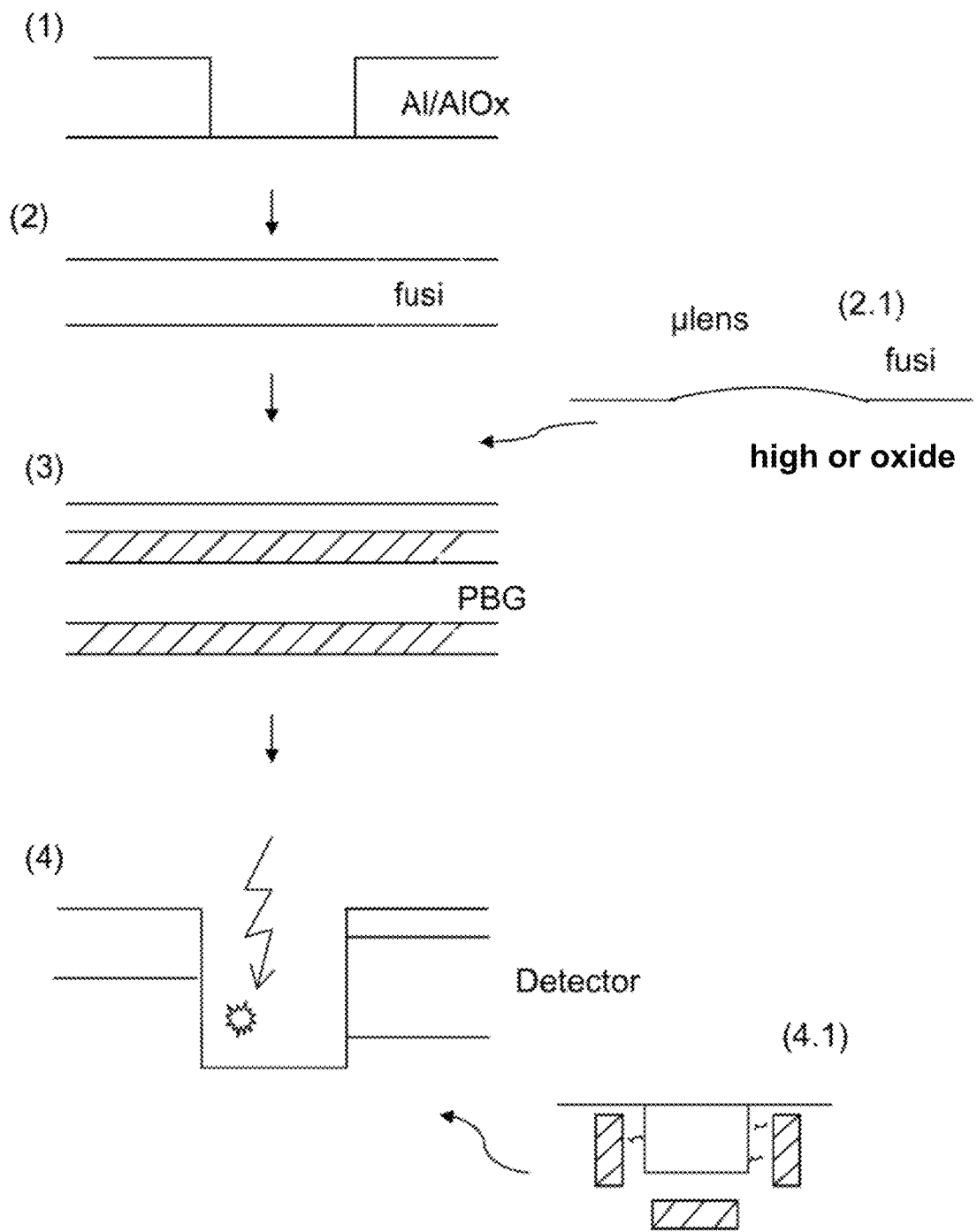
FIG. 28 is a schematic representation of an analytic device suitable for use in the system of FIG. 1.

Various aspects of the detectors may be improved in accordance with the present invention. With reference to FIG. 28, a reaction cell may be provided in a cladding layer such as an Al/AlOx layer (1) with or without a micromirror. Micromirrors are described, for example in U.S. patent application Ser. No. 12/567,526 which is incorporated by reference herein in its entirety for all purposes. In the event that waveguide problems arise, such problems may be compensated for with microlens in photonic band gap (PBG) layer (3). A fused silica (fusi) waveguide (2) with Al metal layer on top and a PBG layer (3) below, potentially with high index PBG "bulge" into fusi to collimate emission (e.g., microlens or "μlens" (2.1)). A 1-D photonic band gap sandwich (3) of complex layers of low and high index material may be designed to block pump lines and pass emission lines. Wavelength sensitive single-pixel detector with (e.g., (4)) or without grounded metal "mini Faraday" shielding (4.1) may be configured reduce ZMW-to-ZMW crosstalk.

In some cases, the waveguide (2) is a single mode fiber for delivering illumination light. While the waveguide is shown spaced away from the ZMW, in some cases, the waveguide can be adjacent to the ZMW. The photon band gap, or dielectric stack (3) can also be disposed within a single mode core, and can be configured so as to reject stray illumination light to keep it from the detector below, acting as an in-line Bragg filter to screen out excitation light. Having a single mode fiber as part of the detection optics is made possible because the fluorescent dipole in the ZMW is generally very small, and thus the emissions from the fluorophores occupy a very small space in phase volume. This results in a relatively high efficiency of coupling the emitted light into a single mode waveguide.

In some cases there can be two different PBG layers or dielectric stacks, one in the path of the illumination light acting as a perpendicular coupler, and the other acting to pass emitted light, and reflect any stray illumination light back up into the ZMW, or back up into the first PBG layer to couple back into the path of the illumination light.

Turning now to FIG. 29, a standard PIN junction (5) may have two or more I-N junctions at different depths. A variation of this design can be produced to have color-specific low-concentration dopants at varying depths to enhance regional absorption. Long wavelength photons that penetrate deeply into the I region, cause significant current from N2 in addition to current from surface-proximal NI (e.g., (5.1)), whereas short wavelength photons are absorbed quickly as a function of depth, and the primary measured current is from N1, with little from N2 (e.g., (5.2)). This device allows for one detector or pixel to distinguish multiple wavelengths, and therefore detect multiple different fluorophores.

Figure 30:
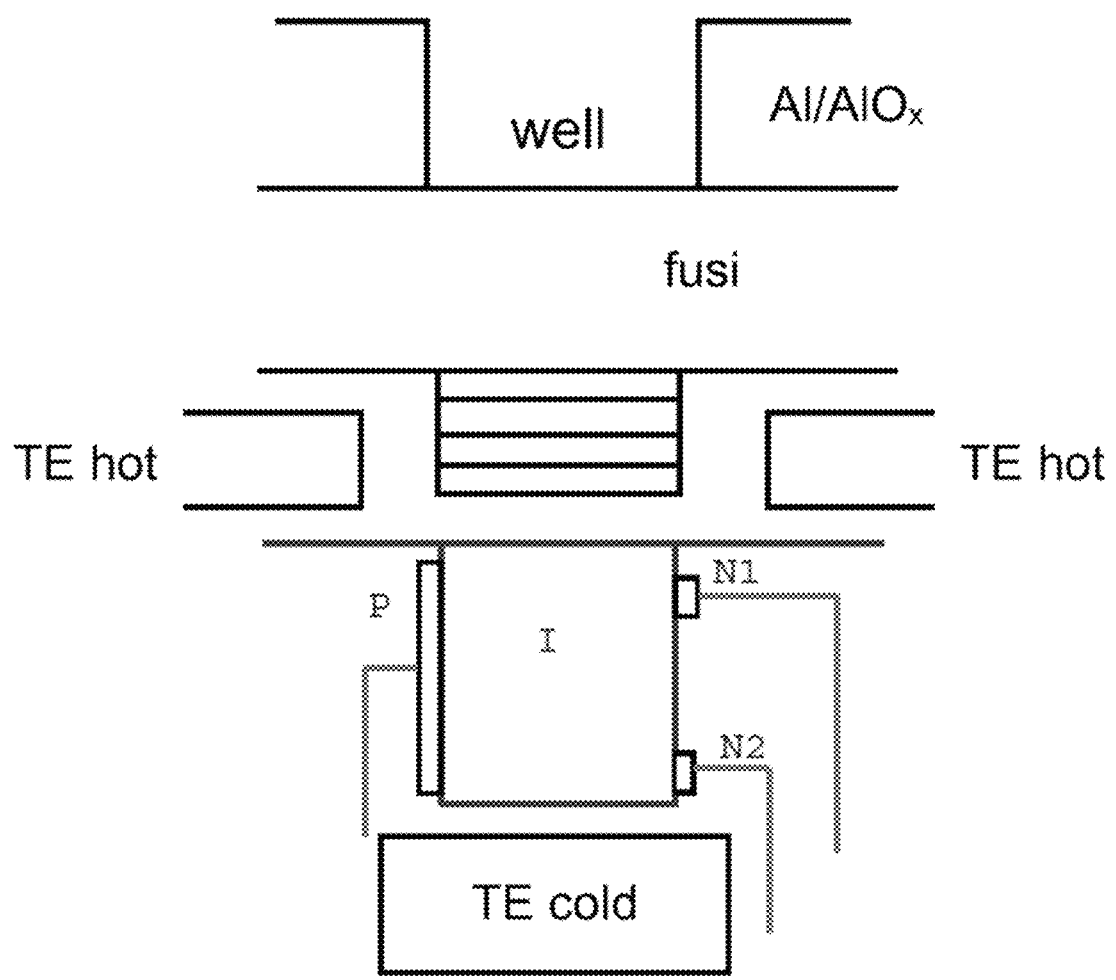
FIG. 30 is a schematic representation of an exemplary analytic device suitable for use in the system of FIG. 1.

Other aspects of the present invention are directed to the provision of thermoelectric (TE) pad arrays near the solution surface, or even in the aluminum metal that forms the ZMW, and other, cooling, pads below the detector to reduce dark current (6) (see, e.g., FIG. 30). Although this may cause significant thermal stresses in the composite chip, it may be desired for implementation for at least two reasons: 1) thermal stability which is critical for proper enzymatic function, buffer stability, and corrosion so the TEs could serve to reduce the local temperature due to, e.g., laser-induced heating; and 2) even a slight temperature decrease for the detector region would benefit signal to noise.

Spectral Dispersion

The following describes a family of spectral disambiguation solutions relevant to "integrated" optical platforms, in which free air optics are miniaturized and condensed into a single monolithic device. These devices and methods allow for obtaining information from multiple fluorophores from a single integrated analysis element.

Figure 31:
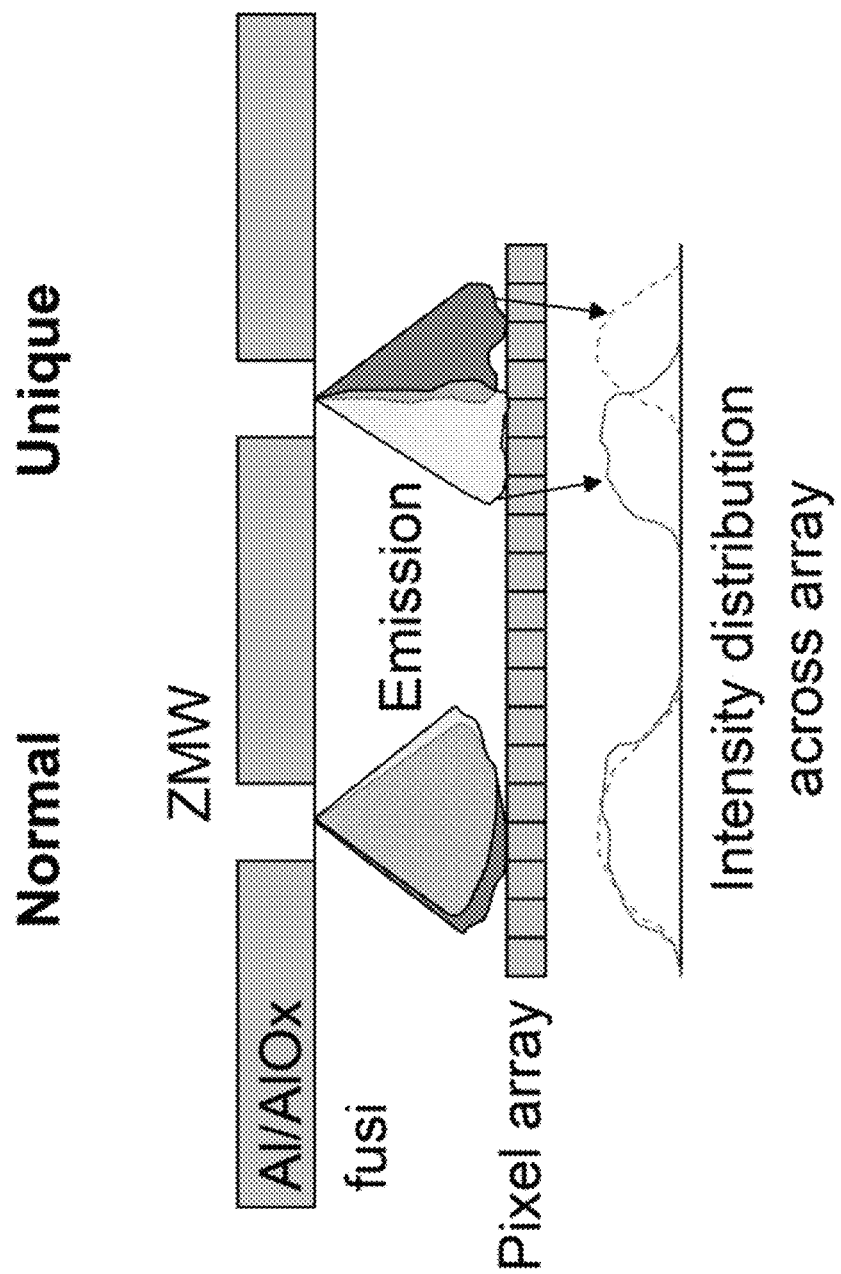
FIG. 31 is a schematic representation of an analytic device converting emission profiles suitable for use in the system of FIG. 1.

With reference to FIG. 31, the fundamental concept is to convert emission profiles per channel from being isotropic ("Normal") in to spatially unique ("Unique") and project these onto a multi-pixel array. Put differently, these are techniques to create a unique pattern on the detector depending on the color of light.

Figure 32:
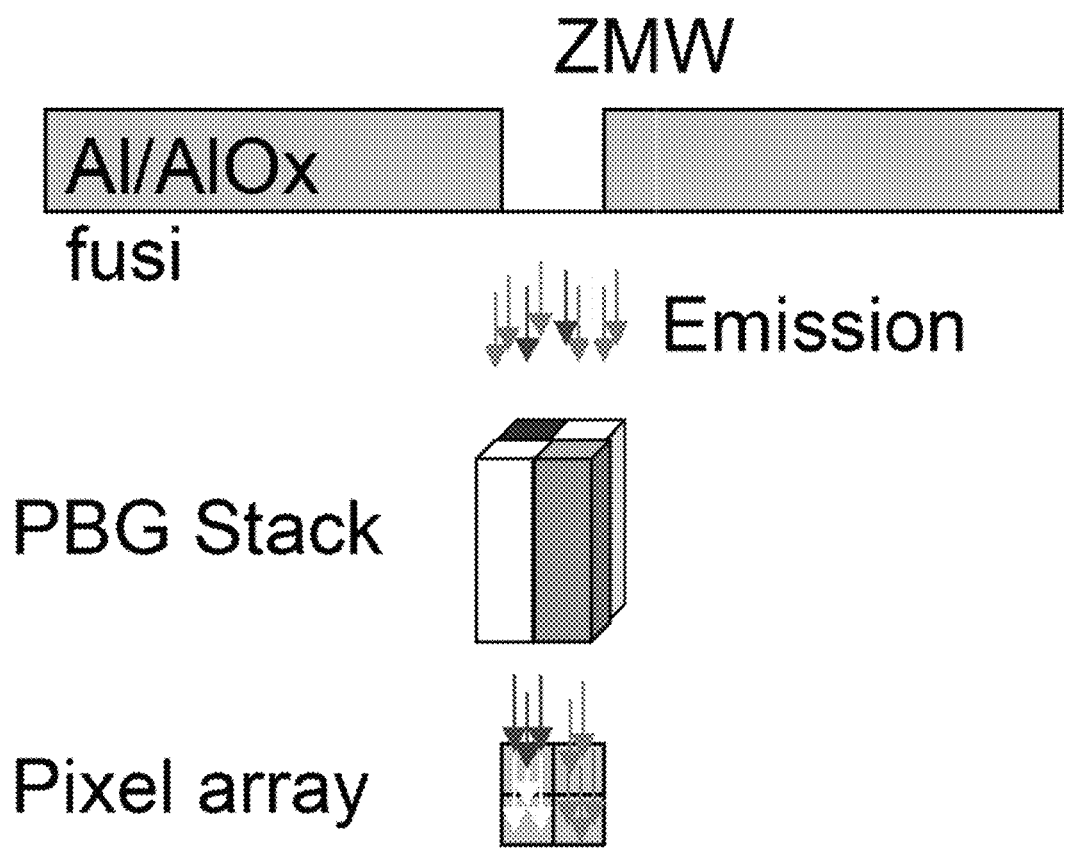
FIG. 32 is a schematic representation of an analytic device converting emission profiles suitable for use in the system of FIG. 1.

In some embodiments, emission from each channel is restricted using four photonic band gap stacks, as shown in FIG. 32, each only allowing one channel through to a spatially-sensitive sensor ("quad photodiode" or "position sensitive diode"). Each element of the PBG stack will have the feature not only that it will only allow light through of the color for which the detector is assigned, the elements will reflect back the wavelengths that are not passed through. The reflected photons can bounce back off of the bottom of the cladding layer and again encounter the PBG stack. If the photon is not allowed through that element, it is reflected again. This feature provides for recycling of detected photons, which can be very useful in these types of systems where the number of photons to be measured can be low, and improvements in photon capture efficiency are important. In some embodiments a can, reflective tunnel, or cladding tunnel is provided around the PBG stack. The can comprises a set of reflective walls around the PBG stack which receives light from a particular ZMW. The can will have a spherical, square, or any other suitable profile, and can have straight or curved walls. The walls can comprise any reflective material including metals or dielectric stacks. Because the walls are reflective, they are also part of the path of some of the light rays emitted from the ZMW. The reflection of the walls of the can provide a further increase in efficiency of use of the photons reflected from the PBG stack as described above.

Thus, in some aspects, the invention provides an integrated device for measuring optical signals from an array of optical sources over time, the device comprising an array of elements, each element comprising: a top layer comprising an optical source that emits two or more optical signals, each optical signal comprising different wavelengths; a middle layer comprising a spectral diversion element comprising a PBG stack having two or more photon band gap (PBG) elements, each PBG element configured to allow light of a different transmission wavelength range through the element and to reflect light that is not in the transmission wavelength range; and a bottom layer comprising a detector; wherein each PBG element transmits light onto a different detection region of the detector, whereby the identity of the optical signal can be identified by the regions of the detector onto which light is transmitted. Generally the integrated device is configured such that some of the reflected light from one PBG element is reflected into another PBG element through which it is transmitted, thereby increasing the efficiency of photon detection compared to where no reflected light is detected.

The efficiency of reflection of light back into the PBG stack for photon recycling can be improved by providing a can corresponding to each optical source, e.g. ZMW, comprising walls of reflective material disposed in the middle layer, the can configured to reflect some light reflected by the PBG stack back to the PBG stack.

Figure 33:
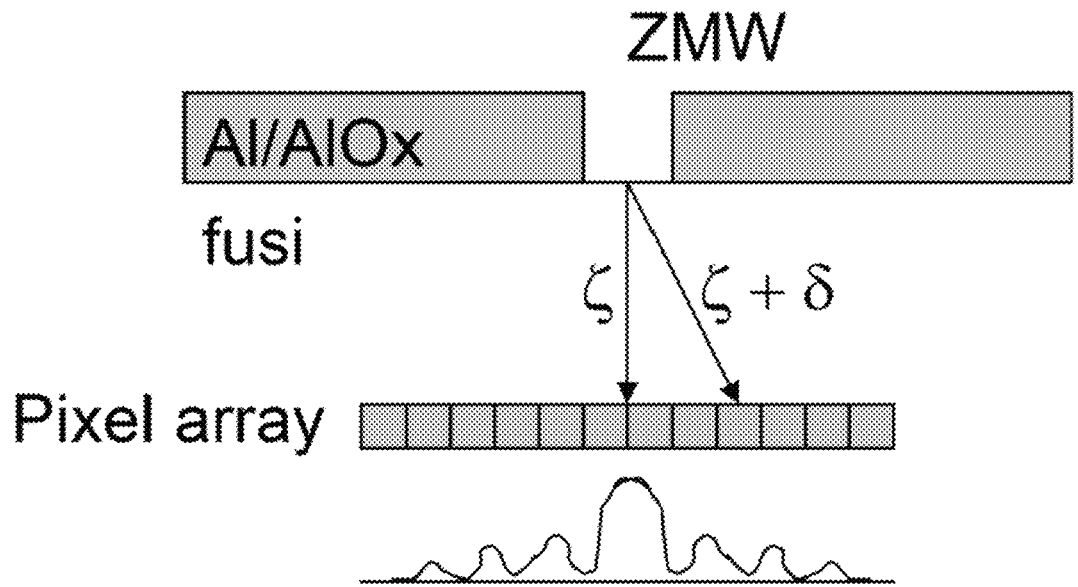
FIG. 33 is a schematic representation of an analytic device converting emission profiles suitable for use in the system of FIG. 1.

In other embodiments, optical path length (OPL) differences may create unique interference patterns for coherent emission from a single dye, as shown in FIG. 33. Two example paths have lengths $\lambda$ and $\lambda+\delta$ from source to array. If that difference in distance is an integer multiple of the wavelength of light ($\lambda$), then constructive interference occurs and the measured intensity (I) at that pixel is high; conversely, if $\delta \sim n\lambda/2$ then destructive interference causes the measured intensity at that pixel to be zero. In this manner, the measured pattern is related to the color of light. FIG. 34 illustrates this effect for two colors. In some cases a reflective can is created around each pixel in the region from the bottom of the cladding layer to the pixel array. The can comprises a set of reflective walls around the pixels which receive light from a particular ZMW. The can have a spherical, square, or any other suitable profile, and can have straight or curved walls. The walls can comprise any reflective material including metals or dielectric stacks. Because the walls are reflective, they are also part of the path of some of the light rays emitted from the ZMW. Thus, the presence of these walls can contribute to the constructive and destructive interference and thus can be used to control the way that colored light can be directed to different pixels at different intensity.

In some cases, a reflective can is disposed around multiple pixels disposed over a plurality of ZMWs, where each of the pixels detects light from more than one ZMW. Here, the destructive and constructive interference from the signals can be used to identify position as well as identifying wavelength.

Figure 35:
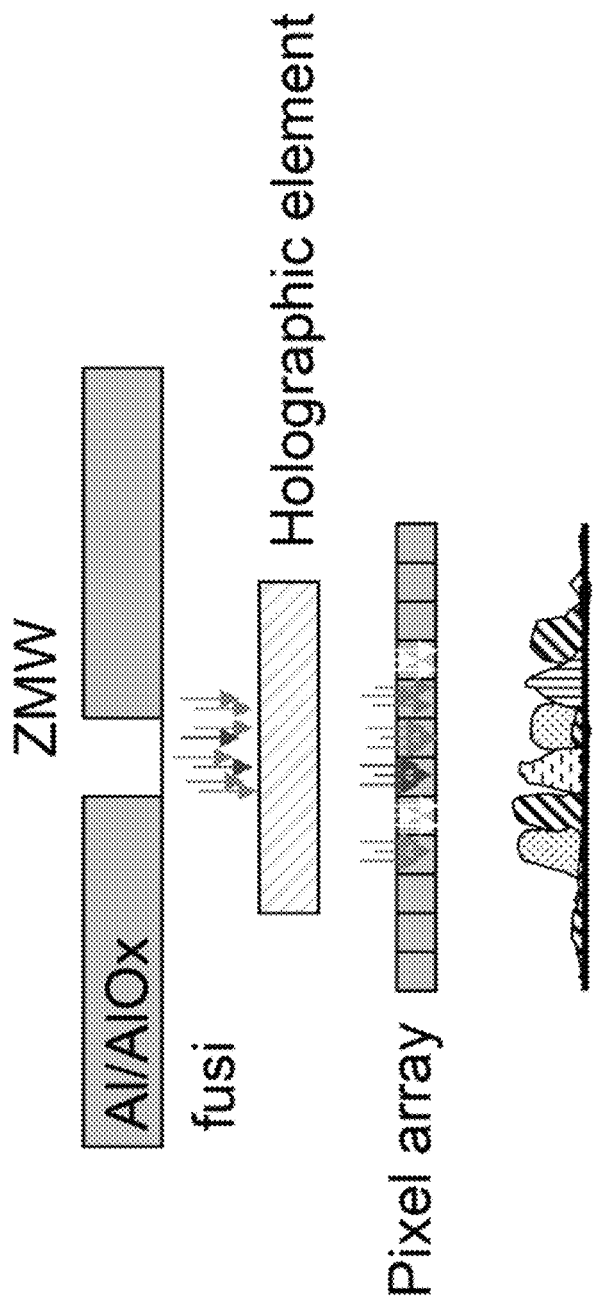
FIG. 35 is a schematic representation of an analytic device converting emission profiles suitable for use in the system of FIG. 1.

With reference to FIG. 35, a holographic medium may be inserted between the source and array, which controls the relative phase of light and creates highly non-linear interference patterns as a function of color. The pattern at the array is two dimensional, such that a full 2-D pixel array is essential for collecting as much light as possible while resolving the underlying pattern. However, at a minimum, a 1-D array "stripe" or a 2-D "pie-slice" might contain sufficient information distinguish multiple colors. Further, the pixel density must be sufficient to distinguish colors that lack significant spectral separation.

Stacked Junctions to Resolve Dye Spectra

Some aspects of the present invention are directed to methods to resolve the color of an emitted photon from a dye with a vertically stacked photodetector. The absorption depth in silicon is dependent on wavelength and can be excited to provide this spectral filtering. Silicon photodetectors have been used extensively in many applications. The photon is generally absorbed in a depleted region fanned by a reverse biased diode that is exposed to incoming light. The photoelectron is stored for readout. An important aspect is to generate a depletion region deep enough to gather the absorbed photons within a diffusion length of the extent. The absorption depth is dependent on the wavelength of the incident photon. Longer wavelengths are absorbed deeper in the material up to the point in the infrared where silicon is transparent.

By designing a photodetector with distinct regions of detector based on depth, spectral separation can be realized. Although similar sensors have been described, for example, in U.S. Pat. No. 6,911,712 which describes a stacked diode that is fabricated in standard CMOS processes. Methods according to the present invention leverage the principles that determination of four distinct colors from marker dyes is an easier task than traditional imaging color fidelity and a reduced set of diodes can be exploited. For example, with two stacked depletion regions sharing a common node, four spectral signatures can be determined based on the ratio of these two measurements. It is apparent that the depth separation can be used to resolve the color of the photon by designing the detector depletion widths to fall between these mean absorption depths.

For example, and with reference to FIGS. 41(a)-(d), a sacrificial top layer may be utilized to etch a basic detector into a mesa structure as shown. The processing for this detector may be performed in a modified CMOS process.

Figure 41A:
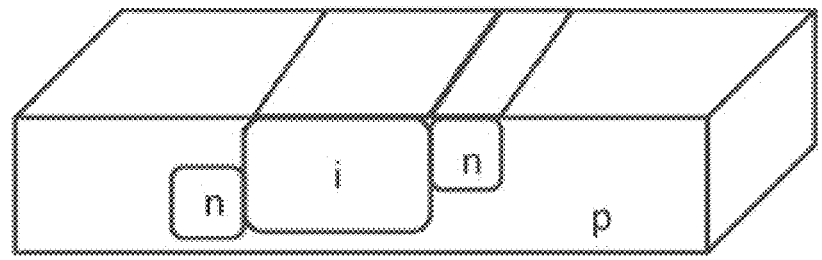
FIG. 41A to FIG. 41D is a schematic sequence of illustrating an exemplary method of fabricating an analytic device suitable for use in the system of FIG. 1
Figure 41B:
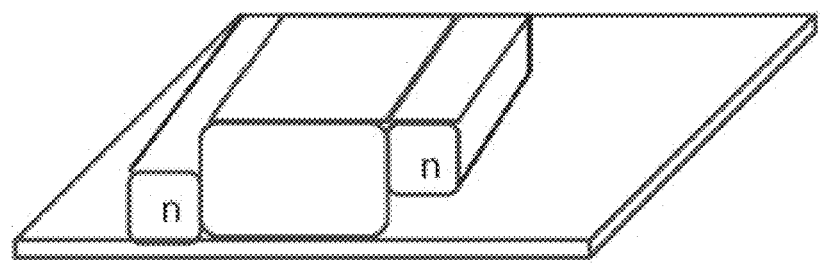
Figure 41C:
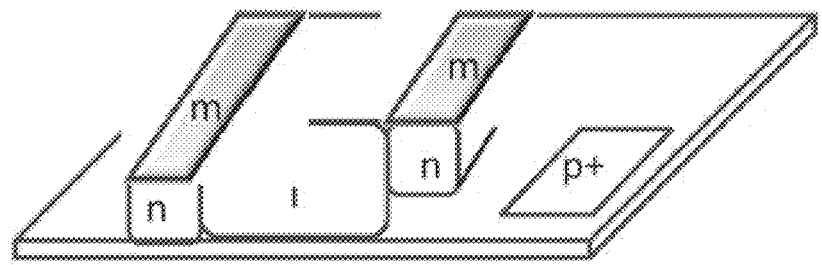
Figure 41D:
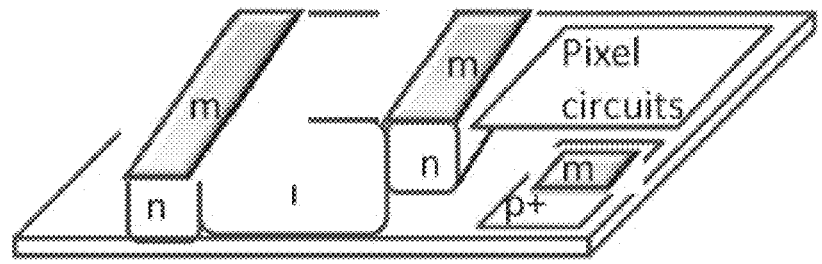

An intrinsic region (i) is grown on top of the p-type starting material (p). N-type regions (n) are placed at two (or more) different depths in the starting material layer (p). One way to accomplish this is to grow the lower (n) layer during the intrinsic layer deposition and the upper (n) layer diffused on the finished layer. Another approach would be to implant the lower (n) layer and diffuse the upper (n) layer on the finished intrinsic coat. The entire structure can then be masked and the intrinsic area around the pixel etched to the p-type substrate (stop) layer, as shown in FIG. 41(b). A mesa structure results with an upper n-layer suspended above the substrate (p). The CMOS circuitry can be patterned using relatively low temperature processes (e.g., below 1000° C.) to form the switching and amplification processing adjacent to the mesa. Finally a p+ contact diffusion is provided to the common photodiode cathode. The n-regions and the p+ contact may be metallized (see, e.g., FIG. 41(c) and bussed to the external I/O pads (see, e.g., FIG. 41(d).

Such a circuit may provide depth based photoelectron detection. The intrinsic layer is a high impedance path and isolating the field lines from each n-type pickup may be tuned via doping. An alternative layout is to use a graded n-type doping instead of an intrinsic layer. Such increasing resistance provides a field which can separate electrons based on depth.

CMOS Pixel for Detection of Fluorescent Lifetimes

Some aspects of the invention relate to methods of distinguishing different fluorophores by their unique decay lifetimes. These tend to be relatively high speed events, and the devices of the invention are highly multiplexed. The determination of high speed events at high resolution can be hampered by the need to distribute high speed clocks across a large array. However, as described herein, taking advantage of high speed drift regions in CMOS pixel circuits, the signature of short term events such as fluorescent decay can be made to discriminate between different tag data without clock distribution issues.

Figure 36:
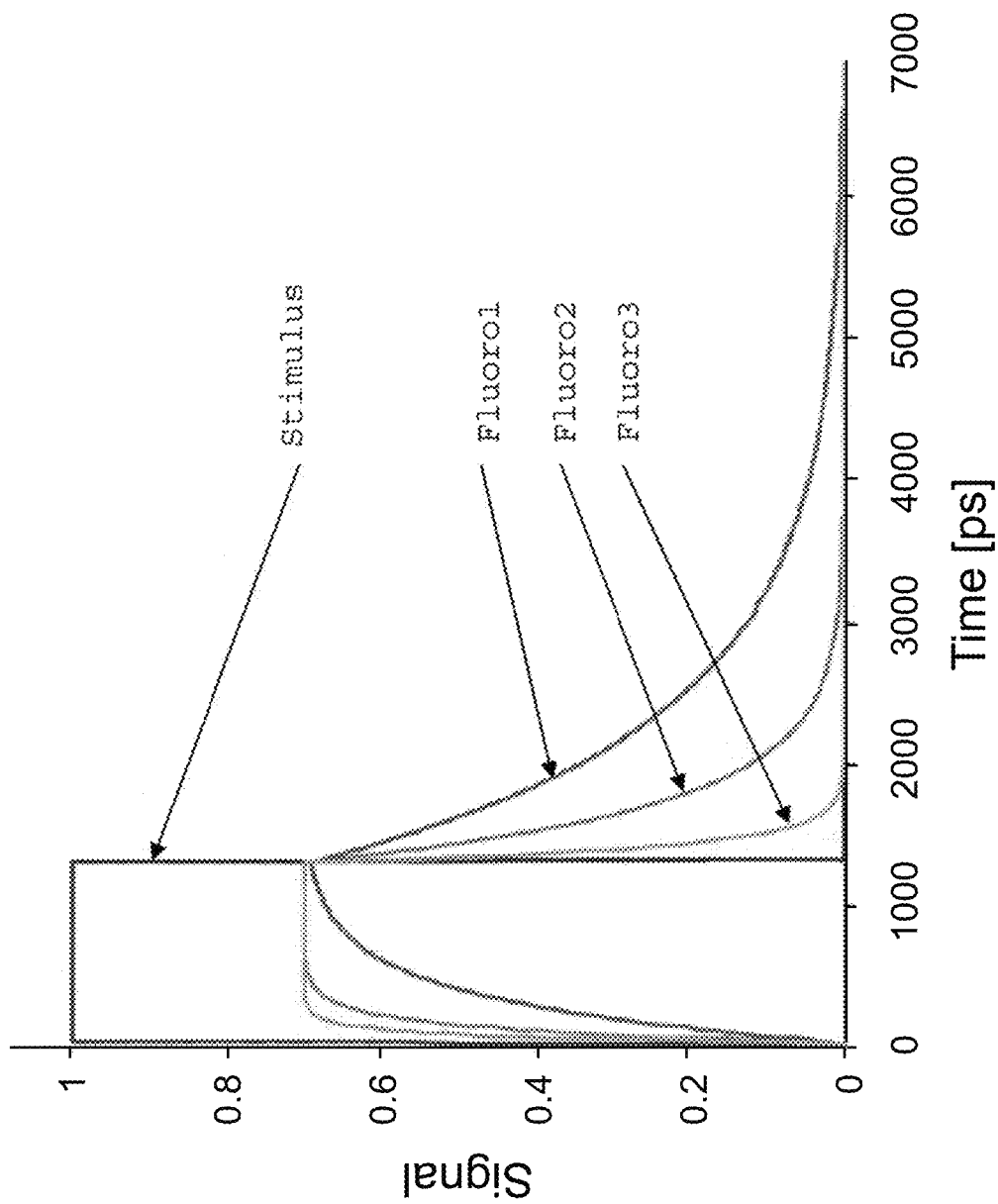
FIG. 36 is a graph illustrating the response of exemplary fluorophores to a stimulus.

The detection of molecules has been successfully performed using fluoroscopic dye and nanoparticle tags attached to the reactant molecules. In applications like DNA sequencing, the identification of a DNA nucleotide is important to determine the sequence of the polymer. As shown in FIG. 36, different fluorophores can respond to a stimulus with different turn on and decay constants. Detection schemes that can utilize decay lifetimes to identify the species are in wide application in several applications. However, the present methods for determining the lifetime of the decay are not readily transferable to high resolution and high speed sequencing architectures.

In accordance with the present invention, a CMOS pixel is configured to determine different species of chemical tags by means of processing high speed lifetime decay signatures. This pixel uses a high field to drive photocharge down a drift region. This charge is frozen by inhibiting the field and is stored in a set of analog storage devices (i.e., charge transfer gates). These regions can be interrogated to determine the relative or absolute decay rates to determine the species of illumination.

Also disclosed are novel methods of utilizing charge binning to improve the SNR of fluorophore time signatures and variable time resolution customized at the time of use for specific lifetime profiles to gain maximum discrimination.

A solid state sensor uses photoconversion of photons to charge carriers to sense the optical signal. These charge carriers are generally integrated in a capacitance element within the pixel that can be formed by a depletion region in a reverse biased junction. These charges can be controlled by electro-dynamic or magnetic forces that can be applied by the supporting circuitry. In various embodiments, a charge transfer device such as a CCD, the charge packets are serially transferred from one location to another by applying various potentials to gates in the proximity to the charge packet.

There are two main mechanisms of charge mobility in imaging devices. Diffusion causes charged particles to move from areas of higher concentration to lower concentration areas. These particles also drift when under the influence of electric or magnetic fields. The equations describing the charge flow (current density) for each of these effects are described by:

$$J_{diffusion} = qD(dn/dx) \qquad \text{Eq. (2)}$$

$$J_{drift} = \sigma E \qquad \text{Eq. (3)}$$

In various embodiments, a device uses the drift current mechanism to rapidly transport incident photocurrent through a narrow depletion region during all or a portion of the exposure time. The applied electric field causes the charged particles to move with a velocity that can be used to determine the arrival time of the particle based upon the distance traveled in a given time period. The distance traveled can be varied by controlling the applied voltage. It is disclosed that the applied voltage can be varied during the exposure time to extend the event duration or apply additional resolution the a smaller portion of the entire event.

By determining both the drift and the diffusion components, systematic variations in doping density, chip temperature and mobility are cancelled to improve the accuracy and uniformity of the array measurements.

A typical electron drift velocity is determined by the temperature, the total doping and the electron's effective mass. At low electric fields, the majority of electron collisions are with acoustic phonons and impurities. At high electric fields, the number of collisions is more temperature dependent and the carriers interact more with nonpolar optical phonons and the electron reaches velocity saturation. This value has been derived from measured data and numerical simulations and is described by:

$$v = ((2.4 \times 10^5)/(1 + 0.8 e^{T/600})) * m/s \qquad \text{Eq. (4)}$$

For example, at 30° C., the saturation velocity is about 100,000 m/s. If a drift region is designed with a length of 50 microns, the electrons will traverse this distance in 500 picoseconds. If the region is divided into 10 equal lengths, the time resolution of pulses traveling along the drift region is 50 picoseconds.

Figure 37:
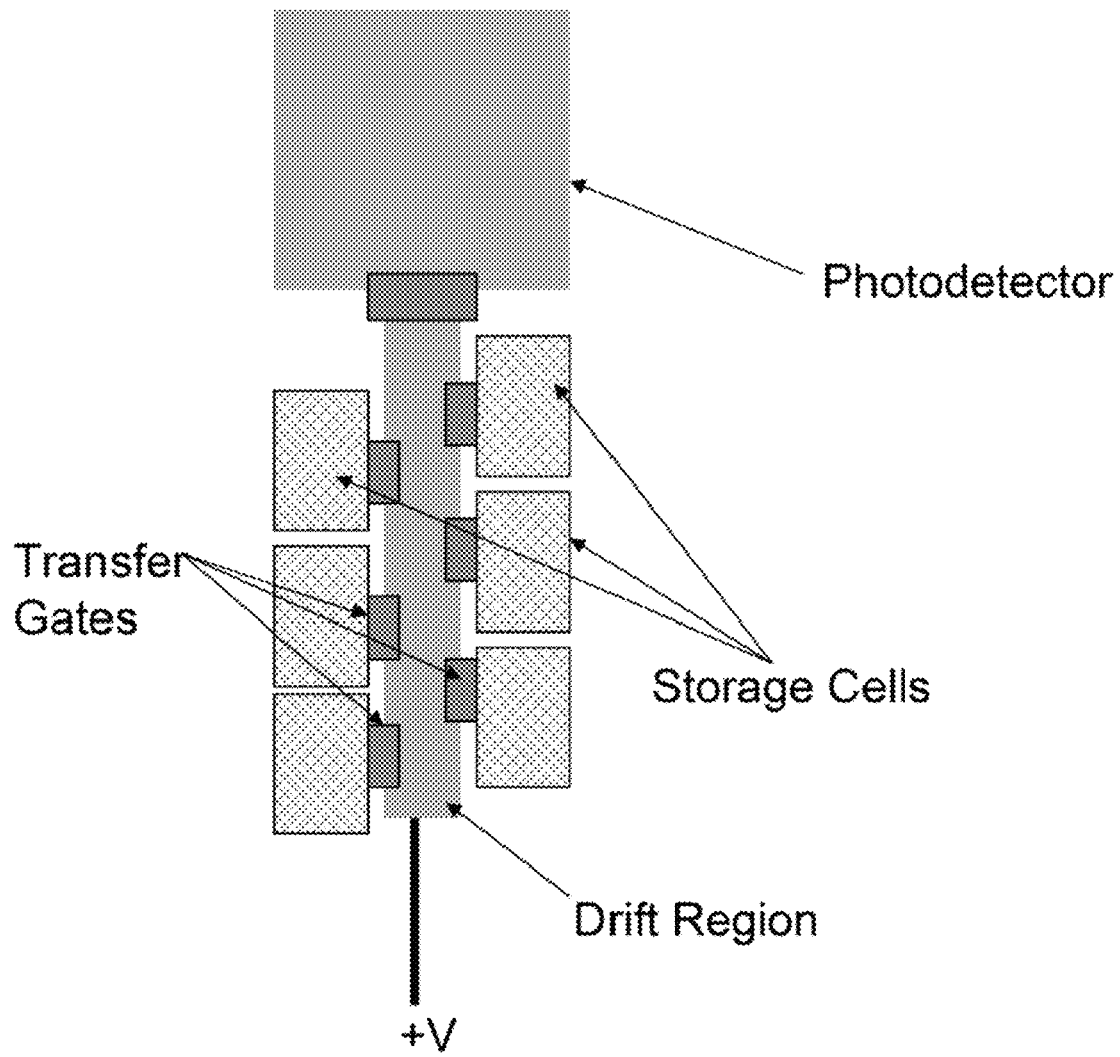
FIG. 37 is a schematic representation of a photodetector with a drift region and storage suitable for use in the system of FIG. 1.

In addition to the drift channel, a means to capture the time signature of this signal is disclosed. In one example, an adjacent set of capacitors is placed next to the drift channel and the signal is transferred laterally at the end of the exposure time. This is shown in FIG. 37. A typical operation of this pixel requires that synchronization with the stimulus signal is used as gate to start the drift. A transfer gate between the photodetector and the depletion drift region is shown that can be used for this gating. The voltage across the drift region can be varied to reduce the electron velocity. The resolution per equal spaced stage is therefore L/vd where L is the stage length and vd is the drift velocity. The voltage across the drift region needs to be stopped to freeze the waveform at a specific time after the stimulus to capture the waveform (if a fluorophore is present).

Soon after the waveform is frozen, it is transferred to the storage nodes across the transfer gates. It is disclosed that many pulses can be summed in the storage nodes to increased sensitivity. For example, a fluorophore used to determine the incorporation of a reactant into a polymer can be active for a much longer time than the pulse decay duration (i.e., 50 milliseconds). If the pulse decay response were 10 nanoseconds and a stimulus with high repetition rate were used, up to 5 million pulses could be applied to each incorporation event and stored in the drift region elements (up to the charge storage capacity).

In another embodiment, segmentation of the drift region can be performed with MOS gates above the region. The elements can then be sequentially read out similar to standard CCD readout methods (i.e., to a floating diffusion transimpedance amplifier). This prevents the diffusive mixing of the pulse after it is frozen. This method does not allow for the sequential missing of multiple stimulus response to increase sensitivity.

Figure 38:
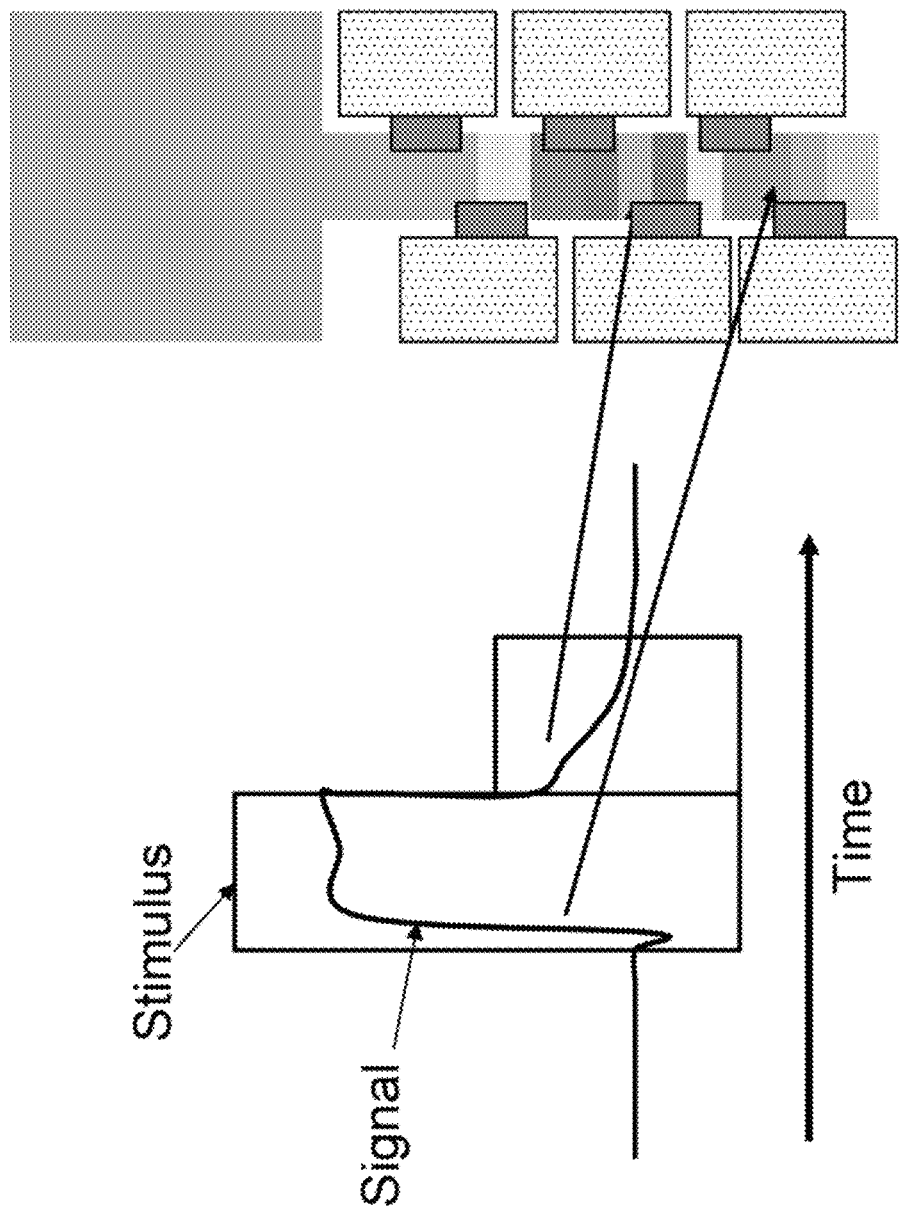
FIG. 38 is a schematic representation of a stimulus temporally filtered from a fluorophore decay signal in the drift region suitable for use in the system of FIG. 1.

It is disclosed that this method performs temporal filtering of the stimulus as the stimulus in inhibited during the decay time. Typically, the stimulus signal is transferred down the drift region ahead of the decay signal and does not mix. This temporal filtering provides an effective method of optical filtering of a sequence without the need for optical filters. This method is compatible with standard IC fabrication flows, as is shown graphically in FIG. 38. It is disclosed that the timing of the pixel can be set to allow for the stimulus signal to completely transfer to the drift region to maximize the resolution of the decay pulse.

The detection of this stimulus at the end of the drift region may automatically synchronize the detector elements—with the source—and gate the transfer of the signal to the storage nodes. This active feedback provides a higher level of synchronization and will result in higher fidelity data with less jitter.

Various methods of operating the device may continuously operate the drift region until a high intensity pulse is detected at the end of the drift region (signifying a stimulus pulse). The transfer of the decay signal. (received just after the stimulus in the drift region) is then performed and the system reset for the next event. This disclosed method eliminates the need for electrical communication and synchronization of the stimulus with each optode element and significantly increases the temporal uniformity of each element while reducing the complexity of the system.

The drift detection elements can be combined in the charge domain to further increase the signal to noise ratio at the expense of the temporal resolution.

The real time monitoring of these storage elements can be used to detect the presence of a fluorophore onset and the end of the event to assist in kinetic analysis of the incorporation. The storage nodes can be actively monitored and the ratio of the signals used to make real time analysis of the tagged species while the event is occurring. Using these methods, the full incorporation signal is integrated in a single sample to dramatically increase the sensitivity of the measurement and reduce the device readout bandwidth. The samples are processed to produce a single output signal with the tag species identification. This method provide for the decoupling of output bandwidth with in-pixel temporal resolution.

By making the drift length much greater than the photodetector length, the maximum temporal sensitivity is gained as the charge transport across the photodetector is minimized.

Figure 39:
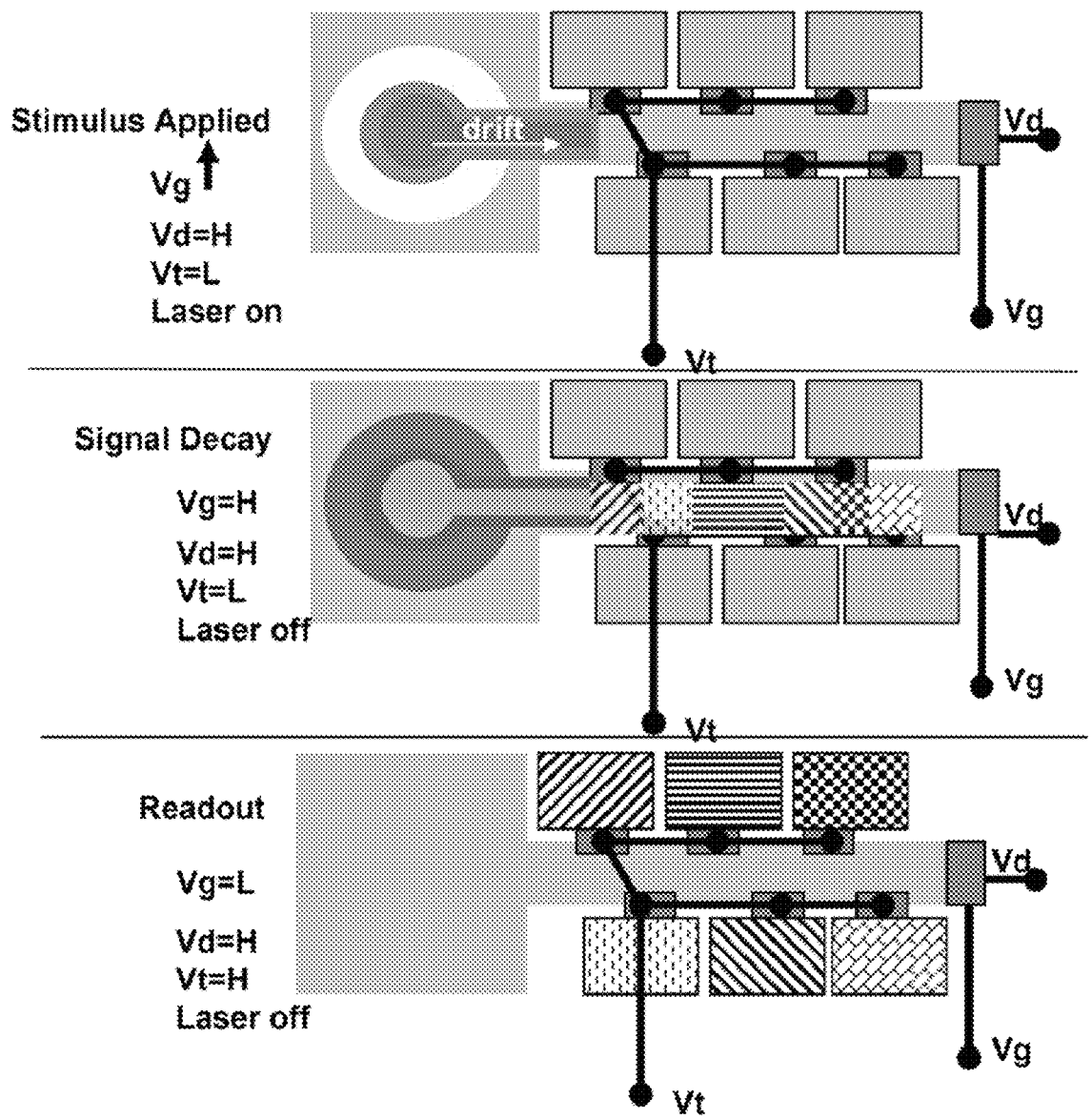
FIG. 39 is a schematic representation of a basic single pulse operation of a drift optode suitable for use in the system of FIG. 1.
Figure 40:
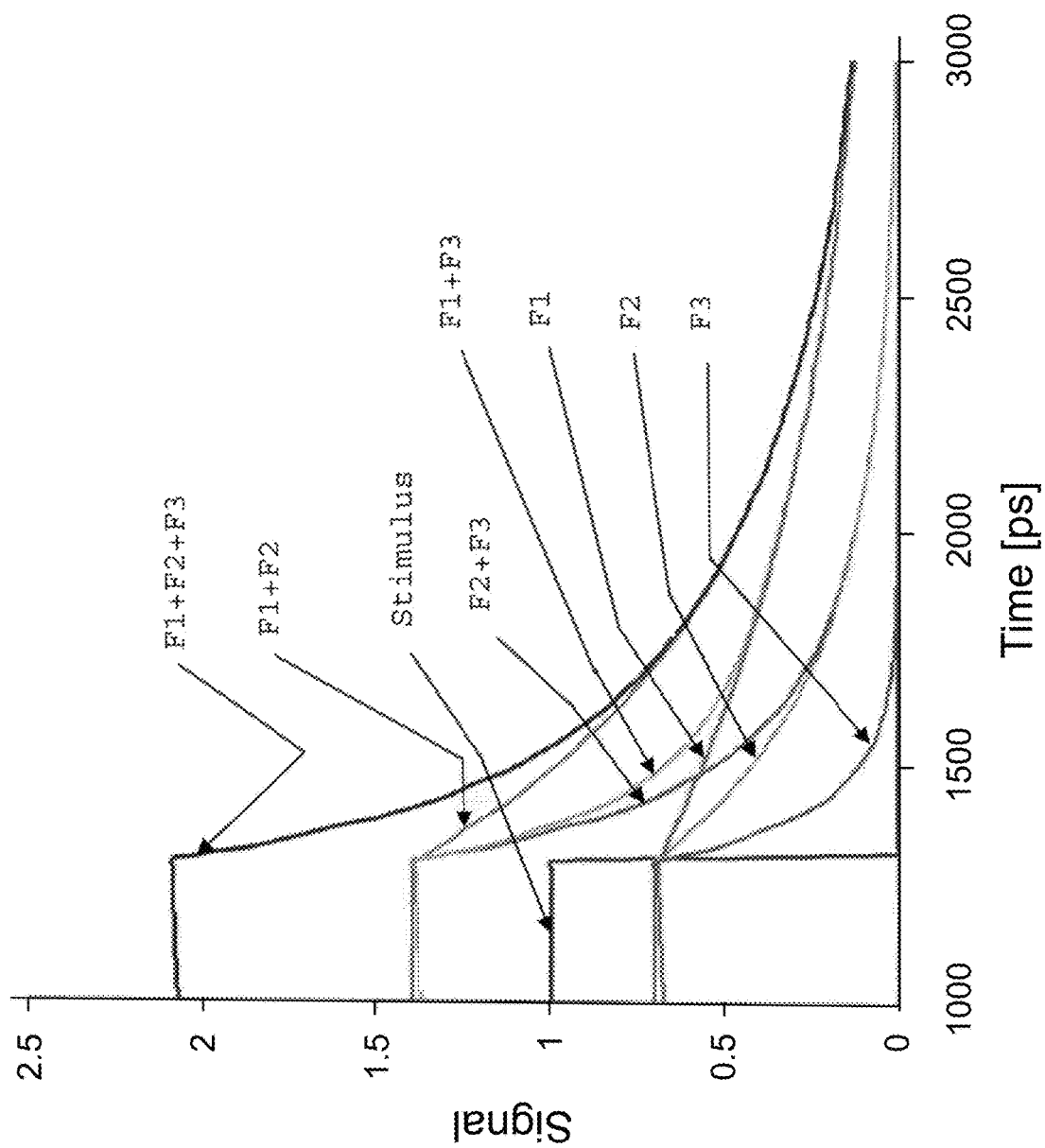
FIG. 40 is a graph illustrating the decay response for different fluorophore combinations.

With increased time resolution and samples, multiple superimposed decay waveforms can be captured and deconvolved. As shown in FIG. 39, a combination of fluorophore example decays or simultaneously input to the drift optode. Each has a specific decay signature independent of the intensity. This combination can be made to study simultaneous events to increase the data density or to use multiple fluorophore combinations to increase the available number of tags per dye set. A system designed with this invention can be made to resolve multiple simultaneous events with high accuracy within an optode that is called in the 10 micron scale. An array of these drift optodes can be designed to provide a massive multiplex of sequencing data without any optical filtering.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An integrated device for analysis of fluorescent species, comprising:
    an array of reaction cells comprising nanoscale apertures;
    at least one illumination waveguide disposed beneath the array of reaction cells extending across a plurality of reaction cells in the array of reaction cells and illuminating the plurality of reaction cells from below so that fluorescent species in the plurality of reaction cells emit fluorescent light;
    an array of optical filter elements disposed below the at least one illumination waveguide and selectively passing the fluorescent light emitted from the plurality of reaction cells, wherein corresponding to each respective reaction cell in the plurality of reaction cells, there are a first filter element and a second filter element, wherein the first filter element is configured to allow fluorescent light from a first signal to pass and reject fluorescent light from a second signal, and the second filter element is configured to allow fluorescent light from the second signal to pass and reject the fluorescent light from the first signal, wherein the first signal is at a first wavelength range and the second signal at a second wavelength range, wherein the second wavelength range is different than the first wavelength range; and
    an array of detector elements disposed below the array of optical filter elements to detect the fluorescent light passed through the array of optical filter elements, wherein corresponding to each respective reaction cell in the plurality of reaction cells, there are a first single detector element configured to receive the first signal that passes through the first filter element, and a second single detector element configured to receive the second signal that passes through the second filter element, wherein the first single detector element and the second single detector element each comprise a single pixel;
    wherein the device is integrated such that the fluorescent light emitted from the fluorescent species in the array of reaction cells is transmitted to the array of sensor elements without passing through air or free space.

2. The device of claim 1, further comprising one or more optical elements configured to direct the fluorescent light to the detector elements.

3. The device of claim 2, wherein the optical elements are selected from lenses, filters, gratings, mirrors, prisms, and refractive material.

4. The device of claim 1, wherein the single pixel is a CMOS pixel.

5. The device of claim 1, wherein the single pixel comprises two or more stacked junctions.

6. The device of claim 1, wherein the nanoscale apertures define nanoscale wells.

7. The device of claim 6, wherein the nanoscale wells comprises zero mode waveguides.

8. The device of claim 1, wherein the nanoscale apertures define optical confinement structures.

9. The device of claim 1, wherein the fluorescent species comprise distinctly labeled nucleotides.

10. The device of claim 1, wherein the fluorescent species comprise four distinct fluorescent labels.

11. The device of claim 10, wherein the four distinct fluorescent labels comprise four distinctly labeled nucleotides.

12. The device of claim 10, wherein the reaction cells comprises a biomolecule.

13. The device of claim 12, wherein the biomolecule is a polymerase.

14. The device of claim 1, wherein the reaction cells comprise immobilized primer template polymerase complexes.

15. The device of claim 1, wherein the device comprises a fluidic conduit configured to provide reagents across the array of reaction cells.

16. The device of claim 1, wherein the device is configured to perform single molecule real time DNA sequencing.

17. The device of claim 1, wherein the device is configured to detect kinetics of nucleotide incorporation.

18. The device of claim 1, wherein the device is configured to detect a binding reaction.

19. The device of claim 1, wherein the device is configured to detect a hybridization reaction.

20. The device of claim 1, wherein the device is configured to perform an antibody assay.

* * * * *